US012405279B2

(12) United States Patent
Pehla et al.

(10) Patent No.: US 12,405,279 B2
(45) Date of Patent: *Sep. 2, 2025

(54) METHOD FOR PREPARING A SAMPLE

(71) Applicant: B.R.A.H.M.S GmbH, Hennigsdorf (DE)

(72) Inventors: Aline Pehla, Hennigsdorf (DE); Stefan Kirsch, Hennigsdorf (DE); Darius Wilson, Lorrach (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 15 days.

This patent is subject to a terminal disclaimer.

(21) Appl. No.: 17/710,329

(22) Filed: Mar. 31, 2022

(65) Prior Publication Data
US 2022/0221474 A1    Jul. 14, 2022

Related U.S. Application Data

(63) Continuation of application No. 16/646,798, filed as application No. PCT/EP2018/074725 on Sep. 13, 2018, now Pat. No. 11,327,082.

(30) Foreign Application Priority Data

Sep. 13, 2017  (EP) .................................... 17190912
Mar. 9, 2018   (EP) .................................... 18161091

(51) Int. Cl.
G01N 33/74    (2006.01)
G01N 33/86    (2006.01)

(52) U.S. Cl.
CPC ............. G01N 33/74 (2013.01); G01N 33/86 (2013.01); G01N 2800/222 (2013.01); G01N 2800/50 (2013.01); G01N 2800/52 (2013.01)

(58) Field of Classification Search
CPC .. G01N 33/74; G01N 33/86; G01N 2800/222; G01N 2800/50; G01N 2800/52
See application file for complete search history.

(56) References Cited

U.S. PATENT DOCUMENTS

| 7,915,002  | B2  | 3/2011  | Bergmann |
| 7,939,639  | B2  | 5/2011  | Cuttitta et al. |
| 7,972,799  | B2  | 7/2011  | Bergmann et al. |
| 8,507,210  | B2  | 8/2013  | Bergmann et al. |
| 8,772,239  | B2  | 7/2014  | Tsuruta et al. |
| 9,012,151  | B2* | 4/2015  | Ng .......................... G01N 33/74 435/7.1 |
| 9,229,013  | B2  | 1/2016  | Bergmann et al. |
| 9,541,549  | B2  | 1/2017  | Bergmann et al. |
| 2006/0029589 | A1 | 2/2006 | Weiler |
| 2007/0154472 | A1* | 7/2007 | Widom .............. C07K 16/2896 435/7.1 |
| 2008/0261258 | A1* | 10/2008 | Smith ................... G01N 33/574 435/287.1 |
| 2009/0110683 | A1* | 4/2009 | Xu .......................... C07K 16/40 530/387.3 |
| 2009/0191220 | A1* | 7/2009 | Bergmann ............. C07K 16/22 435/29 |
| 2010/0062463 | A1* | 3/2010 | Bergmann .......... G01N 33/6896 435/7.94 |
| 2010/0292131 | A1 | 11/2010 | Kas et al. |
| 2011/0086831 | A1 | 4/2011 | Bergmann et al. |
| 2012/0094314 | A1 | 4/2012 | Bahrami et al. |
| 2012/0142120 | A1 | 6/2012 | Bergmann et al. |
| 2012/0222142 | A1* | 8/2012 | Kim ........................ A61P 31/04 424/257.1 |
| 2013/0195875 | A1* | 8/2013 | Bergmann ............. C07K 16/26 424/139.1 |
| 2013/0203612 | A1 | 8/2013 | Graf et al. |
| 2013/0302841 | A1 | 11/2013 | Struck et al. |

(Continued)

FOREIGN PATENT DOCUMENTS

EP    1488209 B1    12/2005
EP    2320237 B1    8/2016

(Continued)

OTHER PUBLICATIONS

Suberviola Intensive Care Med. 2013 39:1945-1952 (Year: 2013).*
Aydemir Platees 2015 vol. p. 331-335 (Year: 2015).*
Wu J. Critical Care 2014 vol. 29, p. 362-366 (Year: 2014).*
Gunnink Expert Rev. Hematol. 2014 vol. 7, p. 387-395 (Year: 2014).*
Sharma "Thrombocytopenia in septic shock patients—a prospective observational study of incidence, risk factors and correlation with clinical outcome" (Anaesth Intensive Care 2007 35:874-880). (Year: 2007).
Annane "Corticosteroids for severe sepsis: an evidence-based guide for physicians." (Annals of Intensive Care 2011 1:7, total 7 pages). (Year: 2011).

(Continued)

Primary Examiner — Changhwa J Cheu
(74) Attorney, Agent, or Firm — Millen, White, Zelano & Branigan P.C.; Ryan R. Pool

(57) ABSTRACT

The invention relates to a method for determining, diagnosis, prognosis, treatment guidance, treatment monitoring, risk assessment and/or risk stratification of patients with abnormal platelet levels comprising providing a sample of said patient, determining a level of proadrenomedullin (proADM) or fragment(s) thereof in said sample, wherein said level of proADM or fragment(s) thereof correlates with the abnormal platelet levels in said patient. In embodiments of the invention, a level of proADM or fragment(s) thereof of high severity indicates low platelet levels in the subject and subsequent initiating or modifying a treatment of the patient to improve said condition. In some embodiments of the invention the method comprises determining a level of one or more additional markers in a sample isolated from the patient, such as the level of platelets, the level of PCT or fragment(s) thereof, one or more markers of thrombocytopenia and/or one or more markers of an inflammatory response.

17 Claims, No Drawings
Specification includes a Sequence Listing.

(56) References Cited

U.S. PATENT DOCUMENTS

| | | | |
|---|---|---|---|
| 2015/0011017 A1 | 1/2015 | Bergmann et al. | |
| 2015/0118699 A1 | 4/2015 | Ishikura | |
| 2015/0119271 A1* | 4/2015 | Struck | G01N 33/6893 |
| | | | 435/7.92 |
| 2017/0010286 A1 | 1/2017 | Bergmann | |
| 2017/0128459 A1* | 5/2017 | Kim | A61K 31/713 |
| 2017/0370949 A1 | 12/2017 | Struck et al. | |
| 2018/0348235 A1 | 12/2018 | Viguéet al. | |
| 2019/0178894 A1* | 6/2019 | Ziera | G01N 33/68 |
| 2019/0376985 A1 | 12/2019 | Bergmann et al. | |
| 2021/0156850 A1 | 5/2021 | Anderberg et al. | |

FOREIGN PATENT DOCUMENTS

| | | |
|---|---|---|
| WO | 9707214 A1 | 2/1997 |
| WO | 0242770 A1 | 5/2002 |
| WO | 04090546 A1 | 10/2004 |
| WO | 2004090546 A1 | 10/2004 |
| WO | 08012019 A2 | 1/2008 |
| WO | WO09062948 A1 | 5/2009 |
| WO | 10128071 A1 | 11/2010 |
| WO | 2010128071 A1 | 11/2010 |
| WO | 10139475 A1 | 12/2010 |
| WO | 12059477 A1 | 5/2012 |
| WO | 13086359 A1 | 6/2013 |
| WO | 14147153 A1 | 9/2014 |
| WO | 17089474 A1 | 6/2017 |
| WO | 18007588 A1 | 1/2018 |
| WO | 18029214 A1 | 2/2018 |

OTHER PUBLICATIONS

De La Torre-Prados "Mid-regional pro-adrenomedullin as prognostic biomarker in septic shock" (Minerva Anestesiologica 2016 82: 760-766 (Year: 2016).
Levi "Platelets in sepsis." Hematology 2005 10 Suppl. 1:129-131 (Year: 2005) doi: 10.1080/10245330512331390177.
Guclu et al. "Effect of severe sepsis on platelet count and their indices" African Health Sciences 2013 13:333-338 (Year: 2013).
Lale et al. "Dengue fever and thrombocytopenia: A dealy duo" Blood 2006 108: 3978 (Abstract) (Year: 2006).
Michels et al. (II) "Platelet function alterations in dengue are associated with plasma leakage" Thrombosis and Haemostasis 2014 112:352-362 (Year: 2014).
International Search Report for PCT/EP2018/074725 dated Oct. 9, 2018.
Michels, M. et al., "High plasma mid-regional pro-adrenomedullin levels in children with severe dengue virus nfections," Journal of Clinical Virology, Journal of Clinical Virology, 2011, vol. 50, pp. 8-12.
Kalayanarooj, S., "Clinical Manifestations and Management of Dengue/DHF/DSS," Tropical Medicine and Health, J011, vol. 39, No. 4 Supplement, pp. 83-87.
Hanachartwet, V. et al., "Serum procalcitonin and peripheral venous lactate for predicting dengue shock and/ Jr organ failure: a prospective observational Study," Plos Neglected Tropical Diseases, Aug. 26, 2016, 19 pages.
Anadaluz-Ojeda D. et al. : "Superior accuracy of mid-regional proadrenomedullin for mortality prediction in sepsis with varying levels of illness severity", Intensive Care, vol. 7, Feb. 10, 2017, Article No. 15, pp. 1-8.
Angeletti S. et al. : "Diagnostic and prognostic role of procalcitonin (PCT) and MR-pro-Adrenomedullin (MR-proADM) in bacterial infections", APMIS, vol. 123, No. 9, Jun. 8, 2015 (Jun. 8, 2015), pp. 740-748.
Angeletti S. et al: "Procalcitonin and mid-regional pro-adrenomedullin test combination in sepsis diagnosis", Clinical Chemistry and Laboratory Medicine, De Gruyter, DE, vol. 51, No. 5, Apr. 30, 2013 (Apr. 30, 2013), pp. 1059-1067, XP009502330, ISSN: 1434-6621, DOI: 10.1515/CCLM-2012-0595.

Bruno Viaggi et al: "Mid regional pro-adrenomedullin for the prediction of organ failure in infection. Results from a single centre study", Plos One, vol. 1 3, No. 8, Aug. 13, 2018 (Aug. 13, 2018), p. e0201491, xP055535888, DOI : 10137 1/journal.pone.0201 491.
Cairon Pietr-et al: "Circulating Biologically Active Adrenomedullin such statement (bio-ADM) Predicts Hemodynamic support Requirement and Mortality During Sepsis", Chest, vol. 152, No. 2, Aug. 1, 2017 (Aug. 1, 2017), pp. 312-320, XP55430860.
Caroline Guignant et al: "Assessment of pro-vasopressin and proadrenomedullin as predictors of 28-day mortality in septic shock patients", Intensive Care Medicine, vol. 35, No. 1 1 , Aug. 7, 2009 (Aug. 7, 2009), pp. 1859-1867, xP055535903, DE ISSN: 0342-4642, DOI: 10.1 007is001 34-009-1 610-5.
Charles P.-E. et al: "MR-ProADM elevation upon ICU admission predicts the outcome of septic patients and is correlated with upcoming fluid overload", Shock, vol. 48, No. 4, Oct. 2017, pp. 418-426.
Christ-Crain M ei al: "Biomarkers in respiratory tract infections: diagnostic guides to antibiotic prescription, prognostic markers and mediators", European Respiratory Journal, Munksgaard International Publishers, Copenhagen, DK, vol. 30, No. 3, Aug. 31, 2007 (Aug. 31, 2007), pp. 556-573, XP00950261 1.
Christ-Crain M.: "Procalcitonin Guidance of Antibiotic in Community-acquired Pneumonia: A Randomized Trial", American Journal of Respiratory Critical Care Med—Cine, vol. 174, No. (Jan. 1, 2006), pp. 84-93, XP055021 728, ISSN: 1 073-449X, DOI: 10.11 64/rccm. 200512-1 9220C.
Christ-Crain Mirjam et al: "Mid-regional proadrenomedullin as a prognostic marker in sepsis: an study", Critical Care, Biomed Central London, GB, vol. 9, No. 6, Nov. 15, 2005 (Nov. 15, 2005), pp. R81 6- R824, XP021 012417, ISSN: 1364-8535, DOI: 10.11 86/CC3885.
De Jong Evelien ei al: "Efficacy and safety of procalcitonin guidance in reducing the duration of antibiotic treatment—n critically patients: a randomised, controlled, open-label trial", Lancet Infectious Diseases, Elsevier Lid, US, vol. 16, No. 7,Mar. 2, 2016 (Mar. 2, 2016), pp. 819-827, XP02961 8593.
De La Torre-Prados Maria V et al: "Mid-regional proadrenomedullin as prognostic biomarker in septic shock", Minerva Anestes-Olog-Ca G-Ornale Italiano Di Anestesia E D—Analg, Societa Italiana Di An Estesiolog Ia, IT, vol. 82, No. 7, Jul. 1, 2016 (Jul. 1, 2016), pp. 760-766, XP0091 92235,ISSN 1827-1596.
Elke G. et al.: "The use of mid-regional proadrenomedullin to identify disease severity and treatment response to sepsis—a secondary analysis of a large randomised controlled trial", Crit. Care, vol. 22, No. 1, 79, Mar. 21, 2018 (Mar. 21, 2018), pp. 1-12, XP55556348.
Gille Jochen et al: "MR-proADM: A New Biomarker for Early Diagnosis of Sepsis in Burned Patients", Journal of Burn Care & Research, Williams & Wilkins, US, vol. 38, No. 5, Aug. 31, 2017 (Aug. 31, 2017), pp. 290-298, XP009502061.
Hartmann Oliver et al: "Time-dependent Cox regression: Serial measurement of the cardiovascular biomarker proadrenomedullin—mproves survival prediction in patients with—ower resp-ratory infection", International Journal of Cardiology, vol. 161, No. 3, Sep. 24, 2012, p. 166-173, XP028959234.
Michels M ei al: "High plasma mid-regional pro-adrenomedullin—evels in children with severe dengue virus—nfections ", Journal of Clinical Virology, Elsevier, Amsterdam, NL, vol. 50, No. 1, Jan. 1, 2011 (Jan. 1, 2011), pp. 8-12, XP027588087.
Munirah Al Shuaibi et al: "Pro-adrenomedullin as a Novel Biomarker for Predicting Infections and Response to Antimicrobials in Febrile Patients With Hematologic Malignancies", Clinical Infectious Diseases, vol. 56, No. 7,Jan. 3, 2013 (Jan. 3, 2013), pp. 943-950, xP055535801, US ISSN: 1 058-4838, DOI: 10.1 O93icidicis1 029.
Pereira J.M. et al: "Mid-regional proadrenomedullin: An early marker of response in critically community-acquired pneumonia?", Revista Portugu Esa De Pneumologia (English Edition), vol. 22, No. 6, Nov. 1, 2016 (Nov. 1, 2016), pp. 308-314, XP0554451 19, ISSN: 2173-5115, DOI: 10.1016/j.rppnen.2016 .03.012.
Rossella Marino et al: "Plasma adrenomedullin is associated with short-term mortality and vasopressor requirement in patients admitted with sepsis", Critical Care, Biomed Central Ltd., London, GB,

(56) References Cited

OTHER PUBLICATIONS vol. 18, No. 1,Feb. 17, 2014 (Feb. 17, 2014), p. R34, XP021179720, ISSN: 1364-8535, DOI: 10.1 186/CC13731.

Saeed K. et al.: "The early identification of disease progression in patients with suspected infection presenting to the emergency department: a multi-centre derivation and validation study", Crit. Care, vol. 23, No. 1, 40, Feb. 8, 2019 (Feb. 8, 2019), pp. 1-15, XP55556343, the whole document.

Schuetz Philipp el al: "Blood biomarkers for personalized treatment and patient management decisions in community-acquired pneumonia", Current Opinion On Infectious Diseases., vol. 26, No. 2, Apr. 1, 2013 (Apr. 1, 2013), pp. 159-167 , XP055439092.

Sebastian Decker et al: Immune-Response Patterns and Next Generation Sequencing Diagnostics for the Detection of Mycoses in Patients with Septic Shock-Results of a Combined Clinical and Experimental Investigation, International Journal of Molecular Sciences, vol. 18, No. 8, Aug. 18, 2017 (Aug. 18, 2017), p. 1796, XP055417185,DOI: 10.3390/ijm518081796.

Shuaibi M. Al et al: "Pro-adrenomedullin as a Novel Biomarker for Predicting Infections and Response to Antimicrobials in Febrile patients With Hematologic Malignancies", Clinical Infectious Diseases, vol. 56, No. 7,Jan. 3, 2013, p. 943-950, XP055418326.

Siripen Kalayanarooj: "Clinical Manifestations and Management of Dengue/DHF /DSS", Tropical Medicine and Health, vol. 39, No. 4SUPPLEMENT , Jan. 1, 2011 (Jan. 1, 2011), pp. S83-S87, XP055511310.

Thanachartwet Vipa ei al: "Serum Procalcitonin and Peripheral Venous Lactate for Predicting Dengue Shock and/or Organ Failure: A Prospective Observational Study", Plos Neglected Tropical Diseases, vol. 10, No. 8, Aug. 26, 2016 (Aug. 26, 2016), p. e0004961, XP055511330.

Ueda et al: "Increased plasma levels of adrenomedullin in patients with systemic inflammatory response syndrome.", Amer. J Resp. Crit. Care Med., vol. 160, No. 1, Jul. 1, 1999, pp. 132-136, XP055052609.

Wang R L et al: "Prediction about severity and outcome of sepsis by pro-atrial natriuretic peptide and pro-adrenomedullin", Chin. J. Traumatol, NL, vol. 13, No. 3, Jun. 1, 2010, pp. 152-157, XP027087080.

Bello et al. Prognostic power of proadrenomedullin in community-acquired pneumonia is independent of aetiology. Eur Respir J 2012; 39: 1144-1155.

Cavallazzi et al. Midregional proadrenomedullin for prognosis in community-acquired pneumonia: a systematic review. Respiratory Medicine (2014) 108, 1569e1580.

Courtais et al. Proadrenomedullin, a useful tool for risk stratification in high Pneumonia Severity Index score community acquired pneumonia. American Journal of Emergency Medicine (2013) 31, 215-221.

Curbelo et al.Inflammation biomarkers in blood as mortality predictors in community-acquired pneumonia admitted patients: Importance of comparison with neutrophil count percentage or neutrophil-lymphocyte ratio. Plos One | https://doi.org/10.1371/journal.pone. 0173947 Mar. 16, 2017 (pp. 1-14).

Debiane et al. The utility of proadrenomedullin and procalcitonin in comparison to C-reactive protein as predictors of sepsis and bloodstream infections in critically ill patients with cancer. Crit Care Med. Dec. 2014 (pp. 1-9) DOI: 10.1097/CCM.0000000000000526.

Gordo-Remartínez.Usefulness of midregional proadrenomedullin to predict poor outcome in patients with community acquired pneumonia. Plos One | DOI:10.1371/journal.pone.0125212 Jun. 1, 2015 (pp. 1-15).

Hoeboer SH et al. Old and new biomarkers for predicting high and low risk microbial infection in critically ill patients with new onset fever: a case for procalcitonin. Journal of Infection (2012) 64, 484e493.

Huang et al. Midregional proadrenomedullin as a prognostic tool in community-acquired pneumonia. Chest / 136 / 3 / Sep. 2009 pp. 823.

Lundberg et al. Adrenomedullin and endothelin-1 are associated with myocardial injury and death in septic shock patients. Critical Care (2016) 20:178.

Renaud et al. Proadrenomedullin improves Risk of Early Admission to ICU score for predicting early severe community-acquired pneumonia. Chest / 142 / 6 / Dec. 2012 1447.

Schuetz P et al. Circulating precursor levels of endothelin-1 and adrenomedullin, two endothelium-derived, counteracting substances, in sepsis. Endothelium. Endothelium, 14:345-351, 2007.

Suberviola et al. Prognostic value of proadrenomedullin in severe sepsis and septic shock patients with community-acquired pneumonia. Swiss Med Wkly. 2012;142:w13542.

Suberviola et al. Hospital mortality prognostication in sepsis using the new biomarkers suPAR and proADM in a single determination on ICU admission. Intensive Care Med 2013, pp. 1-12, DOI 10.1007/s00134-013-3056-z.

Travaglino F et al. Utility of Procalcitonin (PCT) and Mid regional pro-Adrenomedullin (MR-proADM) in risk stratification of critically ill febrile patients in Emergency Department (ED). A comparison with Apache II score. BMC Infect Dis. Aug. 8, 2012 (pp. 1-8).

\* cited by examiner

SEQUENCE LISTING

<160> NUMBER OF SEQ ID NOS: 2

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe

-continued

```
1               5                   10                  15
Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
            35                  40                  45

Ser Ser Ser Tyr Pro Thr Gly Leu Ala Asp Val Lys Ala Gly Pro Ala
            50                  55                  60

Gln Thr Leu Ile Arg Pro Gln Asp Met Lys Gly Ala Ser Arg Ser Pro
65                      70                  75                  80

Glu Asp Ser Ser Pro Asp Ala Ala Arg Ile Arg Val Lys Arg Tyr Arg
                    85                  90                  95

Gln Ser Met Asn Asn Phe Gln Gly Leu Arg Ser Phe Gly Cys Arg Phe
                    100                 105                 110

Gly Thr Cys Thr Val Gln Lys Leu Ala His Gln Ile Tyr Gln Phe Thr
            115                 120                 125

Asp Lys Asp Lys Asp Asn Val Ala Pro Arg Ser Lys Ile Ser Pro Gln
            130                 135                 140

Gly Tyr Gly Arg Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                    165                 170                 175

Pro Ser Gly Ser Ala Pro His Phe Leu
                180                 185

<210> SEQ ID NO 2
<211> LENGTH: 48
<212> TYPE: PRT
<213> ORGANISM: Homo sapiens

<400> SEQUENCE: 2

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
            35                  40                  45
```

METHOD FOR PREPARING A SAMPLE

The invention relates to a method for determining, diagnosis, prognosis, treatment guidance, treatment monitoring, risk assessment and/or risk stratification of patients with abnormal platelet levels, comprising providing a sample of said patient, determining a level of proadrenomedullin (proADM) or fragment(s) thereof in said sample, wherein said level of proADM or fragment(s) thereof correlates with the abnormal platelet levels in said patient. In embodiments of the invention, a high severity level of proADM or fragment(s) thereof indicates low platelet levels in the subject, and subsequent initiating or modifying a treatment of the patient to improve said condition. In some embodiments the method comprises determining a level of one or more additional markers in a sample isolated from the patient, such as the level of platelets, the level of PCT or fragment(s) thereof, one or more markers of thrombocytopenia and/or one or more markers of an inflammatory response.

BACKGROUND OF THE INVENTION

Despite significant improvements in diagnostic and preventative measures, the incidence of sepsis has continued to escalate rapidly in hospitalized patients (1), with mortality rates ranging between 10% and 54%, depending on the level of disease severity, definition of organ dysfunction used, and country specific incidence (2, 3). An early and accurate assessment of both the infectious load and disease severity, in terms of the overall pathophysiological host response, is therefore of crucial importance in the early stages of sepsis in order to make prompt and reliable decisions concerning diagnostic testing and treatment strategies, as well as in the later phase to reliably guide patient management, treatment monitoring, discharge decisions in the presence of clinical recovery.

It is therefore surprising that no gold standard diagnostic test for sepsis currently exists (4). The use of Procalcitonin (PCT) has partially filled this unmet need with regards to infectious load assessment, with observational and interventional data in the field of antibiotic guidance (5-7). However an accurate measure of disease severity has not yet been shown.

As such, numerous biomarkers and clinical scores have consequently been proposed, including the use of severity scores such as the Sequential Organ Failure Assessment (SOFA), Acute Physiological and Chronic Health Evaluation (APACHE) II and Simplified Acute Physiological (SAPS) II score, however these are rarely calculated on a daily basis in a routine manner due to the relatively high complexity and time resource requirements associated with each score. The use of novel biomarkers can satisfy this unmet clinical need, however few, if any, have successfully made it into widespread clinical routine (8).

Of these biomarkers, mid-regional pro-adrenomedullin (MR-proADM)—a peptide generated by multiple tissues in order to stabilise the microcirculation and protect against endothelial permeability and consequent organ failure (9-16)—has shown considerable promise, especially in the fields of sepsis (17), lower respiratory tract infections (18-21), lung transplantation (22), thoracic surgery (23) and hypervolemia (WO2017/89474). Indeed, the endothelium and microcirculation is widely acknowledged to play a significant role in the pathophysiological host response to sepsis (24, 25), with the regulation and distribution of blood flow within each organ of major importance (25), and may therefore provide an alternative indication as to the severity of the general host response, compared to scores of individual organ dysfunction.

Understanding the host response to sepsis is crucial in order to initiate appropriate treatment strategies. One fundamental factor is understanding the processes behind developing organ dysfunction. Each organ system is made up of a complex and vast network of capillaries, arterioles and venules, which is termed the microvascular system. Particularly during inflammatory responses platelets can have harmful effects on vascular integrity which can for example lead to an increased vascular barrier permeability (59). However specific organs have varying degrees microvascular density and complexity, with the microcirculation playing different roles depending on specific organ.

The contribution of blood platelets to sepsis pathophysiology and organ failure has been the subject of renewed attention. Using common platelet count thresholds, thrombocytopenia (an abnormally low level of platelets in the blood) accounts for 20-50% of patients in the ICU, and is associated with poor outcomes (38-47). Platelets are well known players in coagulation and likely contribute to disseminated intravascular coagulation (DIC), as well as being essential factors of the immune response, reacting to infection and disturbed tissue integrity and contributing to inflammation, pathogen killing and tissue repair (48-53). Furthermore, the role of platelets and thrombocytopenia in the context of existing and developing critical illness, such as sepsis and organ failure, is a topic of intense research (54-57).

Under healthy vascular conditions, platelets encounter inhibitory signals generated from endothelial cells that prevent their activation. They circulate in close proximity to vessel walls and disruption in the endothelial cell lining overcomes these inhibitory signals and drives platelet adherence, activation and aggregation, which temporarily plug the damaged vessel.

Activated platelets secrete a profusion of pro-inflammatory material and cytokines, which target endothelial cells and leucocytes. In normal conditions, the endothelium is a non-adhesive surface, however when activated by platelets it undergoes profound changes which include the expression of cell adhesion molecules and tissue factors. Platelets adhere to the activated endothelial cells following a multi-step process in which glycans play a critical role. Platelet activation can further alter vascular tone and lead to structural changes, thereby increasing vascular permeability. The formation of platelet aggregates in blood is an early phenomenon in sepsis progression.

Understanding developing organ dysfunction, as indicated by the sequential organ failure assessment score, is therefore crucial to helping develop personalised sepsis treatments. An early warning of increasing or decreasing SOFA scores at the earliest moments following sepsis diagnosis, is critical. However, so far there are no reliable diagnostic and/or prognostic markers available that indicate a to be expected increasing or decreasing SOFA score and/or the presence or development of abnormal platelet levels, disseminated intravascular coagulation (DIC) and/or associated organ failure, in particular specific organ failure.

Especially for critically ill patients, the management of thrombocytopenia can be challenging since different mechanisms can lead to a significant low platelet number: hemodilution (infusion of fluids), increased platelet consumption (e.g. due to DIC, hemophagocytosis, thrombosis), increased platelet destruction (e.g. due to platelet autoantibodies, heparin, drugs), decreased platelet production (e.g. due to bacterial toxins, drugs, chronic liver disease) or increased platelet sequestration (e.g. due to hypersplenism, hypothermia). Furthermore a low platelet count could be insignificant and non-pathological due to seasonal and individual variations (58). In addition different scenarios cause a thrombocytopenic phenotype without being pathologically relevant (pseudothrombocytopenia). Clotting in a blood sample or EDTA-induced ex vivo platelet clumping can be reasons for pseudothrombocytopenia and could mislead therapeutic measures such as platelet transfusion.

Therefore, there is an urgent need for the development of diagnostic and prognostic tools and methods that indicate an abnormal development of the platelet level, and the associated severity of an abnormal platelet level.

SUMMARY OF THE INVENTION

In light of the difficulties in the prior art, the technical problem underlying the present invention is the provision of means for determining abnormal platelet levels in a subject. One object of the invention may be considered providing means for the diagnosis, prognosis, treatment guidance, treatment monitoring, risk assessment and/or risk stratification of a present or subsequent adverse event associated with abnormal platelet levels, such as organ failure, specific organ failure and/or death in in a patient. One object of the invention is therefore providing one or more biomarkers or combinations of biomarkers to identify patients who have a high risk of such an adverse event.

The solution to the technical problem of the invention is provided in the independent claims. Preferred embodiments of the invention are provided in the dependent claims.

The method therefore relates to a method for determining, diagnosis, prognosis, treatment guidance, treatment monitoring, risk assessment and/or risk stratification of abnormal platelet levels in a patient, comprising
  a. providing a sample of said patient,
  b. determining a level of proadrenomedullin (proADM) or fragment(s) thereof in said sample,
  c. wherein said level of proADM or fragment(s) thereof correlates with the abnormal platelet levels in said patient.

The invention also relates to a method for the diagnosis, prognosis, treatment guidance, treatment monitoring, risk assessment and/or risk stratification of thrombocytopenia and/or associated medical conditions, such as for example disseminated intravascular coagulation (DIC) or organ dysregulation or organ failure based on a level of proadrenomedullin (proADM) or fragment(s) thereof in said sample. The invention therefore relates to a method for the diagnosis, prognosis, risk assessment and/or risk stratification of thrombocytopenia and/or disseminated intravascular coagulation (DIC) based on a level of proadrenomedullin (proADM) or fragment(s) thereof in said sample.

The present invention is based on the surprising finding that the level of proADM and in particular MR-proADM in a sample of a patient correlates with the platelet count of said patient at the moment of sample isolation. Even more surprising, it was found that an increasing level of proADM correlates with decreasing thrombocyte numbers. These correlations persist with time, such that increasing proADM values at day 1 and day 4 after baseline measurement, correlate with lowering platelet levels, and eventual mortality.

In some embodiments, the likelihood of the occurrence of a subsequent adverse event, such as failure of the coagulation system, abnormal platelet levels, DIC and/or thrombocytopenia, can be assessed on the comparison of the level of proADM or fragments thereof in the sample in comparison to a reference level (such as a threshold or cut-off value and/or a population average), wherein the reference level may correspond to proADM or fragments thereof in healthy patients, or in patients who have been diagnosed as critically ill, if applicable.

However, there is a need in the art to develop personalised treatment strategies that are formulated on an organ by organ basis. Accordingly, it is a great advantage of the method of the present invention that it is possible to predict with a high likelihood a specific organ failure that may develop in the near future, in particular for the kidney, liver and the coagulation system on the basis of a level of proADM determined at time point 0 (day 0). The examples provided herein demonstrate that MR-proADM can significantly better predict improvements or deteriorations with respect to an adverse event, such as preferably improvements or deteriorations in the coagulation, nephrotic and hepatic organ systems.

Accordingly, the method of the present invention can help to predict the likelihood of a subsequent adverse event in the health of the patient, such as failure of the coagulation system, abnormal platelet levels, DIC and/or thrombocytopenia. This means, that the method of the invention can discriminate high risk patients, who are more likely to suffer from complications, or whose state will become more critical in the future, from low risk patients, whose health state is stable or even improving, so that it is not expected that they will suffer from an adverse event, such as failure of the coagulation system, abnormal platelet levels, death, DIC and/or thrombocytopenia, which might require certain therapeutic measures and/or more intense monitoring of the patient.

The method also relates to a method for assessing the severity of low platelet levels or associated conditions, such as thrombocytopenia and/or disseminated intravascular coagulation (DIC). ProADM can be used in a quantitative or semi-quantitative manner to assess the likelihood of severity or severity of an existing condition.

The invention therefore relates to a method for determining, diagnosis, prognosis, treatment guidance, treatment monitoring, risk assessment and/or risk stratification of a present, or subsequent, adverse event in the health of a patient, comprising providing a sample of said patient, determining a level of adrenomedullin (ADM) or fragment(s) thereof in said sample, wherein said level of proADM or fragment(s) thereof correlates with the likelihood of a subsequent adverse event in the health of said patient.

In embodiments of the invention, the subsequent adverse event is organ failure, specific organ failure, death, death within 28-90 days from the time point of isolating the sample, abnormal platelet levels, thrombocytopenia, disseminated intravascular coagulation (DIC) and/or liver failure or an infection.

In preferred embodiments, the invention relates to a method for determining, diagnosis, prognosis, treatment guidance, treatment monitoring, risk assessment and/or risk stratification of specific organ failure in a patient, comprising providing a sample of said patient, determining a level of pro-adrenomedullin (proADM) or fragment(s) thereof in said sample, wherein said level of proADM or fragment(s) thereof correlates with the failure of a specific organ in said patient.

In preferred embodiments, the invention relates to a method for determining, diagnosis, prognosis, treatment guidance, treatment monitoring, risk assessment and/or risk stratification of liver failure in a patient, comprising providing a sample of said patient, determining a level of pro-adrenomedullin (proADM) or fragment(s) thereof in said sample, wherein said level of proADM or fragment(s) thereof correlates with the failure of the liver in said patient.

In some embodiments, the method for determining, diagnosis, prognosis, treatment guidance, treatment monitoring, risk assessment and/or risk stratification of specific organ failure in a patient is carried out in a patient with or suspected of having low platelet levels, or a related condition.

The term "specific organ failure" refers to the failure of a specific organ. For example, in case of a method of prognosis, the method of the invention can be used for prognosing failure not only of failure of any organ, but of a specific organ. For example, the method can be used to specifically prognose the failure of the kidney, liver and/or the blood coagulation system.

Herein, failure of an organ or a system, such as the liver or the coagulation system, can relate to both, total breakdown of the system, in the sense of the absence or almost absence of any physiological function of the organ or system, and dysregulation, which refers to an imbalance of the homeostasis of an organ or a system. A mild dysregulation may occur without initial clinical symptoms, whereas a progressive dysregulation may lead to a partial loss of function of the system leading to clinical symptoms and a strong dysregulation may be equivalent to a breakdown.

The invention therefore relates to a method for the prognosis, risk assessment and/or risk stratification of low platelet levels and/or thrombocytopenia and/or disseminated intravascular coagulation (DIC) in a patient, wherein a level of proADM or fragment(s) thereof equal to or above a high severity level (or cut-off value) is indicative of the likelihood of developing low platelet levels and/or thrombocytopenia and/or DIC within 12 hours to 120 hours, preferably within 24 hours to 72 hours, after obtaining a sample.

A particular advantage of the method of the present invention is that a patient who has been identified as a low risk patient by means of the method of the present invention could be more rapidly discharged, for example form an ICU, an emergency department, a private practice or a hospital. Also, for low risk patients, the intensity and/or frequency of the observation of the health status of the patient could be decreased. Accordingly, the hospital or other medical institution in charge of the patient could more efficiently decide which patients require intensive medical care and observation. Consequently, the respective hospital or institution could, for example, more efficiently occupy ICU beds with high-risk patients. This would lead to an improved medical care for the high-risk patients, since the medical personnel could focus on such patients, while low risk patients could be discharged. This would also lead to significant benefits from avoided costs for unnecessary measures that would otherwise be applied to low risk patients.

It was entirely surprising that the level of proADM or fragments thereof in a sample from the patient can provide critical information about the likelihood of the occurrence or presence and severity of, for example, abnormal platelet levels associated with DIC and/or thrombocytopenia or thrombocytopenia secondary to sepsis.

The use of proADM or fragments thereof as a single parameter in embodiments of the present invention is advantageous over the use of other single parameters, such as biomarkers or clinical scores, since proADM is more precise in the prediction of failure of the coagulation system, abnormal platelet levels, DIC and/or thrombocytopenia as compared to other markers and clinical parameters such as platelet count, lactate or clinical scores such as SOFA, qSOFA, SAPS II or APACHE II.

In embodiments of the invention the patient showing symptoms or no symptoms of any physiological disorder can be examined at any medical setting. According to a preferred embodiment, the sample is isolated from a patient during a medical examination.

In embodiments of the invention, the patient is being or has been diagnosed as being critically ill. According to a further embodiment, the sample is isolated from the patient at or after the time point of diagnosis. Furthermore, in embodiments of the method of the invention medical treatment has been initiated at or before the time point of diagnosis. In embodiments, the patient has been diagnosed as being critically ill and medical treatment has been initiated. The sample may be isolated from the patient before, at or after diagnosis and treatment initiation.

In one embodiment, the patient is, or has been diagnosed as, critically ill.

In one embodiment, the sample is isolated from the patient at or after the time point of diagnosis as being critically ill.

In one embodiment, the patient is diagnosed with an infectious disease.

In one embodiment, the patient is diagnosed with sepsis, severe sepsis or septic shock.

In one embodiment, the patient is diagnosed with one or more existing organ failure(s), and/or is a posttraumatic or postsurgical patient In one embodiment, the patient is diagnosed with a dysregulation of the coagulation system, such as disseminated intravascular coagulation (DIC) or thrombocytopenia, and/or with a dysfunction of an organ associated with the coagulation system, such as blood vessels, spleen, bone marrow and/or the immune system.

According to a further embodiment, the patient is being or has been diagnosed as suffering from disseminated intravascular coagulation (DIC).

DIC can be regarded as a syndrome that can occur in the context of different types of diseases, such as for example solid tumors, blood cancer, lymphoma, leukemia, obstetric complications (such as (pre)eclampsia, abruptio placentae, amniotic fluid embolism, abortion), massive injuries (such as severe trauma, burns, hyperthermia, extensive surgery), sepsis, severe sepsis, septic shock, severe infections (for example bacterial, viral, fungal, protozoan, superinfection/co-infection(s)), transfusion reactions (such as AOB incompatibility hemolytic reactions), adverse drug reactions (e.g. induced by antiinfectives, antineoplastic agents, antithrombotic agents), severe allergic or toxic reactions or giant hemangiomas.

The skilled person is aware of further conditions and diseases that can be associated DIC. DIC can lead to (multi) organ dysfunction/damage (independently if the problem came from bleeding or clotting (depending on the "DIC stage"). A combination of widespread loss of tissue blood flow and simultaneous bleeding leads to an increased risk of death. Therefore DIC is a medical emergency that can be associated with severe complications. The earlier the prediction or diagnosis of DIC the better is the prognosis of the patient.

Several treatments have been suggested for DIC, such as Factor V, Factor XIII-AP, shingosine-1-phosphate (S1P), thombomodulin, antibodies against tissue factor or tissue factor pre-mRNA splicing, reactive nitrogen inhibiting peptide (RNIP) fragment, TAFIa(i), procoagulant phospholipid, as well as thrombin inhibitor.

In embodiments of the invention, the DIC can lead to (multi) organ dysfunction/damage (independently if the problem came from bleeding or clotting (depending on the "DIC stage"). A combination of widespread loss of tissue blood flow and simultaneous bleeding leads to an increased risk of death.

In embodiments of the invention, the patient receives a treatment of DIC, such as, for example, Factor V, Factor XIII-AP, shingosine-1-phosphate (S1P), thombomodulin, antibodies against tissue factor or tissue factor pre-mRNA splicing, reactive nitrogen inhibiting peptide (RNIP) fragment, TAFIa(i), Procoagulant Phospholipid, and/or thrombin inhibitor.

In further embodiments, the treatment received by the patient comprises one or more of antibiotic treatment, invasive mechanical ventilation, non-invasive mechanical ventilation, renal replacement therapy, vasopressor use, fluid therapy, corticosteroids, blood or platelet transfusion, splenectomy, direct thrombin inhibitors (such as lepirudin or argatroban), blood thinners (such as bivalirudin and fondaparinux), discontinuation of heparin in case of heparin-induced thrombocytopenia, lithium carbonate, folate, extracorporal blood purification and/or organ protection.

In preferred embodiments of the invention, said level of proADM inversely correlates with the platelet level.

Preferably the sample can be a bodily fluid. More preferably, the sample is selected from the group consisting of a blood sample, a serum sample, a plasma sample and/or a urine sample.

Preferably, the method is carried out in some embodiments by determining a level of proADM or fragment(s) thereof, wherein said determining of proADM comprises determining a level of MR-proADM in the sample. The employment of determining MR-proADM is preferred for any given embodiment described herein and may be considered in the context of each embodiment, accordingly. In preferred embodiments the "ADM fragment" may be considered to be MR-proADM. In some embodiments, any fragment or precursor of ADM, such pre-pro-ADM, pro-ADM, the peptide known as ADM itself, or fragments thereof, such as MR-proADM, may be employed.

According to another embodiment of the invention, determining a level of proADM or fragment(s) thereof comprises determining a level of MR-proADM in the sample.

In a preferred embodiment of the method of the invention,
a level of proADM or fragment(s) thereof below a high severity level (cut-off value) is indicative of normal or high platelet levels, or
a level of proADM or fragment(s) thereof equal or above a high severity level (or cut-off value) is indicative of the presence of, or likelihood of developing, low platelet levels and/or thrombocytopenia and/or disseminated intravascular coagulation (DIC),
wherein a high severity level (or cut-off value) of proADM or fragments thereof is a level above 6.5 nmol/l, 6.95 nmol/l, or preferably 10.9 nmol/l.

According to the present invention, the term "indicate" in the context of "indicative of a subsequent adverse event" and "indicative of the absence of a subsequent adverse event" is intended as a measure of risk and/or likelihood. Preferably, the "indication" of the presence or absence of an adverse event is intended as a risk assessment, and is typically not to be construed in a limiting fashion as to point definitively to the absolute presence or absence of said event.

Therefore, the term "indicative of the absence of a subsequent adverse event" or "indicative of a subsequent adverse event" can be understood as indicating a low or high risk of the occurrence of an adverse event, respectively. In some embodiments a low risk relates to a lower risk compared to proADM levels detected above the indicated values. In some embodiments a high risk relates to a higher risk compared to proADM levels detected below the indicated values.

Keeping the above in mind, the determination of high and/or low severity levels of proADM is however very reliable with respect to determining the presence or absence of a subsequent adverse event when using the cut-off values disclosed herein, such that the estimation of risk enables an appropriate action by a medical professional.

In some embodiments, the low or intermediate or high severity level of proADM indicates the severity of a physical condition of a patient with regard to an adverse event.

In some embodiments, the low or intermediate or high severity level of proADM indicates the severity of a physical condition of a patient with thrombocytopenia or symptoms of thrombocytopenia.

In some embodiments, the low or intermediate or high severity level of proADM indicates the severity of a physical condition of a patient with thrombocytopenia or symptoms of thrombocytopenia secondary to sepsis.

It was entirely surprising that a level of proADM or fragments thereof could be correlated with the likelihood of the presence or absence of a subsequent adverse event, such as failure of the coagulation system, abnormal platelet levels, DIC and/or thrombocytopenia, also in the context of critically ill patients who were receiving treatments at these time points.

ProADM levels in samples can preferably be assigned to 3 different severity levels of proADM. High levels of proADM indicate a high severity level, intermediate levels indicate an intermediate severity level and low levels indicate a low severity levels. The respective concentrations that determine the cut-off values for the respective severity levels depend on multiple parameters such as the time point of sample isolation, for example after prognosis, diagnosis and treatment initiation of the patient, and the method used for determining the level of proADM or fragments thereof in said sample.

The cut-off values disclosed herein refer preferably to measurements of the protein level of proADM or fragments thereof in a plasma sample obtained from a patient by means of the BRAHMS MR proADM KRYPTOR assay. Accordingly, the values disclosed herein may vary to some extent depending on the detection/measurement method employed, and the specific values disclosed herein are intended to also read on the corresponding values determined by other methods.

In one embodiment of the invention, a low and/or intermediate severity level of proADM or fragment(s) thereof is indicative of the absence of a (subsequent) adverse event, such as failure of the coagulation system, abnormal platelet levels, DIC and/or thrombocytopenia, wherein the low severity level is below a cut-off value in the range of 1.5 nmol/l and 4 nmol/l. Any value within these ranges may be considered as an appropriate cut-off value for a low severity levels of proADM or fragments thereof. For example, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0 nmol/l.

In one embodiment of the invention, a high severity level of proADM or fragment(s) thereof is indicative of a (subsequent) adverse event, such as failure of the coagulation system, abnormal platelet levels, DIC and/or thrombocytopenia, wherein the high severity level is above a cut-off value in the range of 6.5 nmol/l to 12 nmol/l. Any value within these ranges may be considered as an appropriate cut-off value for a high severity levels of proADM or fragments thereof. For example, 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45, 7.5, 7.55, 7.6, 7.65, 7.7, 7.75, 7.8, 7.85, 7.9, 7.95, 8.0, 8.05, 8.1, 8.15, 8.2, 8.25, 8.3, 8.35, 8.4, 8.45, 8.5, 8.55, 8.6, 8.65, 8.7, 8.75, 8.8, 8.85, 8.9, 8.95, 9.0, 9.05, 9.1, 9.15, 9.2, 9.25, 9.3, 9.35, 9.4, 9.45, 9.5, 9.55, 9.6, 9.65, 9.7, 9.75, 9.8, 9.85, 9.9, 9.95, 10.0, 10.05, 10.1, 10.15, 10.2, 10.25, 10.3, 10.35, 10.4, 10.45, 10.5, 10.55, 10.6, 10.65, 10.7, 10.75, 10.8, 10.85, 10.9, 10.95, 11.0, 11.05, 11.1, 11.15, 11.2, 11.25, 11.3, 11.35, 11.4, 11.45, 11.5, 11.55, 11.6, 11.65, 11.7, 11.75, 11.8, 11.85, 11.9, 11.95, 12.0 nmol/l.

All cut-off values disclosed herein relating to the level of a marker or biomarker, such as proADM or PCT, are to be understood as "equal or above" a certain cut-off or "equal or below" a certain cut-off. For example, an embodiment relating to a level of proADM or fragment(s) thereof below 4 nmol/l, preferably below 3 nmol/l, more preferably below 2.7 nmol/l is to be understood as relating to a level of proADM or fragment(s) thereof equal or below 4 nmol/l, preferably equal or below 3 nmol/l, more preferably equal or below 2.7 nmol/l. Conversely, an embodiment relating to a level of proADM or fragment(s) thereof above 6.5 nmol/l, preferably above 6.95 nmol/l, more preferably above 10.9 nmol/l is to be understood as relating to a level of proADM or fragment(s) thereof equal or above 6.5 nmol/l, preferably equal or above 6.95 nmol/l, more preferably equal or above 10.9 nmol/l.

In other embodiments described herein, the severity levels are defined preferably by cut-off values, that represent boundaries between low, intermediate or high severity levels. Any embodiments that present cut-offs therefore may use the format of a single cut-off value as a boundary between two severity levels, or a single cutoff level for each severity level.

In some embodiments, the proADM cut-off value between low and intermediate severity levels is:
2.75 nmol/l±20%, or 2.75 nmol/l±15%, or ±12%, ±10%, ±8%, or ±5%,
and between intermediate and high severity levels:
10.9 nmol/l±20%, or 10.9 nmol/l±15%, or ±12%, ±10%, ±8%, or ±5%.

These cut-off values are preferably relevant for an assessment of proADM severity level at baseline, in other words upon diagnosis and/or therapy begin and/or hospitalization. The baseline levels themselves, through e.g. a single measurement or measurements taken at an initial single time point, are able to indicate fluid therapy prescription.

In some embodiments, the proADM cut-off value between low and intermediate severity levels is:
2.80 nmol/l±20%, or 2.80 nmol/l±15%, or ±12%, ±10%, ±8%, or ±5%,
and between intermediate and high severity levels:
9.5 nmol/l±20%, or 9.5 nmol/l±15%, or ±12%, ±10%, ±8%, or ±5%.

These cut-off values are preferably relevant for an assessment of proADM severity level after 1 day, in other words approx. 24 hours after baseline, in other words, approx. 1 day after diagnosis and/or therapy begin and/or hospitalization. For example, in embodiments where the proADM is measured one day after therapy begin, the cut-off values for day 1 may be employed. As is evident from the above, the cutoff between intermediate and high is somewhat lower than at baseline, i.e. as time progresses, even somewhat lower (but still relatively high) levels are associated with high risk and are classed in the high severity level.

In some embodiments, the proADM cut-off value between low and intermediate severity levels is:
2.80 nmol/l±20% or 2.80 nmol/l±15%, or ±12%, ±10%, ±8%, or ±5%,
and between intermediate and high severity levels:
7.7 nmol/l±20% or 7.7 nmol/l±15%, or ±12%, ±10%, ±8%, or ±5%.

These cut-off values are preferably relevant for an assessment of proADM severity level after 4 days, in other words approx. 4 days after baseline, in other words, approx. 4 days after diagnosis and/or therapy begin and/or hospitalization. For example, in embodiments where the proADM is measured 4 days after therapy begin, the cut-off values for day 4 may be employed. As is evident from the above, the cutoff between intermediate and high is somewhat lower than at baseline or at day 1, i.e. as time progresses, even somewhat lower (but still relatively high) levels are associated with high risk and are classed in the high severity level.

In some embodiments, the cutoff levels to be employed in the embodiments described above may be adjusted according to an appropriate level depending on the day the measurement is made. Each of the cut-off values is subject to some variation due to common variance as may be expected by the skilled person. The relevant cut-off levels are determined based on extensive data, as presented below, but are not intended in all possible embodiments to be final or exact values. By using a similar cut-off to those recited, i.e. within the ±20%, ±15%, ±12%, ±10%, ±8%, or ±5%, as can be determined by a skilled person, similar results may be expected.

Any embodiment reciting ±20% of a given cut-off value, may be considered to also disclose ±15%, ±12%, ±10%, ±8%, or ±5%.

Any embodiment reciting a particular cut-off value for baseline, day 1 or day 4, may be considered to also disclose the corresponding cut-off values for the other days, e.g. an embodiment reciting a baseline cut-off value may be considered to also relate to the same embodiment reciting the day 1 or day 4 cut-off value.

Cut-off values apply in preferred embodiments to blood samples, or sample derived from blood, but are not limited thereto.

In embodiments of the invention, the level of proADM or fragment(s) thereof equal or above the high severity level (cut-off value) indicates initiating or modifying a treatment of the patient, such as provision of corticosteroids, blood or platelet transfusion, transfusion of blood components, such as serum, plasma or specific cells or combinations thereof, drugs promoting the formation of thrombocytes, causative treatment or preforming a splenectomy. Preferably, the cause of the dysregulation of the coagulation system may be identified and treated (causative treatment).

According to another embodiment, the patients are intensive care unit (ICU)-patients, wherein
the level of proADM or fragment(s) thereof below the low severity level (cut-off value) indicates discharging of said patient from ICU, or
the level of proADM or fragment(s) thereof equal or above the high severity level (cut-off value) indicates modifying the treatment of the patient in the ICU.

It is a particular advantage of the present invention that based on the classification of the determined levels of proADM or fragments thereof it is possible to assess the probability of the occurrence of a future adverse event in the health of the patient. Based on this assessment it is possible to adjust the next treatment options and decisions.

A treatment modification in the sense of the present invention would include, without limitation, an adjustment of the dose or administration regime of the ongoing medication, change of the ongoing treatment to a different treatment, addition of a further treatment option to the ongoing treatment or stop of an ongoing treatment or the identification and treatment of the cause of the dysfunction. Different treatments that can be applied to patients in the context of the present invention have been disclosed in the detailed description of this patent application.

In preferred embodiments of the invention, the method additionally comprises determining a level of one or more additional markers in a sample isolated from the patient.

The one or more additional marker may be determined in the same or a different sample from said patient. In case of a different sample, the sample may be isolated at the same time, before or after isolation of the sample for determining proADM or fragment(s) thereof. Irrespective of whether the one or more additional marker is determined in the same or a different sample, the measurement may occur in parallel, simultaneously, before and/or after the measurement of proADM.

In a preferred embodiment, the one or more additional markers comprise the level of platelets in a blood sample.

In one embodiment, the one or more additional markers comprises PCT or fragment(s) thereof.

It is particularly advantageous to combine the determination of proADM or fragments thereof with the determination of platelet levels in a sample, wherein the sample used for determining proADM may be the same or a different sample used for conducting the platelet count.

According to a further preferred embodiment of the present invention, the method described herein comprises additionally
- determining a level of platelets in a sample isolated from the patient, or
- determining a level of platelets in a first sample isolated from the patient, wherein said first sample is isolated before, at or after the time point of diagnosis and treatment initiation,
- determining a level of platelets in a second sample isolated from said patient, wherein the second sample has been isolated after the first sample, preferably within 30 minutes after isolation of the first sample or 30 minutes, 1 hour, 2 hours, 6 hours, 12 hours, 24 hours, 4 days, 7 or 10 days after isolation of the first sample, and
- determining a difference in the level of platelets in the second sample in comparison to the level of platelets in the first sample.

In further embodiments, the one or more additional markers comprise one or more markers for a dysregulation of the coagulation system, such as disseminated intravascular coagulation (DIC) or thrombocytopenia, comprising membrane microparticle, platelet count, mean platelet volume (MPV) sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay. In embodiments, the additional one or more markers comprise one or more histones.

In embodiments of the invention, proADM is determined in the context of a method for therapeutic guidance in patients with heparin administration to predict thrombocytopenia, e.g. adaption/change of the medication until the patient shows normal platelet counts and/or proADM levels are below a cut-off disclosed herein.

In embodiments of the invention, proADM is determined in the context of a method for therapeutic guidance in patients with antimicrobial treatment to predict leukocytopenia, e.g. adaption/change of the medication until the patient shows normal platelet counts and/or proADM levels are below a cut-off value disclosed herein.

In further embodiments, PCT is included in the monitoring, e.g. for the purpose of antibiotic stewardship and/or prevention of misuse of antibiotics and/or prevention of side effects, for example to lower the risk of getting thrombocytopenia or DIC. In this context, platelet counts may be determined as an additional marker.

In embodiments of the invention, proADM is determined in the context of platelet transfusion. In further embodiments, PCT is included in the monitoring, e.g. for the detection of a bacterial infection, for the purpose of antibiotic stewardship and/or prevention of misuse of antibiotics and/or prevention of side effects, for example to lower the risk of getting thrombocytopenia or DIC. In this context, platelet counts may be determined as an additional marker.

In embodiments of the invention, proADM is determined in the context of a method for the prediction and/or diagnosis of dysregulation of the coagulation system, DIC and/or thrombocytopenia in a patient, for example a shock patient or a septic shock patient, wherein preferably PCT is determined as an additional marker.

In embodiments of the invention, the absolute immature platelet count (AIPC) may be determined as an additional marker.

In embodiments of the invention, proADM is a better marker than platelet counts for the prediction of getting DIC or thrombocytopenia. In embodiments, a treatment may be fluid management.

In embodiments, patients with acute kidney injury (AKT)+/−continuous renal replacement therapy (CRRT), community acquired pneumonia (CAP), sepsis and ICU-patients in general with a higher proADM have a higher risk of mortality.

In one embodiment the invention additionally comprises informing the patient of the results of the method described herein.

In one embodiment, the method enables prognosis, risk assessment or risk stratification of an adverse event in a patient with an abnormal platelet level, comprising:
  a. providing a sample of said patient,
  b. determining a level of proadrenomedullin (proADM) or fragment(s) thereof in said sample,
  c. wherein said level of proADM or fragment(s) thereof correlates with the abnormal platelet levels and with the likelihood of an adverse event occurring in said patient.

In one embodiment, the adverse event is one or more of mortality, sepsis-related mortality, organ failure and/or organ dysfunction.

In one embodiment, the organ failure or organ dysfunction is associated with thrombocytopenia.

In one embodiment, the at least one additional marker or clinical parameter is measured, preferably selected from the group consisting of procalcitonin, Histone 3, Histone 2A, Histone 2B, Histone 4 or fragment(s) thereof, platelet count, mean platelet volume and/or one or more markers for a dysregulation of the coagulation system.

In one embodiment, the patient shows symptoms of an infectious disease or sepsis, or is diagnosed with an infectious disease and/or one or more existing organ failure(s), or has been diagnosed as suffering from sepsis, severe sepsis or septic shock.

In a further embodiment, the method enables determining, diagnosis, prognosis, treatment guidance, treatment monitoring, risk assessment and/or risk stratification of septic thrombocytopenia in a patient, comprising
  a. providing a sample of said patient,
  b. determining a level of proadrenomedullin (proADM) or fragment(s) thereof in said sample, and
  c. determining a level of procalcitonin (PCT) or fragment(s) thereof in said sample,
  d. wherein when a level of procalcitonin (PCT) or fragment(s) thereof of is ≥0.5 ng/ml it indicates the presence of, or increased risk of acquiring, sepsis, and wherein when a proADM level or fragment(s) thereof of is ≥2.75 nmol/L it indicates the presence of, or increased risk of acquiring, thrombocytopenia.

This embodiment enables a combination of beneficial functions not previously derivable from the art that enables practitioners to identify not only the presence of septic disease, but also to initiate directed treatment towards improving platelet levels. Elevated levels of PCT or fragments thereof indicate the presence of infectious disease, in particular sepsis, using known values established in the art. The combination with measuring ADM, indicating platelet levels, followed preferably by appropriate platelet or thrombocyte improving measures, provides practitioners with an leap on underlying pathological process in sepsis, allowing improved, faster treatment.

The invention further relates to a kit for carrying out the method described herein, comprising:
  a. detection reagents for determining the level proADM or fragment(s) thereof, and optionally additionally for determining the level of PCT or fragment(s) thereof and/or one or more additional markers as described herein, in a sample from a subject, and
  b. reference data, such as a reference level, corresponding to high severity levels of proADM, wherein the high severity level is above 6.5 nmol/l, preferably above 6.95 nmol/l, more preferably above 10.9 nmol/l, and optionally PCT levels and/or levels of one or more additional markers as described herein, wherein said reference data is stored on a computer readable medium and/or employed in the form of computer executable code configured for comparing the determined levels of proADM or fragment(s) thereof, and optionally additionally the determined levels of PCT or fragment(s) thereof and/or additional markers as described herein, to said reference data.

In some embodiments the kit comprises additionally therapeutic agents for improving platelet levels, as described in more detail herein.

The detection reagents for determining the level of proADM or fragment(s) thereof, and optionally for determining the level of PCT or fragment(s) thereof and/or additional markers of the invention, are preferably selected from those necessary to perform the method, for example antibodies directed to proADM, suitable labels, such as fluorescent labels, preferably two separate fluorescent labels suitable for application in the BRAHMS KRYPTOR assay, sample collection tubes.

In one embodiment of the method described herein the level of proADM or fragment(s) thereof and optionally additionally other biomarkers such as for example PCT or fragment(s) thereof is determined using a method selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

The method according to the present invention can furthermore be embodied as a homogeneous method, wherein the sandwich complexes formed by the antibody/antibodies and the marker, e.g., the proADM or a fragment thereof, which is to be detected remains suspended in the liquid phase. In this case it is preferred, that when two antibodies are used, both antibodies are labelled with parts of a detection system, which leads to generation of a signal or triggering of a signal if both antibodies are integrated into a single sandwich.

Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733 A, EP-B1 0 180 492 or EP-B1 0 539 477 and the prior art cited therein. In this way, measurements in which only reaction products comprising both labelling components in a single immune-complex directly in the reaction mixture are detected, become possible.

For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of the proADM protein or a fragment thereof, and/or the level of any further marker of the herein provided method are determined. In particular preferred aspects, the diagnostic device is KRYPTOR®.

In one embodiment of the method described herein the method is an immunoassay and wherein the assay is performed in homogeneous phase or in heterogeneous phase.

In further embodiments of the method described herein, the method additionally comprises a molecular analysis of a sample from said patient for detecting an infection. The sample used for the molecular analysis for detecting an infection preferably is a blood sample or fragment thereof, such as serum, plasma or whole blood. In a preferred embodiment the molecular analysis is a method aiming to detect one or more biomolecules derived from a pathogen. Said one or more biomolecule may be a nucleic acid, protein, sugar, carbohydrates, lipid and or a combination thereof such as glycosylated protein, preferably a nucleic acid. Said biomolecule preferably is specific for one or more pathogen(s). According to preferred embodiments, such biomolecules are detected by one or more methods for analysis of biomolecules selected from the group comprising nucleic acid amplification methods such as PCR, qPCR, RT-PCR, qRT-PCR, high-throughput sequencing (such as NGS) or isothermal amplification, mass spectrometry, detection of enzymatic activity and immunoassay based detection methods. Further methods of molecular analysis are known to the person skilled in the art and are comprised by the method of the present invention.

In one embodiment of the method described herein a first antibody and a second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said proADM or fragments thereof to be detected, a measurable signal which permits detection of the resulting sandwich complexes in the measuring solution is generated.

In one embodiment of the method described herein the labelling system comprises a rare earth cryptate or chelate in combination with a fluorescent or chemiluminescent dye, in particular of the cyanine type.

In one embodiment of the method described herein, the method additionally comprises comparing the determined level of proADM or fragment(s) thereof to a reference level, threshold value and/or a population average corresponding to proADM or fragments thereof in patients who have been diagnosed as being critically ill and are under medical treatment or who are at risk of getting or having a dyregulated coagulation system, wherein said comparing is carried out in a computer processor using computer executable code.

The methods of the present invention may in part be computer-implemented. For example, the step of comparing the detected level of a marker, e.g. the proADM or fragments thereof, with a reference level can be performed in a computer system. In the computer-system, the determined level of the marker(s) can be combined with other marker levels and/or parameters of the subject in order to calculate a score, which is indicative for the diagnosis, prognosis, risk assessment and/or risk stratification, treatment guidance and patient management. For example, the determined values may be entered (either manually by a health professional or automatically from the device(s) in which the respective marker level(s) has/have been determined) into the computer-system. The computer-system can be directly at the point-of-care (e.g. primary care, ICU or ED) or it can be at a remote location connected via a computer network (e.g. via the internet, or specialized medical cloud-systems, optionally combinable with other IT-systems or platforms such as hospital information systems (HIS)). Typically, the computer-system will store the values (e.g. marker level or parameters such as age, blood pressure, weight, sex, etc. or clinical scoring systems such as SOFA, qSOFA, BMI, PCT, platelet counts, etc.) on a computer-readable medium and calculate the score based-on pre-defined and/or pre-stored reference levels or reference values. The resulting score will be displayed and/or printed for the user (typically a health professional such as a physician). Alternatively or in addition, the associated prognosis, diagnosis, assessment, treatment guidance, patient management guidance or stratification will be displayed and/or printed for the user (typically a health professional such as a physician or nurse).

In one embodiment of the invention, a software system can be employed, in which a machine learning algorithm is evident, preferably to identify hospitalized patients at risk for sepsis, severe sepsis and septic shock using data from electronic health records (EHRs). A machine learning approach can be trained on a random forest classifier using EHR data (such as labs, biomarker expression, vitals, and demographics) from patients. Machine learning is a type of artificial intelligence that provides computers with the ability to learn complex patterns in data without being explicitly programmed, unlike simpler rule-based systems. Earlier studies have used electronic health record data to trigger alerts to detect clinical deterioration in general. In one embodiment of the invention the processing of proADM levels may be incorporated into appropriate software for comparison to existing data sets, for example proADM levels may also be processed in machine learning software to assist in diagnosing or prognosing the occurrence of an adverse event, dysregulated coagulation such as thrombocytopenia or DIC.

The combined employment of proADM or fragments thereof in combination with another biomarker such as PCT or CRP may be realised either in a single multiplex assay, or in two separate assays conducted on a sample form the patient. The sample may relate to the same sample, or to different samples. The assay employed for the detection and determination of proADM and for example PCT may also be the same or different, for example an immunoassay may be employed for the determination of one of the above markers. More detailed descriptions of suitable assays are provided below.

Cut-off values and other reference levels of proADM or fragments thereof in patients who have been diagnosed as being critically ill and are under treatment or who are at risk of getting or having a dyregulated coagulation system may be determined by previously described methods. For example, methods are known to a skilled person for using the Coefficient of variation in assessing variability of quantitative assays in order to establish reference values and/or cut-offs (George F. Reed et al., Clin Diagn Lab Immunol. 2002; 9(6):1235-1239).

Additionally, functional assay sensitivity can be determined in order to indicate statistically significant values for use as reference levels or cut-offs according to established techniques. Laboratories are capable of independently establishing an assays functional sensitivity by a clinically relevant protocol. "Functional sensitivity" can be considered as the concentration that results in a coefficient of variation (CV) of 20% (or some other predetermined % CV), and is thus a measure of an assays precision at low analyte levels. The CV is therefore a standardization of the standard deviation (SD) that allows comparison of variability estimates regardless of the magnitude of analyte concentration, at least throughout most of the working range of the assay.

Furthermore, methods based on ROC analysis can be used to determine statistically significant differences between two clinical patient groups. Receiver Operating Characteristic (ROC) curves measure the sorting efficiency of the model's fitted probabilities to sort the response levels. ROC curves can also aid in setting criterion points in diagnostic tests. The higher the curve from the diagonal, the better the fit. If the logistic fit has more than two response levels, it produces a generalized ROC curve. In such a plot, there is a curve for each response level, which is the ROC curve of that level versus all other levels. Software capable of enabling this kind of analysis in order to establish suitable reference levels and cut-offs is available, for example the statistics software R (version 3.1.2), JMP 12, JMP 13, Statistical Discovery, from SAS.

Cut off values may similarly be determined for PCT. Literature is available to a skilled person for determining an appropriate cut-off, for example Philipp Schuetz et al. (BMC Medicine. 2011; 9:107) describe that at a cut-off of 0.1 ng/mL, PCT had a very high sensitivity to exclude infection. Terence Chan et al. (Expert Rev. Mol. Diagn. 2011; 11(5), 487.496) described that indicators such as the positive and negative likelihood ratios, which are calculated based on sensitivity and specificity, are also useful for assessing the strength of a diagnostic test. Values are commonly graphed for multiple cut-off values (CVs) as a receiver operating characteristic curve. The area under the curve value is used to determine the best diagnostically relevant CV. This literature describes the variation of CVs (cut-off values, that is dependent on the assay and study design), and suitable methods for determining cut-off values.

Population averages levels of proADM or fragments thereof may also be used as reference values, for example mean proADM population values, whereby patients that are diagnosed as critically ill, such as patient with a dysregulation of the coagulation system, may be compared to a control population, wherein the control group preferably comprises more than 10, 20, 30, 40, 50 or more subjects.

In one embodiment of the invention, the cut-off level for PCT may be a value in the range of 0.01 to 100.00 ng/mL in a serum sample, when using for example a Luminex MAC Pix E-Bioscience Assay or the BRAHMS PCT Kryptor Assay.

In a preferred embodiment the cut-off level of PCT may be in the range of 0.01 to 100, 0.05 to 50, 0.1 to 20, or 0.1 to 2 ng/mL, and most preferably >0.05 to 10 ng/mL. Any value within these ranges may be considered as an appropriate cut-off value. For example, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, 10, 15, 20, 25, 30, 35, 40, 45, 50, 55, 60, 65, 70, 75, 80, 85, 90, 95 or 100 ng/mL may be employed. In some embodiments, PCT levels for healthy subjects are approximately 0.05 ng/mL.

As derived from the one study below, by way of example, the data show that septic patients with abnormal low levels of platelets have a PCT value >7 ng/ml.

The advantages and embodiments of each of the various methods and kits of the invention disclosed herein also apply and read on the respective other methods and kits.

Embodiments of the Invention Relating to Determining a Method for Therapy Monitoring, Comprising the Prognosis, Risk Assessment and/or Risk Stratification of a Subsequent Adverse Event in the Health of a Patient As described above, a subsequent adverse event in some embodiments is one or more of thrombocytopenia, DIC, infection, organ failure, organ dysfunction and/or mortality.

The invention relates to a method for therapy monitoring, comprising the prognosis, risk assessment and/or risk stratification of a subsequent adverse event in the health of a patient, comprising
  providing a sample of said patient, wherein the patient has been diagnosed as being critically ill and/or medical treatment has been initiated, wherein the sample is isolated from the patient after diagnosis and treatment initiation,
  determining a level of proADM or fragment(s) thereof in said sample,
  wherein said level of proADM or fragment(s) thereof correlates with the likelihood of a subsequent adverse event in the health of said patient.

In one embodiment, the patients of the method of the present invention have already been diagnosed as being critically ill and are already receiving treatment. The method of the present invention can therefore be used for monitoring the success of the treatment or therapy that has been initiated, on the basis of determining the likelihood of a subsequent adverse event. The therapy monitoring preferably involves the prognosis of an adverse event and/or the risk stratification or risk assessment of the patient with respect to a future adverse event, wherein this risk assessment and the determination of said risk is to be considered as a means of monitoring the initiated therapy.

Physicians or medical personnel who are treating patients that have been diagnosed as being critically ill can employ the method of the present invention in different clinical settings, such as primary care setting or, preferably, in a hospital setting, such as in an emergency department, or in an intensive care unit (ICU). The method is very useful to monitor the effect of a therapy that has been initiated on a critically ill patient and can be used to judge whether a patient under treatment is a high risk patient that should be under intense medical observation and should potentially receive additional therapeutic measures, or whether the patient is a low risk patient with an improving health state that might not require as intense observation and further treatment measures, possibly because the initiated treatment is successfully improving the state of the patient. Initial treatments of critically ill patients may have a direct effect on the likelihood of adverse events in the health of the patient. As such, the assessment of risk/prognosis of a future adverse event provides feedback on or monitoring of the therapy instigated.

The likelihood of the occurrence of a subsequent adverse event can be assessed on the comparison of the level of proADM or fragments thereof in the sample in comparison to a reference level (such as a threshold or cut-off value and/or a population average), wherein the reference level may correspond to proADM or fragments thereof in healthy patients, or in patients who have been diagnosed as critically ill.

Accordingly, the method of the present invention can help to predict the likelihood of a subsequent adverse event in the health of the patient. This means, that the method of the invention can discriminate high risk patients, who are more likely to suffer from complications, or whose state will become more critical in the future, from low risk patients, whose health state is stable or even improving, so that it is not expected that they will suffer from an adverse event, such as death of the patient or a deterioration of the patient's clinical symptoms or signs, which might require certain therapeutic measures.

A particular advantage of the method of the present invention is that a patient who has been identified as a low risk patient by means of the method of the present invention could be more rapidly discharged from an ICU, the hospital in general or may require less frequent monitoring. Also, for low risk patients, the intensity and/or frequency of the observation of the health status of the patient could be decreased. Accordingly, the hospital or other medical institution in charge of the patient could more efficiently decide which patients require intensive medical care and observation. Consequently, the respective hospital or institution could, for example, more efficiently occupy ICU beds with high-risk patients. This would lead to an improved medical care for the high-risk patients, since the medical personnel could focus on such patients, while low risk patients could be discharged from the ICU. This would also lead to significant benefits from avoided costs for unnecessary measures that would otherwise be applied to low risk patients.

The time point when the patients have been diagnosed as being critically ill and the first treatment measures are initiated is defined as "time point 0", which may be the reference for the time point of isolation of the sample used for determining proADM or fragments thereof. If diagnosis of the patient and treatment initiation do not occur at the same time, time point 0 is the time point when the later of the two events of diagnosis and initiation of medical treatment occurs. Typically, diagnosis of critically ill patients is immediately followed by or concomitant to initiation of therapy or medical interventions such as surgery and/or source control (e.g. elimination of necrotic tissue). In the case of coagulative dysfunction the starting point of interventions can vary from time to time depending on the severity of the condition or other complications.

It was entirely surprising that the level of proADM or fragments thereof in a sample from the patient can provide critical information about the likelihood of the occurrence of a subsequent adverse event in the health of said critically ill patients. There has been no indication that a single measurement of proADM or fragments thereof after diagnosis and treatment initiation of a critically ill patient could provide such important information with respect to success of the ongoing treatment and prognosis of the health status of the patient.

The use of proADM or fragments thereof as a single parameter in embodiments of the present invention is advantageous over the use of other single parameters, such as biomarkers or clinical scores, since proADM is more precise in the prediction of an adverse event as compared to other markers such as for the platelet count, PCT, CRP, lactate or clinical scores such as SOFA, SAPS II or APACHE II, and markers for a dysregulation of the coagulation system, such as membrane microparticle, platelet count, mean platelet volume (MPV), sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay.

According to a preferred embodiment, the sample is isolated from a patient during a medical examination.

According to a preferred embodiment, the sample is isolated from said patient within 30 minutes after said diagnosis and treatment initiation, or at least 30 minutes, 1 hour, 2 hours, 6 hours, 12 hours, 24 hours, 4 days, 7 days or 10 days after said diagnosis and treatment initiation. In other embodiments the sample is isolated from said patient 12-36 hours and/or 3-5 days after treatment initiation.

The fact that the level of proADM or fragments thereof at a time point as short as about 30 minutes after diagnosis and treatment initiation can provide such information was completely unexpected.

In preferred embodiments of the method of the present invention said sample is isolated from said patient about 30 minutes, 1 hour, 2 hours, 3 hours, 4, hours, 5 hours, 6 hours, 7 hours, 8 hours, 9 hours, 10 hours, 11 hours, 12 hours, 14 hours, 16 hours, 18 hours, 20 hours 22 hours, 24 hours, 30 hours, 36 hours, 42 hours, 48 hours, 60 hours, 72 hours, 84 hours, 4 days, 5 days, 6 days, 7 days, 8 days 9 days or 10 days after said diagnosis and treatment initiation.

In other embodiments, the sample is isolated at time points after said diagnosis and initiating antibiotic treatment of 30 minutes to 12 hours, 12-36 hours, 3-5 days, 7-14 days, 8-12 days, or 9-11 days.

Ranges between any given of the above values may be employed to define the time point of obtaining the sample.

In another preferred embodiment of the present invention, the patient has been diagnosed using at least one additional biomarker or a clinical score. It is particularly advantageous in the context of the present invention, if the initial diagnosis of the critical illness of the patient at time point 0 was based at least partially on the level of at least one biomarker or a determined clinical score.

In certain embodiments the present invention comprises the determination of additional parameters, such as markers, biomarkers, clinical scores or the like.

In another preferred embodiment of the present invention, the patient has been diagnosed using at least one of the biomarkers or clinical scores procalcitonin (PCT), lactate and C-reactive protein and/or at least one of the clinical scores SOFA, APACHE II, SAPS II, and markers for a dysregulation of the coagulation system, such as membrane microparticle, platelet count, mean platelet volume (MPV), sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay. In embodiments, the additional one or more markers comprise one or more histones. Determining proADM or fragments thereof in samples of patients that have been diagnosed as being critically ill and are under treatment proved to be particularly useful for therapy monitoring if the diagnosis of the patient has been based on of these markers, since the prognosis of an adverse event in such patient groups may be more precise as compared to critically ill patients that have been diagnosed by other means.

In one embodiment of the invention, the critically ill patient is a patient diagnosed with or being at risk of developing a dysregulation of the coagulation system, an infectious disease, a patient diagnosed with an infectious disease and one or more existing organ failure(s), a patient diagnosed with sepsis, severe sepsis or septic shock and/or a posttraumatic or postsurgical patient. In light of the data presented herein, the prognostic value of proADM in samples of these patient groups is particularly accurate in predicting the likelihood of an adverse event in these patients.

In preferred embodiments of the present invention, the adverse event in the health of said patient is death, preferably death within 28-90 days after diagnosis and treatment initiation, a new infection, organ failure and/or a deterioration of clinical symptoms requiring a focus cleaning procedure, transfusion of blood products, infusion of colloids, emergency surgery, invasive mechanical ventilation, adverse drug reactions and/or renal or liver replacement.

In preferred embodiments of the invention, said level of proADM or fragment(s) thereof correlates with the likelihood of a subsequent adverse event in the health of said patient within 28 days after diagnosis and treatment initiation. In further preferred embodiments of the invention, said level of proADM or fragment(s) thereof correlates with the likelihood of a subsequent adverse event in the health of said patient within 90 days after diagnosis and treatment initiation.

In certain embodiments of the invention, the treatment received by the patient comprises one or more of antibiotic or antiinfective treatment, invasive mechanical ventilation, non-invasive mechanical ventilation, renal replacement therapy, vasopressor use, fluid therapy, platelet transfusion, blood transfusion, extracorporal blood purification, source control and/or organ protection.

In preferred embodiments of the invention, the sample is selected from the group consisting of a blood sample or fraction thereof, a serum sample, a plasma sample and/or a urine sample.

In further embodiments of the invention the level of proADM or fragment(s) thereof correlates with the likelihood of a subsequent adverse event in the health of said patient. In a preferred embodiment the level of proADM or fragment(s) thereof positively correlates with the likelihood of a subsequent adverse event in the health of said patient. In other words, the higher the level of proADM determined, the greater the likelihood of a subsequent adverse event.

According to a preferred embodiment of the present invention,
- a low severity level of proADM or fragment(s) thereof is indicative of the absence of a subsequent adverse event, or indicates a low risk of a subsequent adverse event, wherein the low severity level is below 4 nmol/l, preferably below 3 nmol/l, more preferably below 2.7 nmol/l, or
- a high severity level of proADM or fragment(s) thereof is indicative of a subsequent adverse event, or indicates a high risk of a subsequent adverse event, wherein the high severity level is above 6.5 nmol/l, preferably above 6.95 nmol/l, more preferably above 10.9 nmol/l.

According to a preferred embodiment of the present invention,
- a level of proADM or fragment(s) thereof below 4 nmol/l, preferably below 3 nmol/l, more preferably below 2.7 nmol/l, is indicative of the absence of a subsequent adverse event, or indicates a low risk of a subsequent adverse event, or
- a level of proADM or fragment(s) thereof above 6.5 nmol/l, preferably above 6.95 nmol/l, more preferably above 10.9 nmol/l, is indicative of a subsequent adverse event, or indicates a high risk of a subsequent adverse event.

According to a preferred embodiment of the present invention,
- a low severity level of proADM or fragment(s) thereof is indicative of the absence of a subsequent adverse event, wherein the low severity level is below 2.7 nmol/l, or
- a high severity level of proADM or fragment(s) thereof is indicative of a subsequent adverse event, wherein the high severity level is above 10.9 nmol/l.

This embodiment of the present invention is particularly advantageous when levels of proADM or fragments thereof are determined in a sample that has been isolated on the day of diagnosis and treatment initiation of the patient, particularly about 30 minutes after diagnosis and treatment initiation.

According to a preferred embodiment of the present invention,
- a low severity level of proADM or fragment(s) thereof is indicative of the absence of a subsequent adverse event, wherein the low severity level is below 2.7 nmol/l, or
- a high severity level of proADM or fragment(s) thereof is indicative of a subsequent adverse event, wherein the high severity level is above 10.9 nmol/l,
  wherein the level of proADM or fragments thereof is determined in a sample that has been isolated preferably on the day of diagnosis and treatment initiation.

According to a preferred embodiment of the present invention,
- a low severity level of proADM or fragment(s) thereof is indicative of the absence of a subsequent adverse event, wherein the low severity level is below 2.8 nmol/l, or
- a high severity level of proADM or fragment(s) thereof is indicative of a subsequent adverse event, wherein the high severity level is above 9.5 nmol/l.

This embodiment of the present invention is particularly advantageous when levels of proADM or fragments thereof are determined in a sample that has been isolated on 1 day after said diagnosis and treatment initiation.

According to a preferred embodiment of the present invention,
- a low severity level of proADM or fragment(s) thereof is indicative of the absence of a subsequent adverse event, wherein the low severity level is below 2.8 nmol/l, or
- a high severity level of proADM or fragment(s) thereof is indicative of a subsequent adverse event, wherein the high severity level is above 9.5 nmol/l,
  wherein the level of proADM or fragments thereof is determined in a sample that has been isolated preferably 1 day after diagnosis and treatment initiation.

For example, if the level of proADM or fragments thereof falls into the category of a low severity level of proADM, the treating physician can decide with more confidence to discharge said patient from ICU, because it is unlikely that an adverse event in the health of said patient would occur, preferably, within the next 28 days, more preferably within the next 90 days. Accordingly, it might not be necessary to keep this patient on the ICU. It might also be possible to conclude that the ongoing treatment is successfully improving the health state of the patient, as assessed by a measurement of risk of an adverse event.

In contrast, if the determination of the level of proADM or fragments thereof of said ICU patient indicates a high severity level of proADM or fragments thereof, the treating physician should keep the patient on the ICU. Additionally, it should be considered to adjust the treatment of the patient, because it is likely that the current treatment is not improving the health state of the patient, which is why the patient is more likely to suffer form an adverse event in the future.

According to a particularly preferred embodiment of the present invention the low severity level is below 2.75 nmol/l, said sample is isolated from the ICU-patient 1 day or more after said diagnosis and treatment initiation, and the low severity level of proADM or fragment(s) thereof indicates discharging of said patient from ICU.

The present invention further relates to a method for therapy monitoring, comprising the prognosis, risk assessment and/or risk stratification of a subsequent adverse event in the health of a patient, comprising
- providing a sample of said patient, wherein the patient is an intensive care unit (ICU)-patient and medical treatment has been initiated, wherein the sample is isolated from the patient after admission to ICU and treatment initiation,
- determining a level of proadrenomedullin (proADM) or fragment(s) thereof in said sample,
- wherein said level of proADM or fragment(s) thereof correlates with the likelihood of a subsequent adverse event in the health of said patient.

In the context of the method of the present invention relating to ICU-patients, the reference for the time point of isolation of the sample used for determining proADM or fragments thereof is the time point when the patients are admitted to the ICU and the first treatment measures are initiated (time point 0). This time point corresponds to the time point of diagnosis and treatment initiation in the method of the present invention relating to patients that have been diagnosed as being critically ill.

All embodiments of the method of the present invention relating to patients that have been diagnosed as being Embodiments of the Invention Relating to Additionally Determining a Level of PCT and/or Other Biomarkers or Clinical Scores in a First and a Second Sample (or at the Time Point of Isolation of a First and a Second Sample)

A preferred embodiment of the present invention comprises additionally determining a level of PCT or fragment(s) thereof in a sample isolated from the patient. In a preferred embodiment, the sample for determining a level of PCT or fragment(s) thereof is isolated before, at or after the time point of diagnosis and treatment initiation.

It is particularly advantageous to combine the determination of proADM or fragments thereof with the determination of PCT or fragments thereof in a sample, wherein the sample used for determining proADM may be the same or a different sample used for detecting PCT.

The combined determination of proADM or fragments thereof with the determination of PCT or fragments thereof, whether in the same sample or in samples obtained at different time points, provides a synergistic effect with respect to the accuracy and reliability of determining the risk of a subsequent adverse event. These synergistic effects also exist for the combined assessment of proADM or fragments therefor with other markers or clinical scores, such as platelet counts, mean platelet volume (MPV), lactate, CRP, qSOFA, SOFA, SAPS II, APACHE II, or other clinical assessments.

According to a further preferred embodiment of the present invention, the method described herein comprises additionally
determining a level of PCT or fragment(s) thereof in a first sample isolated from the patient, wherein said first sample is isolated before, at or after the time point of diagnosis and treatment initiation,
determining a level of PCT or fragment(s) thereof in a second sample isolated from said patient, wherein the second sample has been isolated after the first sample, preferably within 30 minutes after isolation of the first sample or 30 minutes, 1 hour, 2 hours, 6 hours, 12 hours, 24 hours, 4 days, 7 or 10 days after isolation of the first sample, and
determining a difference in the level of PCT or fragment(s) thereof in the second sample in comparison to the level of PCT or fragment(s) thereof in the first sample.

It is particularly advantageous to combine the determination of proADM or fragments thereof in a sample isolated from a patient with the determination of PCT or fragments thereof in a first sample and determining the level of PCT or fragments thereof in a second sample isolated after the first sample, wherein the sample used for the determination of proADM or fragments thereof may be the same of different than the first sample or the second sample used for determining PCT or fragments thereof.

In a preferred embodiment of the method described herein comprises additionally
determining a level of PCT or fragment(s) thereof in a first sample isolated from the patient, wherein said first sample is isolated at or before the time point of diagnosis and treatment initiation (time point 0),
determining a level of PCT or fragment(s) thereof in a second sample (sample of claim 1) isolated from said patient after diagnosis and treatment initiation, preferably within 30 minutes after said diagnosis and treatment initiation or 30 minutes, 1 hour, 2 hours, 6 hours, 12 hours, 24 hours, 4 days, 7 or 10 days after said diagnosis and treatment initiation, and
determining a difference in the level of PCT or fragment(s) thereof in the second sample in comparison to the level of PCT or fragment(s) thereof in the first sample.

It is particularly advantageous to combine the determination of proADM or fragments thereof (in a second sample) with the determination of PCT or fragments thereof in an earlier sample (first sample) that is isolated from said patient and that may be used for diagnosing said patient as being critically ill at time point 0 and determining the level of PCT or fragments thereof in a second sample isolated at a certain time point after diagnosis and treatment initiation, which is also preferably the same time point when proADM or fragments thereof are determined. As indicated by the data below, determining a difference in the level of PCT or fragments thereof in the second sample in comparison to the first sample adds additional information to the information gained from the levels of proADM or fragments thereof in the second sample. Based on this combined information it might be possible to predict with a higher probability whether an adverse event in the health of said patient will occur as compared to predicting the likelihood of an adverse event purely on the information about the level of proADM or fragments thereof in the second sample. This represents a surprising finding, as biomarkers for sepsis are typically not synergistic or complementary, but represent mere alternative diagnostic markers.

In a preferred embodiment of the method described herein comprises additionally
determining a platelet count in a first sample isolated from the patient, wherein said first sample is isolated at or before the time point of diagnosis and treatment initiation (time point 0),
determining a platelet count in a second sample (sample of claim 1) isolated from said patient within 30 minutes after said diagnosis and treatment initiation or at least 30 minutes, preferably 1 hour, 2 hours, 6 hours, 12 hours, 24 hours, 4 days, 7 or 10 days after said diagnosis and treatment initiation, and
determining a difference in the platelet count in the second sample in comparison to the platelet count in the first sample.

It is particularly advantageous to combine the determination of proADM or fragments thereof with the determination of platelet counts in a sample, wherein the sample used for determining proADM may be the same or a different sample used for detecting platelet counts.

A preferred embodiment of the present invention comprises additionally determining SOFA or qSOFA. In a preferred embodiment, qSOFA or SOFA is determined before, at or after the time point of diagnosis and treatment initiation.

It is particularly advantageous to combine the determination of proADM or fragments thereof with the determination SOFA, wherein the time point of sample isolation for determining proADM may be the same or a different from the time point of determining SOFA.

According to a further preferred embodiment of the present invention, the method described herein comprises additionally
determining a first SOFA before, at or after the time point of diagnosis and treatment initiation,
determining a second SOFA within 30 minutes after determining the first SOFA or 30 minutes, 1 hour, 2 hours, 6 hours, 12 hours, 24 hours, 4 days, 7 or 10 days after determining the first SOFA, and determining a difference in the two determined SOFA.

In a preferred embodiment of the method described herein comprises additionally determining SOFA at or before the time point of diagnosis and treatment initiation (time point 0), determining SOFA within 30 minutes after said diagnosis and treatment initiation or at least 30 minutes, preferably 1 hour, 2 hours, 6 hours, 12 hours, 24 hours, 4 days, 7 or 10 days after said diagnosis and treatment initiation, and determining a difference in SOFA determined after said diagnosis and treatment initiation and SOFA determined at time point 0.

A preferred embodiment of the present invention comprises additionally determining SAPS II. In a preferred embodiment, SAPS II is determined before, at or after the time point of diagnosis and treatment initiation.

It is particularly advantageous to combine the determination of proADM or fragments thereof with the determination SAPS II, wherein the time point of sample isolation for determining proADM may be the same or a different from the time point of determining SAPS II.

According to a further preferred embodiment of the present invention, the method described herein comprises additionally determining a first SAPS II before, at or after the time point of diagnosis and treatment initiation, determining a second SAPS II within 30 minutes after determining the first SOFA or 30 minutes, 1 hour, 2 hours, 6 hours, 12 hours, 24 hours, 4 days, 7 or 10 days after determining the first SAPS II, and determining a difference in the two determined SAPS II.

In a preferred embodiment of the method described herein comprises additionally determining SAPS II at or before the time point of diagnosis and treatment initiation (time point 0), determining SAPS II within 30 minutes after said diagnosis and treatment initiation or at least 30 minutes, preferably 1 hour, 2 hours, 6 hours, 12 hours, 24 hours, 4 days, 7 or 10 days after said diagnosis and treatment initiation, and determining a difference in SAPS II determined after said diagnosis and treatment initiation and SAPS II determined at time point 0.

A preferred embodiment of the present invention comprises additionally determining APACHE II. In a preferred embodiment, APACHE II is determined before, at or after the time point of diagnosis and treatment initiation.

It is particularly advantageous to combine the determination of proADM or fragments thereof with the determination APACHE II, wherein the time point of sample isolation for determining proADM may be the same or a different from the time point of determining APACHE II.

According to a further preferred embodiment of the present invention, the method described herein comprises additionally determining a first APACHE II before, at or after the time point of diagnosis and treatment initiation, determining a second APACHE II within 30 minutes after determining the first APACHE II or 30 minutes, 1 hour, 2 hours, 6 hours, 12 hours, 24 hours, 4 days, 7 or 10 days after determining the first APACHE II, and determining a difference in the two determined APACHE II.

In a preferred embodiment of the method described herein comprises additionally determining APACHE II at or before the time point of diagnosis and treatment initiation (time point 0), determining APACHE II within 30 minutes after said diagnosis and treatment initiation or at least 30 minutes, preferably 1 hour, 2 hours, 6 hours, 12 hours, 24 hours, 4 days, 7 or 10 days after said diagnosis and treatment initiation, and determining a difference in APACHE II determined after said diagnosis and treatment initiation and APACHE II determined at time point 0.

In a preferred embodiment, it is possible to identify high-risk patients with increasing PCT levels and a high severity level of proADM or fragments thereof, which represent a more accurate identification of such patients that a likely to suffer from an adverse event in the future. Accordingly, the treatment of these patients could be adjusted while minimizing the risk that this patient might have been a low-risk patient.

Embodiments of the Present Invention Relating to Determining a Level of proADM or Fragment(s) Thereof in a First and a Second Sample A preferred embodiment of the method of the present invention comprises additionally determining a level of proADM or fragment(s) thereof in a first sample isolated from the patient, wherein said first sample is isolated before, at or after the time point of diagnosis and treatment initiation, and determining a level of proADM or fragment(s) thereof in a second sample isolated from said patient, wherein said second sample has been isolated after the first sample and after the time point of diagnosis and treatment initiation, preferably within 30 minutes after isolation of the first sample or 30 minutes, 1 hour, 2 hours, 6 hours, 12 hours, 24 hours, 4 days, 7 or 10 days after isolation of the first sample, and determining whether a difference in the level of proADM or fragment(s) thereof in the second sample in comparison to the level of proADM or fragment(s) thereof in the first sample is evident.

The first and the second sample used for determining a level of proADM or fragment(s) thereof may be the same of different from the first and the second sample used for determining a level of PCT or fragment(s) thereof.

A preferred embodiment of the method of the present invention comprises additionally determining a level of proADM or fragment(s) thereof in a first sample isolated from the patient, wherein said first sample is isolated at or before the time point of diagnosis and treatment initiation (time point 0), and determining a level of proADM or fragment(s) thereof in a second sample isolated after diagnosis and treatment initiation, preferably within 30 minutes, or after 30 minutes, 1 hour, 2 hours, 6 hours, 12 hours, 24 hours, 4 days, 7 or 10 days after said diagnosis and treatment initiation, and determining whether a difference in the level of proADM or fragment(s) thereof in the second sample in comparison to the level of proADM or fragment(s) thereof in the first sample is evident.

A preferred embodiment of the method of the present invention comprises additionally determining a level of proADM or fragment(s) thereof in a first sample isolated from the patient, wherein said first sample is used for diagnosing said patient as being critically ill (time point 0), and determining a level of proADM or fragment(s) thereof in a second sample isolated after diagnosis and treatment initiation, preferably within 30 minutes, or after 30 minutes, 1 hour, 2 hours, 6 hours, 12 hours, 24 hours, 4 days, 7 or 10 days after said diagnosis and treatment initiation, and determining whether a difference in the level of proADM or fragment(s) thereof in the second sample in comparison to the level of proADM or fragment(s) thereof in the first sample is evident.

A further preferred embodiment of the method of the present invention comprises additionally determining a level of proADM or fragment(s) thereof and optionally PCT or fragment(s) thereof in a first sample isolated from the patient, wherein said first sample is isolated at or before the time point of diagnosis and treatment initiation (time point 0), and determining a level of proADM or fragment(s) thereof and optionally PCT or fragment(s) thereof in a second sample isolated from said patient after said diagnosis and treatment initiation, preferably within 30 minutes or at least 30 minutes after diagnosis and treatment initiation, preferably 1 hour, 2 hours, 6 hours, 12 hours, 24 hours, 4 days, 7 or 10 days after said diagnosis and treatment initiation, and determining a difference in the level of proADM or fragment(s) thereof and/or a difference in the level of PCT or fragments thereof in the second sample in comparison to the level of proADM or fragment(s) thereof in the first sample.

A further preferred embodiment of the method of the present invention comprises additionally determining a level of proADM or fragment(s) thereof and optionally PCT or fragment(s) thereof in a first sample isolated from the patient, wherein said first sample is used for diagnosing said patient as being critically ill (time point 0), and determining a level of proADM or fragment(s) thereof and optionally PCT or fragment(s) thereof in a second sample isolated from said patient after said diagnosis and treatment initiation, preferably within 30 minutes or at least 30 minutes after diagnosis and treatment initiation, preferably 1 hour, 2 hours, 6 hours, 12 hours, 24 hours, 4 days, 7 or 10 days after said diagnosis and treatment initiation, and determining a difference in the level of proADM or fragment(s) thereof and/or a difference in the level of PCT or fragments thereof in the second sample in comparison to the level of proADM or fragment(s) thereof in the first sample.

It was surprising that the determination of the change of the levels of proADM or fragments thereof from the time point of diagnosis and treatment initiation to a later time point can provide additional information with respect to the occurrence of a future adverse event in the health of a patient that has been diagnosed as being critically ill, e.g. the patient has been diagnosed with thrombocytopenia. It is a great advantage of this embodiment of the present invention that the same sample that is used for the determining of a diagnostic marker at time point 0 can also be used for determining the baseline level of proADM or fragments thereof, which can be compared to the level of proADM or fragments thereof at a later time point after diagnosis and treatment initiation. By determining the change of the level of proADM or fragments thereof of the course of patient treatment the accuracy of predicting the occurrence of an adverse event in the health of the patient can be further increased.

In one embodiment of the method described herein, an elevated level of proADM or fragment(s) thereof in the second sample compared to the first sample is indicative of a subsequent adverse event.

It was surprising that based on the change of the level of proADM or fragments thereof it is possible to confidently predict the likelihood of the occurrence of an adverse event in the health of the patient without determining further markers. An increase of the level or severity level of proADM or fragments thereof from the time point of diagnosis and treatment initiation indicates that it is likely that an adverse event will occur. Accordingly, based on the change of proADM or fragments thereof over the course of the treatment a physician can decide whether to change or modify the treatment of the patient or to stick to the initial treatment.

In a preferred embodiment of the method of the present invention an elevated level of proADM or fragment(s) thereof and an elevated level of PCT or fragment(s) thereof in the second sample compared to the first sample is indicative of a subsequent adverse event, and/or In some embodiments of the present invention, an elevated level of proADM or fragments thereof in the second sample as compared to the first sample relates to an elevated severity level of proADM or fragments thereof. Conversely, in some embodiments of the present invention, a lower level of proADM or fragments thereof in the second sample as compared to the first sample refer to a lower severity level of proADM or fragments thereof in the second sample as compared to the first sample.

It is a great advantage that based on the change in the level of proADM or fragments thereof in combination with the determined change of PCT or fragments thereof over the course of treatment of a critically ill patient the likelihood of an adverse event in the health of the patient can be assessed. Accordingly, it is possible to confidently identify high-risk patients and low-risk patients based on the changes of these two markers.

It is advantageous that by means of a combined analysis of the change in the level of PCT or fragments thereof and the severity level of proADM or fragments thereof at the time point of the isolation of the second sample (the later time point) in an ICU patient it can be decided whether a patient is a low-risk patient that can be discharged from ICU while maintaining the ongoing treatment, or whether a patient is a high-risk patient that requires a modification or adjustment of the current therapy on ICU to prevent the occurrence of an adverse event that is indicated by the respective combination of the change in PCT levels and the current severity level of proADM In a further embodiment, the present invention relates to a kit for carrying out the method of the present invention, wherein the kit comprises detection reagents for determining the level proADM or fragment(s) thereof, and optionally additionally for determining the level of PCT, and reference data, such as a reference level, corresponding to high and/or low severity levels of proADM, wherein the low severity level is below 4 nmol/l, preferably below 3 nmol/l, more preferably below 2.7 nmol/l, and the high severity level is above 6.5 nmol/l, preferably above 6.95 nmol/l, more preferably above 10.9 nmol/l, and optionally PCT, wherein said reference data is preferably stored on a computer readable medium and/or employed in the form of computer executable code configured for comparing the determined levels of proADM or fragment(s) thereof, and optionally additionally the determined levels of PCT, lactate and/or C-reactive protein or fragment(s) thereof, to said reference data.

In a further embodiment, the present invention relates to a kit for carrying out the method of the present invention, wherein the kit comprises
detection reagents for determining the level proADM or fragment(s) thereof, and optionally additionally for determining the level of PCT and/or one or more markers for a dysregulation of the coagulation system, such as membrane microparticle, platelet count, mean platelet volume (MPV), sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay, in a sample from a subject, and
reference data, such as a reference level, corresponding to high and/or low severity levels of proADM, wherein the low severity level is below 4 nmol/l, preferably below 3 nmol/l, more preferably below 2.7 nmol/l, and the high severity level is above 6.5 nmol/l, preferably above 6.95 nmol/l, more preferably above 10.9 nmol/l, and optionally PCT and/or one or more markers for a dysregulation of the coagulation system, such as membrane microparticle, platelet count, mean platelet volume, sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay, wherein said reference data is preferably stored on a computer readable medium and/or employed in the form of computer executable code configured for comparing the determined levels of proADM or fragment(s) thereof, and optionally additionally the determined levels of PCT and/or one or more markers for a dysregulation of the coagulation system, such as membrane microparticle, platelet count, mean platelet volume (MPV), sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay, to said reference data.

In a further embodiment, the present invention relates to a kit for carrying out the method of the present invention, wherein the kit comprises
detection reagents for determining the level of proADM or fragment(s) thereof, and optionally additionally for determining the level of PCT or fragment(s) thereof, in a sample from a subject, and
reference data, such as a reference level, corresponding to high and/or low severity levels of proADM, wherein the low severity level is below 4 nmol/l, preferably below 3 nmol/l, more preferably below 2.7 nmol/l, and the high severity level is above 6.5 nmol/l, preferably above 6.95 nmol/l, more preferably above 10.9 nmol/l, and optionally PCT levels, wherein said reference data is preferably stored on a computer readable medium and/or employed in the form of computer executable code configured for comparing the determined levels of proADM or fragment(s) thereof, and optionally additionally the determined levels of PCT or fragment(s) thereof, to said reference data.

In one embodiment the invention relates to a kit for carrying out the method described herein, comprising:
detection reagents for determining the level proADM or fragment(s) thereof, and optionally additionally for determining the level of PCT or fragment(s) thereof, in a sample from a subject, and
reference data, such as a reference level, corresponding to proADM severity levels of claims 6 and/or 9, and optionally PCT levels, wherein said reference data is preferably stored on a computer readable medium and/or employed in in the form of computer executable code configured for comparing the determined levels of proADM or fragment(s) thereof, and optionally additionally the determined levels of PCT or fragment(s) thereof, to said reference data.

DETAILED DESCRIPTION OF THE INVENTION

The present invention is based on a finding that identified a correlation between proADM levels and platelet counts. The present methods enable determining, diagnosis, prognosis, treatment guidance, treatment monitoring, risk assessment and/or risk stratification of abnormal platelet levels in a patient, wherein said level of proADM or fragment(s) thereof correlates with the abnormal platelet levels in said patient.

The present invention has the following advantages over the conventional methods: the inventive methods and the kits are fast, objective, easy to use and precise for therapy monitoring of critically ill patients. The methods and kits of the invention relate to markers and clinical scores that are easily measurable in routine methods in hospitals, because the levels of proADM, PCT, lactate, c-reactive protein, SOFA, APACHE II, SAPS II and/or markers for a dysregulation of the coagulation system, such as membrane microparticle, platelet count, mean platelet volume (MPV) sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay, can be determined in routinely obtained blood samples or further biological fluids or samples obtained from a subject.

As used herein, the "patient" or "subject" may be a vertebrate. In the context of the present invention, the term "subject" includes both humans and animals, particularly mammals, and other organisms.

In the context of the present invention, an "adverse event in the health of a patient" relates to events that indicate complications or worsening of the health state of the patient. Such adverse events include, without limitation, death of the patient, death of a patient within 28-90 days after diagnosis and treatment initiation, occurrence of an infection or a new infection, organ failure and deterioration of the patient's general clinical signs or symptoms, such as hypotension or hypertension, tachycardia or bradycardia, dysregulation of the coagulation system, disseminated intravascular coagulation, abnormal platelet levels, thrombocytopenia and dysregulated organ functions or organ failure associated with thrombocytopenia. Furthermore, examples of adverse events include situations where a deterioration of clinical symptoms indicates the requirement for therapeutic measures, such as a focus cleaning procedure, transfusion of blood products, infusion of colloids, invasive mechanical ventilation, platelet transfusion, non-invasive mechanical ventilation, emergency surgery, organ replacement therapy, such as renal or liver replacement, and vasopressor therapy. Furthermore, adverse events may include provision of corticosteroids, blood or platelet transfusion, transfusion of blood components, such as serum, plasma or specific cells or combinations thereof, drugs promoting the formation of thrombocytes, causative treatment or preforming a splenectomy.

The patient described herein who has been diagnosed as being "critically ill" can be diagnosed as an intensive care unit (ICU) patient, a patient who requires constant and/or intense observation of his health state, a patient diagnosed with sepsis, severe sepsis or septic shock, a patient diagnosed with an infectious disease and one or more existing organ failure(s), a pre- or post-surgical patient, an intraoperative patient, a posttraumatic patient, a trauma patient, such as an accident patient, a burn patient, a patient with one or more open lesions. The subject described herein can be at the emergency department or intensive care unit, or in other point of care settings, such as in an emergency transporter, such as an ambulance, or at a general practitioner, who is confronted with a patient with said symptoms. Furthermore, in the context of the present invention critically ill may refer to a patient at risk of getting or having a dysregulated coagulation system. Therefore in the context of the present invention critically ill preferably refers to a patient at risk of getting or having a low platelet number (thrombocytopenia). More preferably in the context of the present invention critically ill refers to a patient at risk of getting or having a low platelet number (thrombocytopenia) secondary to a systemic infection, sepsis, severe sepsis or septic shock. Patients that are suspected to suffer from SIRS are not necessarily considered to be critically ill.

The term "ICU-patient" patient relates, without limitation, a patient who has been admitted to an intensive care unit. An intensive care unit can also be termed an intensive therapy unit or intensive treatment unit (ITU) or critical care unit (CCU), is a special department of a hospital or health care facility that provides intensive treatment medicine. ICU-patients usually suffer from severe and life-threatening illnesses and injuries, which require constant, close monitoring and support from specialist equipment and medications in order to ensure normal bodily functions. Common conditions that are treated within ICUs include, without limitation, acute or adult respiratory distress syndrome (ARDS), trauma, organ failure and sepsis.

As use herein, the term "coagulation system" refers to the components present in blood that enable coagulation. Coagulation (also known as clotting) is the process by which blood changes from a liquid to a gel, forming a blood clot. It potentially results in hemostasis, the cessation of blood loss from a damaged vessel, followed by repair. The mechanism of coagulation involves activation, adhesion, and aggregation of platelets along with deposition and maturation of fibrin. Disorders of coagulation are disease states which can result in bleeding (hemorrhage or bruising) or obstructive clotting (thrombosis). Coagulation begins almost instantly after an injury to the blood vessel has damaged the endothelium lining the vessel. Leaking of blood through the endothelium initiates two processes: changes in platelets, and the exposure of subendothelial tissue factor to plasma Factor VII, which ultimately leads to fibrin formation. Platelets immediately form a plug at the site of injury; this is called primary hemostasis. Secondary hemostasis occurs simultaneously: Additional coagulation factors or clotting factors beyond Factor VII respond in a complex cascade to form fibrin strands, which strengthen the platelet plug. Examples of coagulation factors comprise, without limitation, platelets, factor I (fibrinogen), factor II (prothrombin), factor III (tissue factor or tissue thromboplastin), factor IV Calcium, factor V (proaccelerin, labile factor), factor VI, factor VII (stable factor, proconvertin), factor VIII (Antihemophilic factor A), factor IX (Antihemophilic factor B or Christmas factor), factor X (Stuart-Prower factor), factor XI (plasma thromboplastin antecedent), factor XII (Hageman factor), factor XIII (fibrin-stabilizing factor), von Willebrand factor, prekallikrein (Fletcher factor), high-molecular-weight kininogen (HMWK) (Fitzgerald factor), fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant.

As used herein, the term "abnormal platelet levels" refers to a number or concentration of platelets in the blood of a patient that is unexpectedly high or low. The to be expected value depends on the status of the patient. In healthy individuals or individual without a known basic disease, predisposition or diagnosis, normal or to be expected platelet counts are in the range of about 150-450 billion platelets per L or 150,000 to 450,000 platelets per µl. This range may vary for example if it is known that a patient suffers from a condition that affects platelet numbers.

Thrombocytopenia is a condition characterized by abnormally low levels of thrombocytes, also known as platelets, in the blood. A normal human platelet count ranges from 150,000 to 450,000 platelets per microliter of blood. These limits are determined by the 2.5th lower and upper percentile, so values outside this range do not necessarily indicate disease. Thrombocytopenia may require emergency treatment, especially if a platelet count below 50,000 per microliter is determined.

In the context of the present invention, the term thrombocytopenia comprises all forms and/or causes leading to abnormally low levels of thrombocytes, such as abnormally low platelet production may be caused by dehydration, Vitamin B12 or folic acid deficiency, leukemia or myelodysplastic syndrome or aplastic anemia, decreased production of thrombopoietin by the liver in liver failure, sepsis, systemic viral or bacterial infection, leptospirosis, hereditary syndromes, such as congenital amegakaryocytic thrombocytopenia, thrombocytopenia absent radius syndrome, Fanconi anemia, Bernard-Soulier syndrome, (associated with large platelets), May-Hegglin anomaly, Grey platelet syndrome, Alport syndrome, Wiskott-Aldrich syndrome; abnormally high rates of platelet destruction may be due to immune or non-immune conditions, including immune thrombocytopenic purpura, thrombotic thrombocytopenic purpura, hemolytic-uremic syndrome, disseminated intravascular coagulation, paroxysmal nocturnal hemoglobinuria, antiphospholipid syndrome, systemic lupus erythematosus, post-transfusion purpura, neonatal alloimmune thrombocytopenia, hypersplenism, dengue fever, Gaucher's disease, zika virus; medication-induced thrombocytopenia, for example induced by valproic acid, methotrexate, carboplatin, interferon, isotretinoin, panobinostat, Heparin, H2 blockers and proton-pump inhibitors; and other causes such as snakebite, niacin toxicity, Lyme disease and thrombocytapheresis (also called plateletpheresis).

The gold standard for measuring platelets/thrombocytes is the determination of (absolute) immature platelet counts ((A)IPC) by e.g. flow cytometry. However, this method is associated with the disadvantage that the technical validation of the platelet counts are sometimes difficult. Confounding factors make the results unreliable, leading to a requirement for an additional validation, which costs valuable time and staff. Analytical interferences can cause a pseudo-thrombocytopenia (e.g. by giant thrombocytes, reticulated thrombocytes, aggregation of thrombocytes or EDTA-incompatibility).

The term "septic thrombocytopenia" relates to the associated presence of sepsis and low platelet levels.

As used herein, "diagnosis" in the context of the present invention relates to the recognition and (early) detection of a clinical condition of a subject linked to an infectious disease. Also the assessment of the severity of the infectious disease may be encompassed by the term "diagnosis".

"Prognosis" relates to the prediction of an outcome or a specific risk for a subject based on an infectious disease. This may also include an estimation of the chance of recovery or the chance of an adverse outcome for said subject.

The methods of the invention may also be used for monitoring. "Monitoring" relates to keeping track of an already diagnosed infectious disease, disorder, complication or risk, e.g. to analyze the progression of the disease or the influence of a particular treatment or therapy on the disease progression of the disease of a critically ill patient or an infectious disease in a patient.

The term "therapy monitoring" or "therapy control" in the context of the present invention refers to the monitoring and/or adjustment of a therapeutic treatment of said subject, for example by obtaining feedback on the efficacy of the therapy.

In the present invention, the terms "risk assessment" and "risk stratification" relate to the grouping of subjects into different risk groups according to their further prognosis. Risk assessment also relates to stratification for applying preventive and/or therapeutic measures. Examples of the risk stratification are the low, intermediate and high risk levels disclosed herein.

As used herein, the term "therapy guidance" refers to application of certain therapies or medical interventions based on the value of one or more biomarkers and/or clinical parameter and/or clinical scores.

It is understood that in the context of the present invention "determining the level of proADM or fragment(s) thereof" or the like refers to any means of determining proADM or a fragment thereof. The fragment can have any length, e.g. at least about 5, 10, 20, 30, 40, 50 or 100 amino acids, so long as the fragment allows the unambiguous determination of the level of proADM or fragment thereof. In particular preferred aspects of the invention, "determining the level of proADM" refers to determining the level of midregional proadrenomedullin (MR-proADM). MR-proADM is a fragment and/or region of proADM.

The peptide adrenomedullin (ADM) was discovered as a hypotensive peptide comprising 52 amino acids, which had been isolated from a human phenochromocytome (Kitamura et al., 1993). Adrenomedullin (ADM) is encoded as a precursor peptide comprising 185 amino acids ("preproadrenomedullin" or "pre proADM"). An exemplary amino acid sequence of proADM is given in SEQ ID NO: 1.

```
SEQ ID NO: 1: amino acid sequence of
pre-pro-ADM:
    1 MKLVSVALMY LGSLAFLGAD TARLDVASEF RKKWNKWALS

RGKRELRMSS

51 SYPTGLADVK AGPAQTLIRP QDMKGASRSP EDSSPDAARI

RVKRYRQSMN

101 NFQGLRSFGC RFGTCTVQKL AHQIYQFTDK DKDNVAPRSK

ISPQGYGRRR

151 RRSLPEAGPG RTLVSSKPQA HGAPAPPSGS APHFL
```

ADM comprises the positions 95-146 of the pre-proADM amino acid sequence and is a splice product thereof. "Proadrenomedullin" ("proADM") refers to pre-proADM without the signal sequence (amino acids 1 to 21), i.e. to amino acid residues 22 to 185 of pre-proADM. "Midregional proadrenomedullin" ("MR-proADM") refers to the amino acids 42 to 95 of pre-proADM. An exemplary amino acid sequence of MR-proADM is given in SEQ ID NO: 2.

```
SEQ ID NO: 2: amino acid sequence of
MR-pro-ADM (AS 45-92 of pre-pro-ADM):
ELRMSSSYPT GLADVKAGPA QTLIRPQDMK GASRSPEDSS

PDAARIRV
```

It is also envisaged herein that a peptide and fragment thereof of pre-proADM or MR-proADM can be used for the herein described methods. For example, the peptide or the fragment thereof can comprise the amino acids 22-41 of pre-proADM (PAMP peptide) or amino acids 95-146 of pre-proADM (mature adrenomedullin, including the biologically active form, also known as bio-ADM). A C-terminal fragment of proADM (amino acids 153 to 185 of pre proADM) is called adrenotensin. Fragments of the proADM peptides or fragments of the MR-proADM can comprise, for example, at least about 5, 10, 20, 30 or more amino acids. Accordingly, the fragment of proADM may, for example, be selected from the group consisting of MR-proADM, PAMP, adrenotensin and mature adrenomedullin, preferably herein the fragment is MR-proADM.

The determination of these various forms of ADM or proADM and fragments thereof also encompass measuring and/or detecting specific sub-regions of these molecules, for example by employing antibodies or other affinity reagents directed against a particular portion of the molecules, or by determining the presence and/or quantity of the molecules by measuring a portion of the protein using mass spectrometry.

Any one or more of the "ADM peptides or fragments" described herein may be employed in the present invention.

The methods and kits of the present invention can also comprise determining at least one further biomarker, marker, clinical score and/or parameter in addition to proADM.

As used herein, a parameter is a characteristic, feature, or measurable factor that can help in defining a particular system. A parameter is an important element for health- and physiology-related assessments, such as a disease/disorder/clinical condition risk, preferably organ dysfunction(s). Furthermore, a parameter is defined as a characteristic that is objectively measured and evaluated as an indicator of normal biological processes, pathogenic processes, or pharmacologic responses to a therapeutic intervention. An exemplary parameter can be selected from the group consisting of Acute Physiology and Chronic Health Evaluation II (APACHE II), the simplified acute physiology score (SAPSII score), sequential organ failure assessment score (SOFA score), quick sequential organ failure assessment score (qSOFA), body mass index, weight, age, sex, IGS II, liquid intake, white blood cell count, sodium, platelet count, mean platelet volume (MPV), potassium, temperature, blood pressure, dopamine, bilirubin, respiratory rate, partial pressure of oxygen, World Federation of Neurosurgical Societies (WFNS) grading, and Glasgow Coma Scale (GCS).

As used herein, terms such as "marker", "surrogate", "prognostic marker", "factor" or "biomarker" or "biological marker" are used interchangeably and relate to measurable and quantifiable biological markers (e.g., specific protein or enzyme concentration or a fragment thereof, specific hormone concentration or a fragment thereof, or presence of biological substances or a fragment thereof) which serve as indices for health- and physiology-related assessments, such as a disease/disorder/clinical condition risk, preferably an adverse event. A marker or biomarker is defined as a characteristic that can be objectively measured and evaluated as an indicator of normal biological processes, pathogenic processes, or pharmacologic responses to a therapeutic intervention. Biomarkers may be measured in a sample (as a blood, serum, plasma, urine, or tissue test).

The at least one further marker and/or parameter of said subject can be selected from the group consisting of a level of lactate in said sample, a level of procalcitonin (PCT) in said sample, the sequential organ failure assessment score (SOFA score) of said subject, the simplified acute physiology score (SAPSII) of said subject, the Acute Physiology and Chronic Health Evaluation II (APACHE II) score of said subject and a level of the soluble fms-like tyrosine kinase-1 (sFlt-1), Histone H2A, Histone H2B, Histone H3, Histone H4, calcitonin, Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-6 (IL-6), Interleukin-1, Interleukin-24 (IL-24), Interleukin-22 (IL-22), Interleukin (IL-20) other ILs, Presepsin (sCD14-ST), Lipopolysaccharide Binding Protein (LBP), Alpha-1-Antitrypsin, Matrix Metalloproteinase 2 (MMP2), Metalloproteinase 2 (MMP8), Matrix Metalloproteinase 9 (MMP9), Matrix Metalloproteinase 7 (MMP7, Placental growth factor (PIGF), Chromogranin A, S100A protein, S100B protein and Tumor Necrosis Factor α (TNFα), Neopterin, Alpha-1-Antitrypsin, pro-arginine vasopressin (AVP, proAVP or Copeptin), procalcitonin, atrial natriuretic peptide (ANP, pro-ANP), Endothelin-1, CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, IL1F3/IL1RA, IL1F5, IL1F6, IL1F7, IL1F8, IL1RL2, IL1F9, IL33 or a fragment thereof. Further markers comprise membrane microparticle, platelet count, mean platelet volume (MPV), sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay.

Components of the coagulation system may also be considered as markers of biomarkers in the sense of the present invention and comprise, without limitation, platelets, factor I (fibrinogen), factor II (prothrombin), factor III (tissue factor or tissue thromboplastin), factor IV Calcium, factor V (proaccelerin, labile factor), factor VI, factor VII (stable factor, proconvertin), factor VIII (Antihemophilic factor A), factor IX (Antihemophilic factor B or Christmas factor), factor X (Stuart-Prower factor), factor XI (plasma thromboplastin antecedent), factor XII (Hageman factor), factor XIII (fibrin-stabilizing factor), von Willebrand factor, prekallikrein (Fletcher factor), high-molecular-weight kininogen (HMWK) (Fitzgerald factor), fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant As used herein, "procalcitonin" or "PCT" relates to a peptide spanning amino acid residues 1-116, 2-116, 3-116, or fragments thereof, of the procalcitonin peptide. PCT is a peptide precursor of the hormone calcitonin. Thus the length of procalcitonin fragments is at least 12 amino acids, preferably more than 50 amino acids, more preferably more than 110 amino acids. PCT may comprise post-translational modifications such as glycosylation, liposidation or derivatisation. Procalcitonin is a precursor of calcitonin and katacalcin. Thus, under normal conditions the PCT levels in the circulation are very low (<about 0.05 ng/ml).

The level of PCT in the sample of the subject can be determined by immunoassays as described herein. As used herein, the level of ribonucleic acid or deoxyribonucleic acids encoding "procalcitonin" or "PCT" can also be determined. Methods for the determination of PCT are known to a skilled person, for example by using products obtained from Thermo Fisher Scientific/B•R•A•H•M•S GmbH.

It is understood that "determining the level of at least one histone" or the like refers to determining the level of at least one histone or a fragment of the at least one histone in the sample. In particular, the level of the histone H2B, H3, H2A, and/or H4 is determined in the sample. Accordingly, the at least one histone determined in the sample can be a free histone or the at least one histone determined in the sample can occur and can be assembled in a macromolecular complex, for example, in the octamer, nucleosome and/or NETs.

The fragment of the at least one histone can have any length, e.g. at least about 5, 10, 20, 30, 40, 50 or 100 amino acids, so long as the fragment allows the unambiguous determination of the level of the particular histone. Various exemplary fragments of the histones are disclosed herein below that are suitable to determine the level of the histone in the sample of the subject. It is also herein understood that the level of the histones can be determined by determining a fragment spanning the N-terminal or C-terminal tail of the histones. In addition, the histone or the fragment thereof to be determined in the context of the present invention may also be modified, e.g. by post-translational modification. Exemplary post translational modifications can be acetylation, citrullination, deacetylation, methylation, demethylation, deimination, isomerization, phosphorylation and ubiquitination. Preferably, the histones or fragments thereof a circulating.

In particular aspects of the invention, a level of a histone or a fragment thereof can be determined in the sample that is not assembled in a macromolecular complex, such as a nucleosome, octamer or a neutrophil extracellular trap (NET). Such histone(s) are herein referred to as "free histone(s)". Accordingly, the level of the at least one histone may particularly be a level of at least one free histone.

The level of such free histones can be determined by the detection of amino acid sequences or structural epitopes of histones that are not accessible in an assembled stoichiometric macromolecular complex, like a mono-nucleosome or an octamer. In such structures, particular regions of the histones are covered and are thus sterically inaccessible as shown for the neutrophil extracellular traps ("NETs"). In addition, in the octamer or nucleosome, regions of histones also participate in intramolecular interactions, such as between the individual histones. Accordingly, the region/peptide/epitope of the histone that is determined in the context of the invention may determine whether the histone is a free histone or a histone that is assembled in a macromolecular complex. For example, in an immunoassay based method, the utilized antibodies may not detect histones, e.g. H4, when they are part of the octameric core of nucleosomes as the epitopes are structurally inaccessible. Herein below, regions/peptides/epitopes of the histone are exemplified that could be employed to determine a free histone. For example, regions/peptides/epitopes of the N-terminal or C-terminal tail of the histones can be employed to determine histones independent of whether they are assembled in the macromolecular complex or are free histones according to the present invention.

"Stoichiometric" in this context relates to intact complexes, e.g. a mononucleosome or an octamer. "Free histone proteins" can also comprise non-chromatin-bound histones. For example, "free histone proteins" may also comprise individual histone proteins or non-octameric histone complexes. Free histones may (e.g. transiently) be bound to individual histones, for instance, histones may form homo- or hetero-dimers. The free histones may also form homo- or hetero-tetramers. The homo- or heterotetramer may consist of four molecules of histones, e.g. H2A, H2B, H3 and/or H4. A typical heterotetramer is formed by two heterodimers, wherein each heterodimer consists of H3 and H4. It is also understood herein that a heterotetramer may be formed by H2A and H2B. It is also envisaged herein that a heterotetramer may be formed by one heterodimer consisting of H3 and H4, and one heterodimer consisting of H2A and H2B. Free histones are thus herein referred to as and can be monomeric, heterodimeric or tetrameric histone proteins, which are not assembled in a ("stoichiometric") macromolecular complex consisting of the histone octamer bound to nucleic acid, e.g. a nucleosome. In addition, free histones may also be bound to nucleic acids, and wherein said free histones are not assembled in a ("stoichiometric") macromolecular complex, e.g. an intact nucleosome. Preferably, the free histone(s) is/are essentially free of nucleic acids.

Lactate, or lactic acid, is an organic compound with the formula $CH_3CH(OH)COOH$, which occurs in bodily fluids including blood. Blood tests for lactate are performed to determine the status of the acid base homeostasis in the body. Lactic acid is a product of cell metabolism that can accumulate when cells lack sufficient oxygen (hypoxia) and must turn to a less efficient means of energy production, or when a condition causes excess production or impaired clearance of lactate. Lactic acidosis can be caused by an inadequate amount of oxygen in cells and tissues (hypoxia), for example if someone has a condition that may lead to a decreased amount of oxygen delivered to cells and tissues, such as shock, septic shock or congestive heart failure, the lactate test can be used to help detect and evaluate the severity of hypoxia and lactic acidosis.

C-reactive protein (CRP) is a pentameric protein, which can be found in bodily fluids such as blood plasma. CRP levels can rise in response to inflammation. Measuring and charting CRP values can prove useful in determining disease progress or the effectiveness of treatments.

As used herein, the "sequential organ failure assessment score" or "SOFA score" is one score used to track a patient's status during the stay in an intensive care unit (ICU). The SOFA score is a scoring system to determine the extent of a person's organ function or rate of failure. The score is based on six different scores, one each for the respiratory, cardiovascular, hepatic, coagulation, renal and neurological systems. Both the mean and highest SOFA scores being predictors of outcome. An increase in SOFA score during the first 24 to 48 hours in the ICU predicts a mortality rate of at least 50% up to 95%. Scores less than 9 give predictive mortality at 33% while above 14 can be close to or above 95%.

As used herein, the quick SOFA score (qSOFA) is a scoring system that indicates a patient's organ dysfunction or mortality risk. The score is based on three criteria: 1) an alteration in mental status, 2) a decrease in systolic blood pressure of less than 100 mm Hg, 3) a respiration rate greater than 22 breaths per minute. Patients with two or more of these conditions are at greater risk of having an organ dysfunction or to die.

As used herein, "APACHE II" or "Acute Physiology and Chronic Health Evaluation II" is a severity-of-disease classification scoring system (Knaus et al., 1985). It can be applied within 24 hours of admission of a patient to an intensive care unit (ICU) and may be determined based on 12 different physiologic parameters: AaDO2 or PaO2 (depending on FiO2), temperature (rectal), mean arterial pressure, pH arterial, heart rate, respiratory rate, sodium (serum), potassium (serum), creatinine, hematocrit, white blood cell count and Glasgow Coma Scale.

As used herein, "SAPS II" or "Simplified Acute Physiology Score II" relates to a system for classifying the severity of a disease or disorder (see Le Gall J R et al., A new Simplified Acute Physiology Score (SAPS II) based on a European/North American multicenter study. JAMA. 1993; 270(24):2957-63.). The SAPS II score is made of 12 physiological variables and 3 disease-related variables. The point score is calculated from 12 routine physiological measurements, information about previous health status and some information obtained at admission to the ICU. The SAPS II score can be determined at any time, preferably, at day 2. The "worst" measurement is defined as the measure that correlates to the highest number of points. The SAPS II score ranges from 0 to 163 points. The classification system includes the followings parameters: Age, Heart Rate, Systolic Blood Pressure, Temperature, Glasgow Coma Scale, Mechanical Ventilation or CPAP, PaO2, FiO2, Urine Output, Blood Urea Nitrogen, Sodium, Potassium, Bicarbonate, Bilirubin, White Blood Cell, Chronic diseases and Type of admission. There is a sigmoidal relationship between mortality and the total SAPS II score. The mortality of a subject is 10% at a SAPSII score of 29 points, the mortality is 25% at a SAPSII score of 40 points, the mortality is 50% at a SAPSII score of 52 points, the mortality is 75% at a SAPSII score of 64 points, the mortality is 90% at a SAPSII score of 77 points (Le Gall loc. cit.).

As used herein, the term "sample" is a biological sample that is obtained or isolated from the patient or subject. "Sample" as used herein may, e.g., refer to a sample of bodily fluid or tissue obtained for the purpose of diagnosis, prognosis, or evaluation of a subject of interest, such as a patient. Preferably herein, the sample is a sample of a bodily fluid, such as blood, serum, plasma, cerebrospinal fluid, urine, saliva, sputum, pleural effusions, cells, a cellular extract, a tissue sample, a tissue biopsy, a stool sample and the like. Particularly, the sample is blood, blood plasma, blood serum, or urine.

Embodiments of the present invention refer to the isolation of a first sample and the isolation of a second sample. In the context of the method of the present invention, the terms "first sample" and "second sample" relate to the relative determination of the order of isolation of the samples employed in the method of the present invention. When the terms first sample and second sample are used in specifying the present method, these samples are not to be considered as absolute determinations of the number of samples taken. Therefore, additional samples may be isolated from the patient before, during or after isolation of the first and/or the second sample, or between the first or second samples, wherein these additional samples may or may not be used in the method of the present invention. The first sample may therefore be considered as any previously obtained sample. The second sample may be considered as any further or subsequent sample.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

"Serum" in the context of the present invention is the liquid fraction of whole blood that is collected after the blood is allowed to clot. When coagulated blood (clotted blood) is centrifuged serum can be obtained as supernatant.

As used herein, "urine" is a liquid product of the body secreted by the kidneys through a process called urination (or micturition) and excreted through the urethra.

In preferred embodiments of the present invention the patient has been diagnosed as suffering from sepsis. More particularly, the patient may have been diagnosed as suffering from severe sepsis and/or septic shock.

"Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 April; 31(4): 1250-6). The term "sepsis" used herein includes, but is not limited to, sepsis, severe sepsis, septic shock.

The term "sepsis" used herein includes, but is not limited to, sepsis, severe sepsis, septic shock. Severe sepsis in refers to sepsis associated with organ dysfunction, hypoperfusion abnormality, or sepsis-induced hypotension. Hypoperfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypoperfusion abnormalities or organ dysfunction (Bone et al., CHEST 101(6): 1644-55, 1992).

The term sepsis may alternatively be defined as life-threatening organ dysfunction caused by a dysregulated host response to infection. For clinical operationalization, organ dysfunction can preferably be represented by an increase in the Sequential Organ Failure Assessment (SOFA) score of 2 points or more, which is associated with an in-hospital mortality greater than 10%. Septic shock may be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) in the absence of hypovolemia.

The term "sepsis" used herein relates to all possible stages in the development of sepsis.

The term "sepsis" also includes severe sepsis or septic shock based on the SEPSIS-2 definition (Bone et al., 2009). The term "sepsis" also includes subjects falling within the SEPSIS-3 definition (Singer et al., 2016). The term "sepsis" used herein relates to all possible stages in the development of sepsis.

As used herein, "infection" within the scope of the invention means a pathological process caused by the invasion of normally sterile tissue or fluid by pathogenic or potentially pathogenic agents/pathogens, organisms and/or microorganisms, and relates preferably to infection(s) by bacteria, viruses, fungi, and/or parasites. Accordingly, the infection can be a bacterial infection, viral infection, and/or fungal infection. The infection can be a local or systemic infection. For the purposes of the invention, a viral infection may be considered as infection by a microorganism.

Further, the subject suffering from an infection can suffer from more than one source(s) of infection simultaneously. For example, the subject suffering from an infection can suffer from a bacterial infection and viral infection; from a viral infection and fungal infection; from a bacterial and fungal infection, and from a bacterial infection, fungal infection and viral infection, or suffer from a mixed infection comprising one or more of the infections listed herein, including potentially a superinfection, for example one or more bacterial infections in addition to one or more viral infections and/or one or more fungal infections.

As used herein "infectious disease" comprises all diseases or disorders that are associated with bacterial and/or viral and/or fungal infections.

According to the present invention, critically ill patients, such as septic patients may need a very strict control, with respect of vital functions and/or monitoring of organ protection and may be under medical treatment.

In the context of the present invention, the term "medical treatment" or "treatment" comprises various treatments and therapeutic strategies, which comprise, without limitation, anti-inflammatory strategies, administration of proADM-antagonists such as therapeutic antibodies, si-RNA or DNA, the extracorporal blood purification or the removal of harmful substances via apheresis, dialyses, adsorbers to prevent the cytokine storm, removal of inflammatory mediators, plasma apheresis, administration of vitamines such as vitamin C, ventilation like mechanical ventilation and non-mechanical ventilation, to provide the body with sufficient oxygen, for example, focus cleaning procedures, transfusion of blood products, infusion of colloids, renal or liver replacement, antibiotic treatment, invasive mechanical ventilation, non-invasive mechanical ventilation, renal replacement therapy, vasopressor use, fluid therapy, apheresis and measures for organ protection, provision of corticosteroids, blood or platelet transfusion, transfusion of blood components, such as serum, plasma or specific cells or combinations thereof, drugs promoting the formation of thrombocytes, source control, surgeries, causative treatment or performing a splenectomy.

Further treatments of the present invention comprise the administration of cells or cell products like stem cells, blood or plasma, and the stabilization of the patients circulation and the protection of endothelial glycocalyx, for example via optimal fluid management strategies, for example to reach normovolemia and prevent or treat hypervolemia or hypovolemia. Moreover, vasopressors or e.g. catecholamine as well as albumin or heparanase inhibition via unfractionated heparin or N-desulfated re-N-acetylated heparin are useful treatments to support the circulation and endothelial layer.

Additionally, medical treatments of the present invention comprise, without limitation, stabilization of the blood clotting, iNOS inhibitors, anti-inflammatory agents like hydrocortisone, sedatives and analgetics as well as insulin.

"Renal replacement therapy" (RRT) relates to a therapy that is employed to replace the normal blood-filtering function of the kidneys. Renal replacement therapy may refer to dialysis (e.g. hemodialysis or peritoneal dialysis), hemofiltration, and hemodiafiltration. Such techniques are various ways of diverting the blood into a machine, cleaning it, and then returning it to the body. Renal replacement therapy may also refer to kidney transplantation, which is the ultimate form of replacement in that the old kidney is replaced by a donor kidney. The hemodialysis, hemofiltration, and hemodiafiltration may be continuous or intermittent and can use an arteriovenous route (in which blood leaves from an artery and returns via a vein) or a venovenous route (in which blood leaves from a vein and returns via a vein). This results in various types of RRT. For example, the renal replacement therapy may be selected from the group of, but not limited to continuous renal replacement therapy (CRRT), continuous hemodialysis (CHD), continuous arteriovenous hemodialysis (CAVHD), continuous venovenous hemodialysis (CVVHD), continuous hemofiltration (CHF), continuous arteriovenous hemofiltration (CAVH or CAVHF), continuous venovenous hemofiltration (CVVH or CVVHF), continuous hemodiafiltration (CHDF), continuous arteriovenous hemodiafiltration (CAVHDF), continuous venovenous hemodiafiltration (CVVHDF), intermittent renal replacement therapy (IRRT), intermittent hemodialysis (IHD), intermittent venovenous hemodialysis (IVVHD), intermittent hemofiltration (IHF), intermittent venovenous hemofiltration (IVVH or IVVHF), intermittent hemodiafiltration (IHDF) and intermittent venovenous hemodiafiltration (IVVHDF).

Artificial and mechanical ventilation are effective approaches to enhance proper gas exchange and ventilation and aim to save life during severe hypoxemia. Artificial ventilation relates to assisting or stimulating respiration of the subject. Artificial ventilation may be selected from the group consisting of mechanical ventilation, manual ventilation, extracorporeal membrane oxygenation (ECMO) and noninvasive ventilation (NIV). Mechanical ventilation relates to a method to mechanically assist or replace spontaneous breathing. This may involve a machine called a ventilator. Mechanical ventilation may be High-Frequency Oscillatory Ventilation or Partial Liquid Ventilation.

"Fluid management" refers to the monitoring and controlling of the fluid status of a subject and the administration of fluids to stabilize the circulation or organ vitality, by e.g. oral, enteral or intravenous fluid administration. It comprises the stabilization of the fluid and electrolyte balance or the prevention or correction of hyper- or hypovolemia as well as the supply of blood products.

Surgical emergencies/Emergency surgery are needed if a subject has a medical emergency and an immediate surgical intervention may be required to preserve survival or health status. The subject in need of emergency surgery may be selected from the group consisting of subjects suffering from acute trauma, an active uncontrolled infection, organ transplantation, organ-preventive or organ-stabilizing surgery or cancer.

Cleaning Procedures are hygienic methods to prevent subjects from infections, especially nosocomial infections, comprising desinfection of all organic and anorganic surfaces that could get in contact with a patient, such as for example, skin, objects in the patient's room, medical devices, diagnostic devices, or room air. Cleaning procedures include the use of protective clothes and units, such as mouthguards, gowns, gloves or hygiene lock, and actions like restricted patient visits. Furthermore, cleaning procedures comprise the cleaning of the patient itself and the clothes or the patient.

In the case of critical illness, such as sepsis or severe infections it is very important to have an early diagnosis as well a prognosis and risk assessment for the outcome of a patient to find the optimal therapy and management. The therapeutic approaches need to be very individual and vary from case to case. A therapeutic monitoring is needed for a best practice therapy and is influenced by the timing of treatment, the use of combined therapies and the optimization of drug dosing. A wrong or omitted therapy or management will increase the mortality rate hourly.

A medical treatment of the present invention may be an antibiotic treatment, wherein one or more "antibiotics" or "antiinfective agents" may be administered if an infection has been diagnosed or symptoms of an infectious disease have been determined.

Furthermore, antibiotic agents comprise bacteriophages for treatment of bacterial infections, synthetic antimicrobial peptides or iron-antagonists/iron chelator. Also, therapeutic antibodies or antagonist against pathogenic structures like anti-VAP-antibodies, anti-resistant clone vaccination, administration of immune cells, such as in vitro primed or modulated T-effector cells, are antibiotic agents that represent treatment options for critically ill patients, such as sepsis patients. Further antibiotic agents/treatments or therapeutic strategies against infection or for the prevention of new infections include the use of antiseptics, decontamination products, anti-virulence agents like liposomes, sanitation, wound care, surgery.

It is also possible to combine several of the aforementioned antibiotic agents or treatments strategies with fluid therapy, platelet transfusion or transfusion of blood products.

According to the present invention proADM and optionally PCT and/or other markers or clinical scores are employed as markers for therapy monitoring, comprising prognosis, prognosis, risk assessment and risk stratification of a subsequent adverse event in the health of a patient which has been diagnosed as being critically ill.

A skilled person is capable of obtaining or developing means for the identification, measurement, determination and/or quantification of any one of the above proADM molecules, or fragments or variants thereof, as well as the other markers of the present invention according to standard molecular biological practice.

The level of proADM or fragments thereof as well as the levels of other markers of the present invention can be determined by any assay that reliably determines the concentration of the marker. Particularly, mass spectrometry (MS) and/or immunoassays can be employed as exemplified in the appended examples. As used herein, an immunoassay is a biochemical test that measures the presence or concentration of a macromolecule/polypeptide in a solution through the use of an antibody or antibody binding fragment or immunoglobulin.

Methods of determining proADM or other the markers such as PCT used in the context of the present invention are intended in the present invention. By way of example, a method may be employed selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

Determination of proADM and optionally other markers based on antibody recognition is a preferred embodiment of the invention. As used herein, the term, "antibody" refers to immunoglobulin molecules and immunologically active portions of immunoglobulin (Ig) molecules, i.e., molecules that contain an antigen binding site that specifically binds (immuno reacts with) an antigen. According to the invention, the antibodies may be monoclonal as well as polyclonal antibodies. Particularly, antibodies that are specifically binding to at lest proADM or fragments thereof are used.

An antibody is considered to be specific, if its affinity towards the molecule of interest, e.g. proADM, or the fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. In the context of the invention, monoclonal antibodies are preferred. The antibody or the antibody binding fragment binds specifically to the herein defined markers or fragments thereof. In particular, the antibody or the antibody binding fragment binds to the herein defined peptides of proADM. Thus, the herein defined peptides can also be epitopes to which the antibodies specifically bind. Further, an antibody or an antibody binding fragment is used in the methods and kits of the invention that binds specifically to proADM or proADM, particularly to MR-proADM.

Further, an antibody or an antibody binding fragment is used in the methods and kits of the invention that binds specifically to proADM or fragments thereof and optionally to other markers of the present inventions such as PCT. Exemplary immunoassays can be luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, rare cryptate assay. Further, assays suitable for point-of-care testing and rapid test formats such as for instance immune-chromatographic strip tests can be employed. Automated immunoassays are also intended, such as the KRYPTOR assay.

Alternatively, instead of antibodies, other capture molecules or molecular scaffolds that specifically and/or selectively recognize proADM may be encompassed by the scope of the present invention. Herein, the term "capture molecules" or "molecular scaffolds" comprises molecules which may be used to bind target molecules or molecules of interest, i.e. analytes (e.g. proADM, proADM, MR-proADM, and PCT), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may, for instance, be mediated by ionic, van-der-Waals, pi-pi, sigma-pi, hydrophobic or hydrogen bond interactions or a combination of two or more of the aforementioned interactions or covalent interactions between the capture molecules or molecular scaffold and the target molecules or molecules of interest. In the context of the present invention, capture molecules or molecular scaffolds may for instance be selected from the group consisting of a nucleic acid molecule, a carbohydrate molecule, a PNA molecule, a protein, a peptide and a glycoprotein. Capture molecules or molecular scaffolds include, for example, aptamers, DARpins (Designed Ankyrin Repeat Proteins). Affimers and the like are included.

In certain aspects of the invention, the method is an immunoassay comprising the steps of:
a) contacting the sample with
   i. a first antibody or an antigen-binding fragment or derivative thereof specific for a first epitope of said proADM, and
   ii. a second antibody or an antigen-binding fragment or derivative thereof specific for a second epitope of said proADM; and
b) detecting the binding of the two antibodies or antigen-binding fragments or derivates thereof to said proADM.

Preferably, one of the antibodies can be labeled and the other antibody can be bound to a solid phase or can be bound selectively to a solid phase. In a particularly preferred aspect of the assay, one of the antibodies is labeled while the other is either bound to a solid phase or can be bound selectively to a solid phase. The first antibody and the second antibody can be present dispersed in a liquid reaction mixture, and wherein a first labeling component which is part of a labeling system based on fluorescence or chemiluminescence extinction or amplification is bound to the first antibody, and a second labeling component of said labeling system is bound to the second antibody so that, after binding of both antibodies to said proADM or fragments thereof to be detected, a measurable signal which permits detection of the resulting sandwich complexes in the measuring solution is generated. The labeling system can comprise a rare earth cryptate or chelate in combination with a fluorescent or chemiluminescent dye, in particular of the cyanine type.

In a preferred embodiment, the method is executed as heterogeneous sandwich immunoassay, wherein one of the antibodies is immobilized on an arbitrarily chosen solid phase, for example, the walls of coated test tubes (e.g. polystyrol test tubes; coated tubes; CT) or microtiter plates, for example composed of polystyrol, or to particles, such as for instance magnetic particles, whereby the other antibody has a group resembling a detectable label or enabling for selective attachment to a label, and which serves the detection of the formed sandwich structures. A temporarily delayed or subsequent immobilization using suitable solid phases is also possible.

The method according to the present invention can furthermore be embodied as a homogeneous method, wherein the sandwich complexes formed by the antibody/antibodies and the marker, proADM or a fragment thereof, which is to be detected remains suspended in the liquid phase. In this case it is preferred, that when two antibodies are used, both antibodies are labeled with parts of a detection system, which leads to generation of a signal or triggering of a signal if both antibodies are integrated into a single sandwich. Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733, EP0180492 or EP0539477 and the prior art cited therein. In this way, measurements in which only reaction products comprising both labeling components in a single immune-complex directly in the reaction mixture are detected, become possible. For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of proADM or fragments thereof and/or the level of any further marker of the herein provided method, such as PCT, is determined. In particular preferred aspects, the diagnostic device is KRYPTOR®.

The level of the marker of the present invention, e.g. the proADM or fragments thereof, PCT or fragments thereof, or other markers, can also be determined by a mass spectrometric (MS) based methods. Such a method may comprise detecting the presence, amount or concentration of one or more modified or unmodified fragment peptides of e.g. proADM or the PCT in said biological sample or a protein digest (e.g. tryptic digest) from said sample, and optionally separating the sample with chromatographic methods, and subjecting the prepared and optionally separated sample to MS analysis. For example, selected reaction monitoring (SRM), multiple reaction monitoring (MRM) or parallel reaction monitoring (PRM) mass spectrometry may be used in the MS analysis, particularly to determine the amounts of proADM or fragments thereof.

Herein, the term "mass spectrometry" or "MS" refers to an analytical technique to identify compounds by their mass. In order to enhance the mass resolving and mass determining capabilities of mass spectrometry, the samples can be processed prior to MS analysis. Accordingly, the invention relates to MS detection methods that can be combined with immuno-enrichment technologies, methods related to sample preparation and/or chromatographic methods, preferably with liquid chromatography (LC), more preferably with high performance liquid chromatography (HPLC) or ultra high performance liquid chromatography (UHPLC). Sample preparation methods comprise techniques for lysis, fractionation, digestion of the sample into peptides, depletion, enrichment, dialysis, desalting, alkylation and/or peptide reduction. However, these steps are optional. The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The skilled person is aware how quantify the level of a marker in the sample by mass spectrometric methods. For example, relative quantification "rSRM" or absolute quantification can be employed as described above.

Moreover, the levels (including reference levels) can be determined by mass spectrometric based methods, such as methods determining the relative quantification or determining the absolute quantification of the protein or fragment thereof of interest.

Relative quantification "rSRM" may be achieved by:
1. Determining increased or decreased presence of the target protein by comparing the SRM (Selected reaction monitoring) signature peak area from a given target fragment peptide detected in the sample to the same SRM signature peak area of the target fragment peptide in at least a second, third, fourth or more biological samples.
2. Determining increased or decreased presence of target protein by comparing the SRM signature peak area from a given target peptide detected in the sample to SRM signature peak areas developed from fragment peptides from other proteins, in other samples derived from different and separate biological sources, where the SRM signature peak area comparison between the two samples for a peptide fragment are normalized for e.g to amount of protein analyzed in each sample.
3. Determining increased or decreased presence of the target protein by comparing the SRM signature peak area for a given target peptide to the SRM signature peak areas from other fragment peptides derived from different proteins within the same biological sample in order to normalize changing levels of histones protein to levels of other proteins that do not change their levels of expression under various cellular conditions.
4. These assays can be applied to both unmodified fragment peptides and to modified fragment peptides of the target proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:
1. Comparing the SRM/MRM signature peak area for a given fragment peptide from the target proteins in an individual biological sample to the SRM/MRM signature peak area of an internal fragment peptide standard spiked into the protein lysate from the biological sample. The internal standard may be a labeled synthetic version of the fragment peptide from the target protein that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (e.g. mono-, di-, or tri-methylation), citrullination, ubiquitinylation, and where the absolute levels of modified peptides can be determined in the same manner as determining absolute levels of unmodified peptides.
2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, reverse curve method circumvents the issue of endogenous analyte in the matrix, where a constant amount of light peptide is spiked on top of the endogenous analyte to create an internal standard and varying amounts of heavy peptide are spiked to create a set of concentration standards. Test samples to be compared with either the normal or reverse curves are spiked with the same amount of standard peptide as the internal standard spiked into the matrix used to create the calibration curve.

The invention further relates to kits, the use of the kits and methods wherein such kits are used. The invention relates to kits for carrying out the herein above and below provided methods. The herein provided definitions, e.g. provided in relation to the methods, also apply to the kits of the invention. In particular, the invention relates to kits for therapy monitoring, comprising the prognosis, risk assessment or risk stratification of a subsequent adverse event in the health of a patient, wherein said kit comprises detection reagents for determining the level proADM or fragment(s) thereof, and optionally additionally for determining the level of PCT, lactate and/or C-reactive protein or fragment(s) thereof, in a sample from a subject, and—detection reagents for determining said level of proADM in said sample of said subject, and reference data, such as a reference level, corresponding to high and/or low severity levels of proADM, wherein the low severity level is below 4 nmol/l, preferably below 3 nmol/l, more preferably below 2.7 nmol/l, and the high severity level is above 6.5 nmol/l, preferably above 6.95 nmol/l, more preferably above 10.9 nmol/l, and optionally PCT, lactate and/or C-reactive protein levels, wherein said reference data is preferably stored on a computer readable medium and/or employed in the form of computer executable code configured for comparing the determined levels of proADM or fragment(s) thereof, and optionally additionally the determined levels of PCT, lactate and/or C-reactive protein or fragment(s) thereof, to said reference data.

As used herein, "reference data" comprise reference level(s) of proADM and optionally PCT, lactate and/or C-reactive protein. The levels of proADM and optionally PCT, lactate and/or C-reactive protein in the sample of the subject can be compared to the reference levels comprised in the reference data of the kit. The reference levels are herein described above and are exemplified also in the appended examples. The reference data can also include a reference sample to which the level of proADM and optionally PCT, lactate and/or C-reactive protein is compared. The reference data can also include an instruction manual how to use the kits of the invention.

The kit may additionally comprise items useful for obtaining a sample, such as a blood sample, for example the kit may comprise a container, wherein said container comprises a device for attachment of said container to a cannula or syringe, is a syringe suitable for blood isolation, exhibits an internal pressure less than atmospheric pressure, such as is suitable for drawing a pre-determined volume of sample into said container, and/or comprises additionally detergents, chaotropic salts, ribonuclease inhibitors, chelating agents, such as guanidinium isothiocyanate, guanidinium hydrochloride, sodium dodecylsulfate, polyoxyethylene sorbitan monolaurate, RNAse inhibitor proteins, and mixtures thereof, and/or A filter system containing nitro-cellulose, silica matrix, ferromagnetic spheres, a cup retrieve spill over, trehalose, fructose, lactose, mannose, poly-ethylenglycol, glycerol, EDTA, TRIS, limonene, xylene, benzoyl, phenol, mineral oil, anilin, pyrol, citrate, and mixtures thereof.

As used herein, the "detection reagent" or the like are reagents that are suitable to determine the herein described marker(s), e.g. of proADM, PCT, lactate and/or C-reactive protein. Such exemplary detection reagents are, for example, ligands, e.g. antibodies or fragments thereof, which specifically bind to the peptide or epitopes of the herein described marker(s). Such ligands might be used in immunoassays as described above. Further reagents that are employed in the immunoassays to determine the level of the marker(s) may also be comprised in the kit and are herein considered as detection reagents. Detection reagents can also relate to reagents that are employed to detect the markers or fragments thereof by MS based methods. Such detection reagent can thus also be reagents, e.g. enzymes, chemicals, buffers, etc, that are used to prepare the sample for the MS analysis. A mass spectrometer can also be considered as a detection reagent. Detection reagents according to the invention can also be calibration solution(s), e.g. which can be employed to determine and compare the level of the marker(s).

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having an infection and "disease" populations, e.g. subjects having an infection. For any particular marker (like proADM), a distribution of marker levels for subjects with and without a disease/condition will likely overlap. Under such conditions, a test does not absolutely distinguish normal from disease with 100% accuracy, and the area of overlap might indicate where the test cannot distinguish normal from disease. A threshold is selected, below which the test is considered to be abnormal and above which the test is considered to be normal or below or above which the test indicates a specific condition, e.g. infection. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art; see, e.g., Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

Accordingly, the invention comprises the administration of an antibiotic suitable for treatment on the basis of the information obtained by the method described herein.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

Thus, the terms "comprising"/"including"/"having" mean that any further component (or likewise features, integers, steps and the like) can/may be present. The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The present invention is further described by reference to the following non-limiting examples.

EXAMPLES

Methods of the Examples

Study Design and Patients:

This study is a secondary analysis of the Placebo-Controlled Trial of Sodium Selenite and Procalcitonin Guided Antimicrobial Therapy in Severe Sepsis (SISPCT), which was performed across 33 multidisciplinary intensive care units (ICUs) throughout Germany from November 2009 until February 2013 (26). Eligibility criteria included adult patients ≥18 years presenting with new onset severe sepsis or septic shock (≤24 hours), according to the SEPSIS-1 definition of the ACCP/SCCM Consensus Conference Committee, and further classified according to the 2016 definitions (sepsis-3 and septic shock-3) (4). Details of the study design, data collection and management were described previously (26). The ethics committee of Jena University Hospital and all other centres approved the study and written informed consent was obtained whenever necessary.

Biomarker Measurements:

Patients were enrolled up to 24 hours after diagnosis of severe sepsis or septic shock and PCT, CRP and lactate measured immediately thereafter. PCT was measured on devices with a measuring range of 0.02-5000 ng/ml, and a functional assay sensitivity and lower detection limit of at least 0.06 ng/ml and 0.02 ng/ml, respectively. Additional blood samples from all patients were collected and stored at the central study laboratory in Jena at −80° C. MR-proADM plasma concentrations were measured retrospectively (Kryptor®, Thermo Fisher Scientific, Germany) with a limit of detection of 0.05 nmol/L. Clinical severity scores including the Sequential Organ Failure Assessment (SOFA), Acute Physiological and Chronic Health Evaluation (APACHE) II and Simplified Acute Physiological (SAPS) II score were taken upon study enrollment.

Statistical Analysis:

Differences in demographic and clinical characteristics with regards to 28 day mortality were assessed using the $\chi 2$ test for categorical variables, and Student's t-test or Mann-Whitney U test for continuous variables, depending on distribution normality. Normally and non-normally distributed variables were expressed as mean (standard deviation) and median [first quartile-third quartile], respectively. The association between mortality and each biomarker and clinical score at all time points was assessed using area under the receiver operating characteristic curves (AUROC) and Cox regression analysis, with multivariate analysis corrected for age and the presence of comorbidities and septic shock. Patients were further classified into three severity subgroups (low, intermediate and high) based on the calculation of two AUROC cut-offs across the total population for each biomarker and clinical score at each time point, with a pre-defined sensitivity and specificity of close to 90%. A subgroup clinically stable patients was subsequently identified with an absence of any ICU associated procedures or complications (including focus cleaning procedures, emergency surgery, the emergence of new infections, transfusion of blood products, infusion of colloids, invasive mechanical ventilation, renal/liver replacement or vasopressor therapy and a deterioration in the patient's general clinical signs and symptoms), and a further group identified with corresponding low MR-proADM concentrations which had not shown any increase since the previous measurement. Mortality rates and average lengths of stay were calculated in both groups and compared against the patient group who were discharged at each specific time point.

Finally, two models stratifying patients with PCT changes of 20% (baseline to day 1, based on average PCT decreases observed over this time period) and 50% (baseline to day four, based on a previously constructed model (26)) were constructed. Patient subgroups were subsequently identified based on MR-proADM severity levels, and respective mortality rates calculated. The risk of mortality within each subgroup was calculated by Cox regression analysis and illustrated by Kaplan-Meier curves. The predicted risk of developing new infections and the requirement for focus cleaning procedures and emergency surgery over days 4 to 7 were subsequently investigated in the baseline to day 4 model. All data were analysed using the statistics software R (version 3.1.2).

Example 1: Patient Characteristics

Patient characteristics upon study enrollment are summarized in Table 1.

A total of 1089 patients with either severe sepsis (13.0%) or septic shock (87.0%) were analysed, with 445 (41.3%) and 633 (58.7%) patients also satisfying the criteria for sepsis-3 and septic shock-3, respectively. Enrolled patients had an average age of 65.7 (13.7) years and a mean SOFA score of 10.0 (3.3) points. The 28 day all-cause mortality rate (N=1076) was 26.9% (sepsis-3: 20.0%; septic shock-3: 32.1%), with a hospital mortality rate of 33.4% (sepsis-3: 24.4%; septic shock-3: 40.4%). Infections originating from a single focus were found in 836 patients (77.7%), with pneumological (N=324; 30.1%), intra-abdominal (N=252; 23.4%), urogenital (N=57; 5.3%) and bone/soft tissue (N=50; 4.6%) origins most prevalent. Corresponding mortality rates were 26.5%, 24.6%, 22.8% and 28.0%, respectively. Multiple origins of infection were found in 240 (22.3%) patients. The most common causes of mortality included sepsis induced multiple organ failure (N=132; 45.7%), refractory septic shock (N=54; 18.7%), death due to pre-existing illness (N=35; 12.1%) and acute respiratory insufficiency (N=17; 5.9%). Other causes such as cardiogenic and hemorrhagic shock, pulmonary embolism, cerebral oedema, myocardial infarction and cardiac arrhythmia accounted for a combined mortality rate of 8.6%. A limitation of therapy was applied to 3.4% of patients.

Example 2: Association of Baseline Biomarkers and Clinical Scores with Mortality Univariate and multivariate Cox regression analysis found that MR-proADM had the strongest association with 28 day mortality across the total patient population, as well as within the sepsis-3 and septic shock-3 subgroups (Table 2). Corresponding AUROC analysis found significant differences in all biomarker and clinical score comparisons with MR-proADM, apart from APACHE II (sepsis-3 patient subgroup).

Similar results were also found for 7 day, 90 day, ICU and hospital mortality prediction (Table 3), with the addition of MR-proADM to all potential biomarkers and clinical score combinations (N=63) significantly increasing prognostic capability (Table 4).

Example 3: Identification of High-Risk Patients

The total patient population was further stratified according to existing SOFA severity levels, and biomarker and clinical score performance in predicting 28 day mortality assessed in each subgroup. MR-proADM showed the highest accuracy of all parameters in the low (SOFA≤7) and moderate (8≤SOFA 13) severity SOFA subgroups (Table 5; Table 6).

Two corresponding MR-proADM cut-offs were subsequently calculated to identify low (≤2.7 nmol/L) and high (>10.9 nmol/L) severity subgroups at baseline. Compared to SOFA, a more accurate reclassification could be made at both low (MR-proADM vs. SOFA: N=265 vs. 232; 9.8% vs. 13.8% mortality) and high (MR-proADM vs. SOFA: N=161 vs. 155; 55.9% vs. 41.3%) severity cut-offs (Table 7).

A subgroup of 94 patients (9.3%) with high MR-proADM concentrations and corresponding low or intermediate SOFA had 28 and 90 day mortality rates of 57.4% and 68.9%, respectively, compared to 19.8% and 30.8% in the remaining patient population with low and intermediate SOFA values. Similar patterns could be found for SAPS II, APACHE II and lactate, respectively (Tables 8-10).

Example 4: Identification of Low Risk Patients Throughout ICU Stay

The study cohort comprises a subset of clinically stable patients that did not face ICU related procedures or complications, such as focus cleaning procedures, emergency surgery, new infections, transfusion of blood products, infusion of colloids, invasive mechanical ventilation, renal/liver replacement, deterioration in the patient's general clinical signs and symptoms. This group of clinically stable patients was categorized as low risk patients.

MR-proADM showed the strongest association with 28 day mortality across all subsequent time points (Table 11), and could provide a stable cut-off of ≤2.25 nmol/L in identifying a low risk patient population, resulting in the classification of greater patient numbers with lower mortality rates compared to other biomarkers and clinical scores (Table 12). Accordingly, 290 low MR-proADM severity patients could be identified on day 4, of which 79 (27.2%) were clinically stable and had no increase in MR-proADM concentrations from the last measurement (Table 13). A continuously low MR-proADM concentration could be found in 51 (64.6%) patients, whilst a decrease from an intermediate to low level severity level could be observed in 28 (35.4%) patients. The average ICU length of stay was 8 [7-10] days, with a 28 and 90 day mortality rate of 0.0% and 1.4%, respectively. In comparison, only 43 patients were actually discharged from the ICU on day 4, with a 28 and 90 day mortality rate of 2.3% and 10.0%. Analysis of the MR-proADM concentrations within this group of patients indicated a range of values, with 20 (52.6%), 16 (42.1%) and 2 (5.3%) patients having low, intermediate and high severity concentrations, respectively. Similar results were found for patients remaining on the ICU on days 7 and 10.

MR-proADM with a stable cut-off of 2.25 nmol/L could identify a greater number of low risk patients with lower mortality rates compared to other biomarkers and clinical scores. Based on that finding more patients could be discharged from the ICU compared to classifications without using ADM. By discharging more patients, the hospital can more efficiently occupy ICU beds and benefits from avoided costs.

Example 5: Additional Impact of MR-proADM on Procalcitonin Guided Therapy

Time-dependent Cox regression analysis indicated that the earliest significant additional increase in prognostic information to MR-proADM baseline values could be observed on day 1, with subsequent single or cumulative measurements resulting in significantly stronger associations with 28 day mortality (Table 14). Hence two PCT guided algorithm models were constructed investigating PCT changes from baseline to either day 1 or day 4, with corresponding subgroup analysis based on MR-proADM severity classifications.

Patients with decreasing PCT concentrations of ≥20% from baseline to day 1 (Table 15 and Table 16) or ≥50% from baseline to day 4 (Table 17 and Table 18) were found to have 28 day mortality rates of 18.3% (N=458) and 17.1% (N=557), respectively. This decreased to 5.6% (N=125) and 1.8% (N=111) when patients had continuously low levels of MR-proADM, although increased to 66.7% (N=27) and 53.8% (N=39) in patients with continuously high MR-proADM values (HR [95% CI]: 19.1 [8.0-45.9] and 43.1 [10.1-184.0]).

Furthermore, patients with decreasing PCT values of ≥50% (baseline to day 4), but continuously high or intermediate MR-proADM concentrations, had a significantly greater risk of developing subsequent nosocomial infections (HR [95% CI]: high concentrations: 3.9 [1.5-10.5]; intermediate concentrations: 2.4 [1.1-5.1] vs. patients with continuously low concentrations; intermediate concentrations: 2.9 [1.2-6.8]) vs. decreasing intermediate to low concentrations), or requiring emergency surgery (HR [95% CI]: intermediate concentrations: 2.0 [1.1-3.7] vs. decreasing intermediate to low concentrations). Conversely, patients with increasing intermediate to high concentrations were more likely to require cleaning of the infectious origin compared to those with continuously intermediate (HR [95% CI]: 3.2 [1.3-7.6]), or decreasing (HR [95% CI]: intermediate to low: 8.7 [3.1-24.8]); high to intermediate: 4.6 [1.4-14.5]) values. When PCT levels failed to decrease by ≥50%, a significantly increased risk of requiring emergency surgery was observed if MR-proADM concentrations were either at a continuously high (HR [95% CI]: 5.7 [1.5-21.9]) or intermediate (HR [95% CI]: 4.2 [1.3-13.2]) level, as opposed to being continuously low.

Example 6: Association of Baseline Biomarkers and Clinical Scores with Mortality MR-proADM showed the strongest association in patients with pneumological and intra-abdominal infections, as well as in patients with Gram positive infections, irrespective of the infectious origin (Tables 19-20). When patients were grouped according to operative emergency, non-operative emergency and elective surgery history resulting in admission to the ICU, MR-proADM provided the strongest and most balanced association with 28 day mortality across all groups (Table 21).

Example 7: Correlation of Biomarkers and Clinical Scores with SOFA at Baseline and Day 1

MR-proADM had the greatest correlation of all biomarkers with the SOFA score at baseline, which was significantly increased when baseline values were correlated with day 1 SOFA scores. The greatest correlation could be found between MR-proADM and SOFA on day 10, with differences between individual SOFA subscores found throughout (Tables 22-24).

Example 8: Identification of High-Risk Patients

Similar results could be found in a subgroup of 124 patients (12.0%) with high MR-proADM concentrations and either low or intermediate SAPS II values (High MR-proADM subgroup: [54.8% and 65.6% mortality]; remaining SAPS II population [19.7% and 30.0% mortality]), as well as in 109 (10.6%) patients with either low or intermediate APACHE II values (High MR-proADM subgroup: [56.9% and 66.7% mortality]; remaining APACHE II population: [19.5% and 30.3% mortality]).

Example 9: Improved Procalcitonin (PCT) Guided Therapy by Combining PCT and ADM Two PCT guided algorithm models were constructed investigating PCT changes from baseline to either day 1 or day 4, with corresponding subgroup analysis based on MR-proADM severity classifications (Tables 25-30).

The previous examples show an add-on value for ADM in patients having a PCT decrease at <20% or <50%, as well as in patients where PCT decreased by ≥20% or ≥50%. However, additional analysis demonstrates that ADM can be an add-on regardless of % of decrease or even increase of PCT. Decreasing PCT values could reflect patients where the antibiotic treatment appears to be working, therefore the clinician thinks they are on a good way to survival (i.e. kill the root cause of the sepsis—the bacteria—should result in the patient getting better).

For example, some patients have decreasing PCT levels from baseline (day of admission) to day 1 with a 28d mortality rate of 19%. By additionally measuring ADM, you can conclude from patients with low ADM a much higher chance of survival or much lower probability to die (Table 25; compare 19% mortality rate decreasing PCT only vs. 5% mortality rate PCT+low ADM). By having a reduced risk of dying, patients could be discharged from ICU with more confidence, or fewer diagnostic tests are required (i.e. you know they are on a good path to recovery).

On the other hand, new measures need to be considered for those with a high ADM value. They are at a much higher risk with regard to mortality (compare 19% mortality rate decreasing PCT only vs 58.8% mortality rate PCT+high ADM). The physician thinks the patient is getting better due to the decrease in PCT value, but in fact the ADM concentration remains the same. It can be therefore concluded that treatment isn't working, and needs to be adapted as soon as possible).

In a similar way, ADM can help to stratify those patients with increasing PCT values (Table 25).

Development of New Infections

PCT and MR-proADM changes were analyzed in two models, either from baseline to day 1, or from baseline to day 4. Patients were grouped according to overall PCT changes and MR-proADM severity levels.

The number of new infections over days 1, 2, 3 and 4 (Table 26) and over days 4, 5, 6 and 7 (Table 27) were subsequently calculated in each patient who was present on day 1 or day 4 respectively. In some cases, patients were discharged during the observation period. It is assumed that no new infections were developed after release. Patients with multiple infections over the observation days were counted as a single new infection.

As a clinical consequence, patients with high MR-proADM concentrations should potentially be treated with a broad-spectrum antibiotic on ICU admission, in conjunction with others, in order to stop the development on new infections. Special care should be taken with these patients due to their high susceptibility to pick up new infections.

Requirement for Focus Cleaning

PCT and MR-proADM changes were analyzed in two models, either from baseline to day 1, or from baseline to day 4. Patients were grouped according to overall PCT changes and MR-proADM severity levels.

The number of focus cleaning events over days 1, 2, 3 and 4 (Table 28) and over days 4, 5, 6 and 7 (Table 29) were subsequently calculated in each patient who was present on day 1 or day 4 respectively. In some cases, patients were discharged during the observation period.

Requirement of Emergency Surgery

PCT and MR-proADM changes were analyzed in two models, either from baseline to day 1, or from baseline to day 4. Patients were grouped according to overall PCT changes and MR-proADM severity levels.

The number of emergency surgery requirements/events over days 1, 2, 3 and 4 (Table 30) were subsequently calculated in each patient who was present on day 1. In some cases, patients were discharged during the observation period.

Example 10: Requirement for Antibiotic Change or Modification

When combined within a PCT guided antibiotic algorithm, MR-proADM can stratify those patients who will require a future change or modification in antibiotic therapy, from those who will not.

PCT and MR-proADM changes were analyzed in two models, either from baseline to day 1, or from baseline to day 4. Patients were grouped according to overall PCT changes and MR-proADM severity levels.

The percentage of antibiotic changes on day 4 required for each patient group was subsequently calculated (Tables 31 and 32).

In Patients with Decreasing PCT Values ≥50%

Patients with increasing MR-proADM concentrations, from a low to intermediate severity level, were more likely to require a modification in antibiotic therapy on day 4 than those who had continuously low levels (Odds Ration [95% CI]: 1.5 [0.6-4.1]).

In Patients with Decreasing PCT Values <50%

Patients with either increasing MR-proADM concentrations, from an intermediate to high severity level, or continuously high concentrations, were also more likely to require changes in their antibiotic therapy on day 4 than patients with continuously low MR-proADM concentrations (Odds Ratio [95% CI]: 5.9 [1.9-18.1] and 2.9 [0.8-10.4], respectively).

Conclusion

Despite increasing PCT concentrations, either from baseline to day 1, or baseline to day 4, patients with continuously low MR-proADM concentrations had significantly lower modifications made to their prescribed antibiotic treatment than those with continuously intermediate or high concentrations. As a clinical consequence, when faced with increasing PCT concentrations, a physician should check the patient's MR-proADM levels before deciding on changing antibiotics. Those with low MR-proADM concentrations should be considered for either an increased dose or increased strength of the same antibiotic before changes are considered. Those with higher MR-proADM concentrations should be considered for earlier antibiotic changes (i.e. on days 1 to 3, as opposed to day 4).

Example 11: Identification of Patients with Abnormal Platelet Levels and Identification of High Risk Patients with Thrombocytopenia (Tables 33, 34 and 35)

Proadrenomedullin and Procalcitonin levels were measured and analyzed with regard to thrombocyte count, mortality rate and platelet transfusion at baseline and day 1. Increasing proADM and PCT concentrations correlate with decreasing platelet numbers and platelet numbers (<150.000 per μl) that reflect thrombocytopenia. The strongest decrease of platelet count was observed in patients with the highest proADM levels at baseline. Moreover increased proADM and PCT concentrations were in line with patients who required a platelet transfusion therapy. It could also confirmed that a higher mortality rate is associated with patients having thrombocytopenia and increased proADM (>6 nmol/L) and PCT (>7 ng/ml) levels.

Pro-ADM levels were investigated in patients who had normal thrombocyte levels at baseline to see if increasing proADM could predict thrombocytopenia. 39.4% of patients with continually elevated proADM levels at baseline and on day 1(proADM>10.9 nmol/l) developed thrombocytopenia. 25.6% of patients with increased proADM levels at baseline (proADM>2.75 nmol/L) and on day 1 (proADM>9.5 nmol/L) developed thrombocytopenia. 14.7% of patients with continually low proADM level at baseline and on day 1 (proADM 2.75 nmol/L) developed thrombocytopenia. The increased level of proADM correlated with the severity of the thrombocytopenic event and the associated increased mortality rate (proADM>10.9 nmol/L mortality rate of 51%; proADM 2.75 nmol/L mortality rate 9.1%).

Example 11 refers to tables 33-35.

Discussion of Examples

An accurate and rapid assessment of disease severity is crucial in order to initiate the most appropriate treatment at the earliest opportunity. Indeed, delayed or insufficient treatment may lead to a general deterioration in the patient's clinical condition, resulting in further treatment becoming less effective and a greater probability of a poorer overall outcome (8, 27). As a result, numerous biomarkers and clinical severity scores have been proposed to fulfil this unmet clinical need, with the Sequential Organ Failure Assessment (SOFA) score currently highlighted as the most appropriate tool, resulting in its central role in the 2016 sepsis-3 definition (4). This secondary analysis of the SIS-PCT trial (26), for the first time, compared sequential measurements of conventional biomarkers and clinical scores, such as lactate, procalcitonin (PCT) and SOFA, with those of the microcirculatory dysfunction marker, MR-proADM, in a large patient population with severe sepsis and septic shock.

Our results indicate that the initial use of MR-proADM within the first 24 hours after sepsis diagnosis resulted in the strongest association with short, mid and long-term mortality compared to all other biomarkers or scores. Previous studies largely confirm our findings (17, 28, 29), however conflicting results (30) may be explained in part by the smaller sample sizes analysed, as well as other factors highlighted within this study, such as microbial species, origin of infection and previous surgical history preceding sepsis development, all of which may influence biomarker performance, thus adding to the potential variability of results in small study populations. Furthermore, our study also closely confirms the results of a previous investigation (17), highlighting the superior performance of MR-proADM in low and intermediate organ dysfunction severity patients. Indeed, Andaluz-Ojeda et al. (17) place significant importance on the patient group with low levels of organ dysfunction, since "this group represents either the earliest presentation in the clinical course of sepsis and/or the less severe form of the disease". Nevertheless, a reasonable performance could be maintained across all severity groups with respect to mortality prediction, which was also the case across both patient groups defined according to the sepsis-3 and septic shock-3 criteria.

Analysis of the sequential measurements taken after onset of sepsis allowed for the identification of specific patients groups based on disease severity. The identification of both low and high-risk patients was of significant interest in our analysis. In many ICUs, the demand for ICU beds can periodically exceed availability, which may lead to an inadequate triage, a rationing of resources, and a subsequent decrease in the likelihood of correct ICU admission (32-35). Consequently, an accurate assessment of patients with a low risk of hospital mortality that may be eligible for an early ICU discharge to a step down unit may be of significant benefit. At each time point measured within our study, MR-proADM could identify a higher number of low severity patients with the lowest ICU, hospital and 28 day mortality rates. Further analysis of the patient group with a low severity and no further ICU specific therapies indicated that an additional 4 days of ICU stay were observed at each time point after biomarker measurements were taken. When compared to the patient population who were actually discharged at each time point, a biomarker driven approach to accurately identify low severity patients resulted in decreased 28 and 90 day mortality rates. Indeed, patients who were discharged had a variety of low, intermediate and high severity MR-proADM concentrations, which was subsequently reflected in a higher mortality rate. It is, however, unknown whether a number of patients within this group still required further ICU treatment for non-microcirculatory, non-life threatening issues, or that beds in a step down unit were available. Nevertheless, such a biomarker driven approach to ICU discharge in addition to clinician judgement may improve correct stratification of the patient, with accompanied clinical benefits and potential cost savings.

Conversely, the identification of high-risk patients who may require early and targeted treatment to prevent a subsequent clinical deterioration may be of even greater clinical relevance. Substantial cost savings and reductions in antibiotic use have already been observed following a PCT guided algorithm in the SISPCT study and other trials (26, 36, 37), however relatively high mortality rates can still be observed even when PCT values appear to be decreasing steadily. Our study revealed that the addition of MR-proADM to the model of PCT decreases over subsequent ICU days allowed the identification of low, intermediate and high risk patient groups, with increasing and decreasing MR-proADM severity levels from baseline to day 1 providing a sensitive and early indication as to treatment success. In addition, the prediction of the requirement for future focus cleaning or emergency surgery, as well as the susceptibility for the development of new infections, may be of substantial benefit in initiating additional therapeutic and interventional strategies, thus attempting to prevent any future clinical complications at an early stage.

The strength of our study includes the thorough examination of several different subgroups with low and high disease severities from a randomized trial database, adjusting for potential confounders and including the largest sample size of patients with sepsis, characterized by both SEPSIS 1 and 3 definitions, and information on MR-proADM kinetics. In conclusion, MR-proADM outperforms other biomarkers and clinical severity scores in the ability to identify mortality risk in patients with sepsis, both on initial diagnosis and over the course of ICU treatment. Accordingly, MR-proADM may be used as a tool to identify high severity patients who may require alternative diagnostic and therapeutic interventions, and low severity patients who may potentially be eligible for an early ICU discharge in conjunction with an absence of ICU specific therapies.

Tables

TABLE 1

Patient characteristics at baseline for survival up to 28 days

| | Total (N = 1076) | Survivors (N = 787) | Non-Survivors (N = 289) | P value |
|---|---|---|---|---|
| Age (years) (mean, S.D.) | 65.7 (13.7) | 64.3 (14.0) | 69.5 (12.0) | <0.0001 |
| Male gender (n, %) | 681 (63.3%) | 510 (64.8%) | 171 (59.2%) | 0.0907 |
| Definitions of sepsis and length of stay | | | | |
| Severe sepsis (n, %) | 139 (12.9%) | 109 (13.9%) | 30 (10.4%) | 0.1251 |
| Septic shock (n, %) | 937 (87.1%) | 678 (86.2%) | 259 (89.6%) | 0.1251 |
| Sepsis-3 (n, %) | 444 (41.3%) | 356 (45.4%) | 88 (30.4%) | <0.0001 |
| Septic shock-3 (n, %) | 630 (58.7%) | 429 (54.6%) | 201 (69.6%) | <0.0001 |
| ICU length of stay (days) (median, IQR) | 12 [6-23] | 13 [7-26] | 8 [4-15] | <0.0001 |
| Hospital length of stay (days) (median, IQR) | 28 [17-45] | 34 [22-51] | 14 [7-23] | <0.0001 |
| Pre-existing comorbidities | | | | |
| History of diabetes (n, %) | 280 (26.0%) | 188 (23.9%) | 92 (31.8%) | 0.0094 |
| Heart failure (n, %) | 230 (21.4%) | 150 (19.1%) | 80 (27.7%) | 0.0027 |
| Renal dysfunction (n, %) | 217 (20.2%) | 135 (17.2%) | 82 (28.4%) | <0.0001 |
| COPD (n, %) | 131 (12.2%) | 90 (11.4%) | 41 (14.2%) | 0.2277 |
| Liver cirrhosis (n, %) | 50 (4.7%) | 27 (3.4%) | 23 (8.0%) | 0.0030 |
| History of cancer (n, %) | 319 (29.7%) | 224 (28.5%) | 95 (32.9%) | 0.1630 |
| Immunosuppression (n, %) | 46 (4.3%) | 30 (3.8%) | 16 (5.5%) | 0.2271 |
| Microbiology | | | | |
| Gram positive (n, %) | 146 (13.6%) | 113 (14.4%) | 33 (11.4%) | 0.2050 |
| Gram negative (n, %) | 132 (12.3%) | 95 (12.1%) | 37 (12.8%) | 0.7467 |
| Fungal (n, %) | 51 (4.7%) | 37 (4.7%) | 14 (4.8%) | 0.9223 |
| Gram positive and negative (n, %) | 183 (17.0%) | 133 (16.9%) | 50 (17.3%) | 0.8767 |
| Gram positive and fungal (n, %) | 92 (8.6%) | 68 (8.6%) | 24 (8.3%) | 0.8610 |

TABLE 1-continued

| Patient characteristics at baseline for survival up to 28 days | | | | |
|---|---|---|---|---|
| | Total (N = 1076) | Survivors (N = 787) | Non-Survivors (N = 289) | P value |
| Gram negative and fungal (n, %) | 51 (4.7%) | 35 (4.5%) | 16 (5.5%) | 0.4631 |
| Gram positive and negative and fungal (n, %) | 115 (10.7%) | 81 (10.3%) | 34 (11.8%) | 0.4922 |
| Origin of infection | | | | |
| Pneumonia (n, %) | 453 (43.7%) | 327 (42.9%) | 126 (46.0%) | 0.3798 |
| Upper or lower respiratory (n, %) | 44 (4.3%) | 29 (3.8%) | 15 (5.5%) | 0.2523 |
| Thoracic (n, %) | 44 (4.3%) | 35 (4.6%) | 9 (3.3%) | 0.3444 |
| Bones/soft tissue (n, %) | 78 (7.5%) | 56 (7.4%) | 22 (8.0%) | 0.7161 |
| Gastrointestinal (n, %) | 80 (7.7%) | 68 (8.9%) | 12 (4.4%) | 0.0107 |
| Catheter associated (n, %) | 30 (2.9%) | 18 (2.4%) | 12 (4.4%) | 0.1015 |
| Surgical wound (n, %) | 41 (4.0%) | 31 (4.1%) | 10 (3.7%) | 0.7586 |
| Intraabdominal (n, %) | 375 (36.2%) | 276 (36.2%) | 99 (36.1%) | 0.9790 |
| Cardiovascular (n, %) | 6 (0.6%) | 4 (0.5%) | 2 (0.7%) | 0.7082 |
| Urogenital (n, %) | 99 (9.6%) | 70 (9.2%) | 29 (10.6%) | 0.5039 |
| Central nervous system (n, %) | 3 (0.3%) | 2 (0.3%) | 1 (0.4%) | 0.7916 |
| Bacteremia (n, %) | 31 (3.0%) | 20 (2.6%) | 11 (4.0%) | 0.2611 |
| Organ dysfunction | | | | |
| Neurological (n, %) | 348 (32.3%) | 240 (30.5%) | 108 (37.4%) | 0.0340 |
| Respiratory (n, %) | 486 (45.2%) | 350 (44.5%) | 136 (47.1%) | 0.4502 |
| Cardiovascular (n, %) | 829 (77.0%) | 584 (74.2%) | 245 (84.8%) | 0.0002 |
| Renal dysfunction (n, %) | 382 (35.5%) | 249 (31.6%) | 133 (46.0%) | <0.0001 |
| Haematological (n, %) | 156 (14.5%) | 89 (11.3%) | 67 (23.2%) | <0.0001 |
| Gastrointestinal (n, %) | 387 (36.0%) | 271 (34.4%) | 116 (40.1%) | 0.0855 |
| Metabolic dysfunction (n, %) | 718 (66.7%) | 504 (64.0%) | 214 (74.1%) | 0.0017 |
| Other organ dysfunction (n, %) | 499 (46.4%) | 380 (48.3%) | 119 (41.2%) | 0.0378 |
| Treatment upon ICU admission | | | | |
| Invasive mechanical ventilation (n, %) | 789 (73.3%) | 567 (72.1%) | 222 (76.8%) | 0.1133 |
| Non-invasive mechanical ventilation (n, %) | 64 (5.9%) | 46 (5.8%) | 18 (6.2%) | 0.8145 |
| Renal replacement therapy (n, %) | 326 (30.8%) | 158 (20.5%) | 168 (58.1%) | <0.0001 |
| Vasopressor use (n, %) | 980 (91.1%) | 712 (90.5%) | 268 (92.7%) | 0.2391 |
| Biomarker and severity scores | | | | |
| MR-proADM (nmol/L) (median, IQR) | 5.0 [2.6-8.8] | 4.0 [2.3-7.2] | 8.2 [5.2-12.6] | <0.0001 |
| PCT (ng/mL) (median, IQR) | 7.4 [1.6-26.9] | 6.6 [1.4-25.1] | 9.3 [2.6-31.8] | 0.0325 |
| Lactate (mmol/L) (median, IQR) | 2.7 [1.6-4.7] | 2.4 [1.5-4.0] | 3.7 [2.1-7.2] | <0.0001 |
| CRP (mg/L) (median, IQR) | 188 [120.9-282] | 189 [120.5-277.4] | 188 [122-287] | 0.7727 |
| SOFA (points) (mean, S.D.) | 10.02 (3.33) | 9.58 (3.18) | 11.22 (3.43) | <0.0001 |
| SAPS II (points) (mean, S.D.) | 63.27 (14.18) | 61.08 (13.71) | 69.24 (13.74) | <0.0001 |
| APACHE II (points) (mean, S.D.) | 24.24 (7.60) | 23.05 (7.37) | 27.49 (7.28) | <0.0001 |

ICU: Intensive Care Unit;

COPD: chronic obstructive pulmonary disease;

MR-proADM, mid-regional proadrenomedullin;

PCT: procalcitonin;

CRP: C-reactive protein;

SOFA: Sequential Organ Failure Assessment;

SAPS II: Simplified Acute Physiological score;

APACHE II: Acute Physiological and Chronic Health Evaluation.

Data are presented as absolute number and percentages in brackets, indicating the proportion of surviving and non-surviving patients at 28 days.

TABLE 2

Prediction of 28 day mortality following sepsis diagnosis

|  |  |  |  |  | Univariate | | | | Multivariate | | |
| --- | --- | --- | --- | --- | --- | --- | --- | --- | --- | --- | --- |
|  |  | N | Events | AUROC | LR X$^2$ | C-index | HR IQR [95%] | p | LR X$^2$ | C-index | HR IQR [95%] |
| All patients | MR-proADM | 1030 | 275 | 0.73 | 142.7 | 0.71 | 3.2 [2.6-3.9] | <0.0001 | 161.69 | 0.72 | 2.9 [2.4-3.6] |
|  | PCT | 1031 | 275 | 0.56 | 12.2 | 0.56 | 1.4 [1.2-1.7] | 0.0005 | 70.28 | 0.64 | 1.4 [1.1-1.7] |
|  | CRP | 936 | 251 | 0.49 | 0.12 | 0.51 | 1.0 [0.9-1.2] | 0.7304 | 50.54 | 0.62 | 1.1 [0.9-1.2] |
|  | Lactate | 1066 | 289 | 0.65 | 78.3 | 0.64 | 2.2 [1.8-2.5] | <0.0001 | 122.72 | 0.69 | 2.1 [1.7-2.5] |
|  | SOFA | 1051 | 282 | 0.64 | 47.3 | 0.62 | 1.6 [1.4-1.8] | <0.0001 | 96.05 | 0.67 | 1.6 [1.4-1.8] |
|  | SAPS II | 1076 | 289 | 0.67 | 70.5 | 0.65 | 1.8 [1.6-2.0] | <0.0001 | 100.3 | 0.67 | 1.6 [1.4-1.9] |
|  | APACHE II | 1076 | 289 | 0.67 | 69.9 | 0.65 | 1.9 [1.6-2.2] | <0.0001 | 99.21 | 0.67 | 1.7 [1.4-2.0] |
| Sepsis-3 | MR-proADM | 425 | 83 | 0.73 | 40.9 | 0.71 | 2.8 [2.0-3.8] | <0.0001 | 61.4 | 0.74 | 2.6 [1.8-3.7] |
|  | PCT | 425 | 83 | 0.56 | 4.6 | 0.56 | 1.4 [1.0-1.9] | 0.0312 | 40.6 | 0.70 | 1.5 [1.1-2.1] |
|  | CRP | 382 | 81 | 0.55 | 2.1 | 0.54 | 0.9 [0.7-1.1] | 0.1505 | 36.7 | 0.69 | 0.9 [0.7-1.1] |
|  | Lactate | 439 | 88 | 0.57 | 7.7 | 0.56 | 1.3 [1.1-1.6] | 0.0057 | 45.0 | 0.69 | 1.3 [1.1-1.7] |
|  | SOFA | 428 | 86 | 0.58 | 3.2 | 0.56 | 1.2 [1.0-1.5] | 0.0745 | 40.8 | 0.69 | 1.2 [1.0-1.5] |
|  | SAPS II | 439 | 88 | 0.62 | 14.5 | 0.61 | 1.7 [1.3-2.3] | 0.0001 | 45.0 | 0.69 | 1.5 [1.1-2.0] |
|  | APACHE II | 439 | 88 | 0.70 | 30.8 | 0.68 | 2.1 [1.6-2.6] | <0.0001 | 52.6 | 0.71 | 1.7 [1.3-2.3] |
| Septic shock-3 | MR-proADM | 597 | 192 | 0.72 | 77.4 | 0.69 | 2.4 [2.0-3.0] | <0.0001 | 93.5 | 0.71 | 2.3 [1.8-2.9] |
|  | PCT | 597 | 192 | 0.50 | 0.4 | 0.51 | 1.1 [0.9-1.3] | 0.5264 | 35.7 | 0.62 | 1.1 [0.9-1.4] |
|  | CRP | 545 | 170 | 0.53 | 2.1 | 0.53 | 1.1 [1.0-1.3] | 0.1498 | 31.7 | 0.63 | 1.1 [1.0-1.4] |
|  | Lactate | 627 | 201 | 0.64 | 52.2 | 0.64 | 2.0 [1.7-2.4] | <0.0001 | 79.4 | 0.68 | 2.0 [1.7-2.4] |
|  | SOFA | 616 | 196 | 0.65 | 31.1 | 0.62 | 1.6 [1.4-1.9] | <0.0001 | 56.5 | 0.66 | 1.6 [1.3-1.9] |
|  | SAPS II | 627 | 201 | 0.67 | 42.2 | 0.65 | 1.7 [1.4-1.9] | <0.0001 | 59.8 | 0.66 | 1.6 [1.3-1.8] |
|  | APACHE II | 627 | 201 | 0.63 | 28.3 | 0.61 | 1.6 [1.3-1.9] | <0.0001 | 50.7 | 0.65 | 1.5 [1.3-1.8] |

N: Number; AUROC: Area under the Receiver Operating Curve; LR X$^2$: HR: Hazard Ratio; IQR: Interquartile range. All multivariate analyses were associated by p <0.0001 to 28 day mortality.

TABLE 3

Survival analysis for 7 day, 90 day, ICU and hospital mortality

|  |  |  |  |  | Univariate | | | | Multivariate | | |
| --- | --- | --- | --- | --- | --- | --- | --- | --- | --- | --- | --- |
|  |  | Patients (N) | Mortality (N) | AUROC | LR X$^2$ | C-index | HR IQR [95% CI] | p-value | LR X$^2$ | C-index | HR IQR [95% CI] |
| 7 day | MR-proADM | 1037 | 131 | 0.72 | 71.6 | 0.71 | 3.3 [2.4-4.3] | <0.0001 | 82.1 | 0.73 | 3.4 [2.5-4.6] |
|  | PCT | 1038 | 131 | 0.58 | 9.7 | 0.58 | 1.5 [1.2-2.0] | 0.0019 | 28.4 | 0.64 | 1.6 [1.2-2.1] |
|  | CRP | 943 | 111 | 0.55 | 1.2 | 0.55 | 1.1 [0.9-1.4] | 0.2843 | 16.6 | 0.62 | 1.2 [0.9-1.4] |
|  | Lactate | 1074 | 135 | 0.72 | 86.0 | 0.71 | 3.1 [2.4-3.9] | <0.0001 | 99.1 | 0.73 | 3.1 [2.4-4.0] |
|  | SOFA | 1059 | 130 | 0.63 | 25.5 | 0.63 | 1.7 [1.4-2.0] | <0.0001 | 41.0 | 0.67 | 1.7 [1.4-2.1] |
|  | SAPS II | 1085 | 135 | 0.66 | 38.5 | 0.66 | 1.8 [1.5-2.2] | <0.0001 | 50.1 | 0.67 | 1.8 [1.5-2.2] |
|  | APACHE II | 1085 | 135 | 0.63 | 24.4 | 0.63 | 1.7 [1.4-2.1] | <0.0001 | 37.8 | 0.65 | 1.7 [1.4-2.1] |
| 90 day | MR-proADM | 1000 | 379 | 0.71 | 146.2 | 0.68 | 2.7 [2.3-3.2] | <0.0001 | 194.1 | 0.71 | 2.4 [2.0-2.8] |
|  | PCT | 1000 | 379 | 0.55 | 11.8 | 0.55 | 1.3 [1.1-1.5] | 0.0006 | 113.5 | 0.65 | 1.3 [1.1-1.5] |
|  | CRP | 909 | 348 | 0.51 | 0.2 | 0.51 | 1.0 [0.9-1.2] | 0.6641 | 92.3 | 0.64 | 1.1 [0.9-1.2] |
|  | Lactate | 1037 | 399 | 0.64 | 83.2 | 0.63 | 2.0 [1.7-2.3] | <0.0001 | 168.8 | 0.68 | 1.9 [1.6-2.2] |
|  | SOFA | 1021 | 388 | 0.62 | 48.1 | 0.61 | 1.5 [1.4-1.7] | <0.0001 | 143.7 | 0.67 | 1.5 [1.3-1.7] |
|  | SAPS II | 1045 | 399 | 0.66 | 81.1 | 0.64 | 1.7 [1.5-1.9] | <0.0001 | 144.4 | 0.67 | 1.5 [1.3-1.7] |
|  | APACHE II | 1045 | 399 | 0.67 | 86.4 | 0.64 | 1.8 [1.6-2.1] | <0.0001 | 146.8 | 0.67 | 1.6 [1.4-1.8] |
| ICU | MR-proADM | 1023 | 264 | 0.73 | 136.4 | 0.73 | 4.0 [3.1-5.2] | <0.0001 | 158.3 | 0.75 | 3.7 [2.8-4.9] |
|  | PCT | 1024 | 264 | 0.58 | 18.0 | 0.58 | 1.6 [1.3-2.0] | <0.0001 | 73.0 | 0.67 | 1.6 [1.3-2.1] |
|  | CRP | 928 | 237 | 0.54 | 2.5 | 0.54 | 1.1 [1.0-1.3] | 0.1108 | 51.4 | 0.65 | 1.2 [1.0-1.4] |
|  | Lactate | 1059 | 277 | 0.66 | 75.2 | 0.66 | 2.4 [2.0-3.0] | <0.0001 | 115.5 | 0.71 | 2.4 [1.9-2.9] |
|  | SOFA | 1044 | 270 | 0.64 | 48.6 | 0.64 | 1.8 [1.5-2.2] | <0.0001 | 95.2 | 0.69 | 1.8 [1.5-2.2] |
|  | SAPS II | 1070 | 277 | 0.65 | 58.7 | 0.65 | 1.9 [1.6-2.3] | <0.0001 | 91.2 | 0.68 | 1.8 [1.5-2.2] |
|  | APACHE II | 1070 | 277 | 0.66 | 62.5 | 0.66 | 2.1 [1.7-2.6] | <0.0001 | 91.6 | 0.69 | 1.9 [1.5-2.3] |
| Hospital | MR-proADM | 980 | 323 | 0.73 | 152.0 | 0.74 | 4.0 [3.1-5.2] | <0.0001 | 186.8 | 0.76 | 3.6 [2.7-4.6] |
|  | PCT | 981 | 323 | 0.57 | 15.0 | 0.57 | 1.5 [1.2-1.9] | 0.0001 | 96.2 | 0.68 | 1.5 [1.2-1.9] |
|  | CRP | 891 | 299 | 0.52 | 0.9 | 0.52 | 1.1 [0.9-1.3] | 0.3480 | 76.0 | 0.67 | 1.1 [1.0-1.3] |
|  | Lactate | 1016 | 342 | 0.66 | 77.8 | 0.66 | 2.4 [2.0-2.9] | <0.0001 | 146.2 | 0.72 | 2.3 [1.9-2.9] |
|  | SOFA | 1001 | 333 | 0.63 | 41.3 | 0.63 | 1.7 [1.4-2.0] | <0.0001 | 118.9 | 0.70 | 1.7 [1.4-2.0] |
|  | SAPS II | 1027 | 342 | 0.65 | 59.1 | 0.65 | 1.9 [1.6-2.2] | <0.0001 | 115.9 | 0.69 | 1.7 [1.4-2.0] |
|  | APACHE II | 1027 | 342 | 0.67 | 76.7 | 0.67 | 2.2 [1.9-2.7] | <0.0001 | 127.1 | 0.71 | 1.9 [1.6-2.4] |

All multivariate p values <0.0001 apart from PCT and CRP for 7 day mortality (0.0015 and 0.0843, respectively).

TABLE 4

Survival analysis for MR-proADM when added to individual biomarkers or clinical scores

|  |  | Patients (N) | Mortality (N) | Bivariate | | | Added value | | Multivariate | | | Added value | |
|---|---|---|---|---|---|---|---|---|---|---|---|---|---|
|  |  |  |  | LR X² | C-index | HR IQR [95% CI] | LR X² | p-value | LR X² | C-index | HR IQR [95% CI] | LR X² | p-value |
| 7 day | PCT | 1037 | 131 | 76.5 | 0.72 | 4.0 [2.9-5.6] | 66.8 | <0.0001 | 86.2 | 0.73 | 4.2 [2.9-6.1] | 57.8 | <0.0001 |
|  | CRP | 904 | 108 | 56.9 | 0.71 | 3.2 [2.3-4.3] | 55.0 | <0.0001 | 67.7 | 0.73 | 3.3 [2.3-4.7] | 49.4 | <0.0001 |
|  | Lactate | 1029 | 131 | 112.5 | 0.75 | 2.3 [1.7-3.1] | 28.1 | <0.0001 | 125.1 | 0.76 | 2.4 [1.7-3.3] | 26.4 | <0.0001 |
|  | SOFA | 1014 | 126 | 77.8 | 0.72 | 3.3 [2.3-4.6] | 53.5 | <0.0001 | 86.9 | 0.74 | 3.3 [2.3-4.7] | 46.6 | <0.0001 |
|  | SAPS II | 1037 | 131 | 83.1 | 0.73 | 2.8 [2.0-3.7] | 48.1 | <0.0001 | 93.5 | 0.74 | 2.9 [2.1-4.0] | 46.7 | <0.0001 |
|  | APACHE II | 1037 | 131 | 73.3 | 0.71 | 3.0 [2.2-4.1] | 50.9 | <0.0001 | 84.5 | 0.73 | 3.1 [2.2-4.2] | 48.6 | <0.0001 |
| 28 day | PCT | 1030 | 275 | 163.0 | 0.73 | 4.3 [3.4-5.5] | 150.7 | <0.0001 | 174.9 | 0.73 | 3.9 [3.0-5.1] | 105.0 | <0.0001 |
|  | CRP | 898 | 239 | 114.4 | 0.70 | 3.0 [2.5-3.8] | 114.2 | <0.0001 | 132.4 | 0.72 | 2.8 [2.2-3.6] | 80.5 | <0.0001 |
|  | Lactate | 1022 | 275 | 163.8 | 0.72 | 2.7 [2.2-3.3] | 85.9 | <0.0001 | 184.5 | 0.73 | 2.5 [2.0-3.1] | 61.4 | <0.0001 |
|  | SOFA | 1007 | 268 | 150.6 | 0.72 | 3.1 [2.5-3.9] | 104.1 | <0.0001 | 169.9 | 0.73 | 2.8 [2.2-3.6] | 74.4 | <0.0001 |
|  | SAPS II | 1030 | 275 | 163.4 | 0.72 | 2.7 [2.2-3.3] | 97.1 | <0.0001 | 176.5 | 0.73 | 2.6 [2.1-3.3] | 79.1 | <0.0001 |
|  | APACHE II | 1030 | 275 | 153.6 | 0.72 | 2.7 [2.2-3.4] | 88.8 | <0.0001 | 169.1 | 0.73 | 2.6 [2.1-3.3] | 74.1 | <0.0001 |
| 90 day | PCT | 1000 | 379 | 170.8 | 0.70 | 3.6 [3.0-4.4] | 159.0 | <0.0001 | 208.2 | 0.71 | 3.1 [2.5-3.9] | 94.8 | <0.0001 |
|  | CRP | 872 | 331 | 116.0 | 0.68 | 2.6 [2.2-3.1] | 116.0 | <0.0001 | 160.3 | 0.70 | 2.3 [1.9-2.8] | 68.8 | <0.0001 |
|  | Lactate | 993 | 379 | 169.4 | 0.69 | 2.3 [1.9-2.7] | 86.6 | <0.0001 | 217.5 | 0.71 | 2.0 [1.7-2.4] | 50.2 | <0.0001 |
|  | SOFA | 977 | 368 | 151.0 | 0.69 | 2.6 [2.1-3.1] | 103.1 | <0.0001 | 200.6 | 0.71 | 2.2 [1.8-2.7] | 59.9 | <0.0001 |
|  | SAPS II | 1000 | 379 | 173.7 | 0.70 | 2.3 [1.9-2.7] | 94.7 | <0.0001 | 208.4 | 0.71 | 2.2 [1.8-2.6] | 67.6 | <0.0001 |
|  | APACHE II | 1000 | 379 | 165.0 | 0.70 | 2.3 [1.9-2.7] | 83.3 | <0.0001 | 202.9 | 0.71 | 2.1 [1.8-2.6] | 62.5 | <0.0001 |
| ICU | PCT | 1023 | 264 | 149.5 | 0.75 | 5.7 [4.1-7.9] | 131.4 | <0.0001 | 165.3 | 0.76 | 4.9 [3.5-7.0] | 92.6 | <0.0001 |
|  | CRP | 889 | 226 | 104.6 | 0.72 | 3.7 [2.8-4.8] | 102.5 | <0.0001 | 127.4 | 0.74 | 3.4 [2.5-4.6] | 75.6 | <0.0001 |
|  | Lactate | 1015 | 264 | 153.5 | 0.74 | 3.2 [2.4-4.2] | 78.9 | <0.0001 | 175.6 | 0.76 | 2.9 [2.2-3.9] | 57.5 | <0.0001 |
|  | SOFA | 1000 | 257 | 140.7 | 0.74 | 3.6 [2.7-4.8] | 91.8 | <0.0001 | 163.8 | 0.76 | 3.2 [2.4-4.4] | 65.8 | <0.0001 |
|  | SAPS II | 1023 | 264 | 152.5 | 0.75 | 3.4 [2.6-4.4] | 94.4 | <0.0001 | 169.2 | 0.76 | 3.3 [2.5-4.3] | 77.7 | <0.0001 |
|  | APACHE II | 1023 | 264 | 148.2 | 0.74 | 3.3 [2.5-4.4] | 87.9 | <0.0001 | 165.7 | 0.76 | 3.3 [2.5-4.3] | 75.6 | <0.0001 |
| Hospital | PCT | 980 | 323 | 174.7 | 0.76 | 6.4 [4.6-8.8] | 159.5 | <0.0001 | 198.9 | 0.77 | 5.2 [3.6-7.3] | 103.2 | <0.0001 |
|  | CRP | 852 | 283 | 117.9 | 0.72 | 3.7 [2.9-4.8] | 117.3 | <0.0001 | 150.1 | 0.75 | 3.3 [2.5-4.3] | 77.7 | <0.0001 |
|  | Lactate | 972 | 323 | 167.4 | 0.75 | 3.3 [2.5-4.3] | 89.2 | <0.0001 | 202.5 | 0.76 | 2.8 [2.1-3.8] | 57.6 | <0.0001 |
|  | SOFA | 957 | 314 | 155.5 | 0.74 | 3.9 [3.0-5.2] | 113.7 | <0.0001 | 191.3 | 0.76 | 3.4 [2.5-4.5] | 74.6 | <0.0001 |
|  | SAPS II | 980 | 323 | 165.8 | 0.75 | 3.5 [2.7-4.5] | 107.7 | <0.0001 | 194.2 | 0.76 | 3.2 [2.4-4.2] | 81.3 | <0.0001 |
|  | APACHE II | 980 | 323 | 169.7 | 0.75 | 3.3 [2.6-4.3] | 95.4 | <0.0001 | 197.2 | 0.76 | 3.1 [2.4-4.1] | 75.1 | <0.0001 |

HR IQR [95% CI] indicates the hazard ratio for MR-proADM in each bivariate or multivariate model. 2 degrees of freedom in each bivariate model, compared to 11 in each multivariate model.

TABLE 5

AUROC analysis for 28 day mortality prediction based on SOFA severity levels

|  |  | N | Events | AUROC | Univariate | | | | Multivariate | | |
|---|---|---|---|---|---|---|---|---|---|---|---|
|  |  |  |  |  | LR X² | C-index [95%] | HR IQR [95%] | p | LR X² | C-index [95%] | HR IQR [95%] | p |
| SOFA ≤7 | MR-proADM | 232 | 32 | 0.74 | 25.1 | 0.72 | 3.6 [2.2-6.0] | <0.0001 | 37.6 | 0.77 | 3.1 [1.7-5.6] | <0.0001 |
|  | PCT | 232 | 32 | 0.55 | 0.9 | 0.55 | 1.3 [0.8-2.2] | 0.3519 | 22.4 | 0.72 | 1.2 [0.7-2.1] | 0.0134 |
|  | CRP | 210 | 32 | 0.45 | 1.1 | 0.55 | 1.3 [0.8-2.0] | 0.2881 | 17.5 | 0.69 | 1.3 [0.8-2.1] | 0.0647 |
|  | Lactate | 236 | 35 | 0.62 | 5.5 | 0.61 | 1.8 [1.1-3.0] | 0.0186 | 24.3 | 0.71 | 1.7 [1.0-2.8] | 0.0069 |
|  | SAPS II | 240 | 35 | 0.65 | 9.3 | 0.50 | 2.0 [1.3-3.0] | 0.0023 | 22.5 | 0.71 | 1.4 [0.8-2.5] | 0.013 |
|  | APACHE II | 240 | 35 | 0.69 | 14.3 | 0.64 | 2.4 [1.5-3.9] | 0.0002 | 24.6 | 0.71 | 1.7 [1.0-3.0] | 0.0061 |
| SOFA 8-13 | MR-proADM | 620 | 172 | 0.72 | 74.3 | 0.70 | 2.7 [2.1-3.3] | <0.0001 | 89.3 | 0.72 | 2.3 [1.8-3.0] | <0.0001 |
|  | PCT | 620 | 172 | 0.54 | 3.9 | 0.54 | 1.3 [1.0-1.6] | 0.0482 | 46.3 | 0.65 | 1.3 [1.0-1.6] | <0.0001 |
|  | CRP | 572 | 161 | 0.51 | 0.1 | 0.52 | 1.0 [0.9-1.2] | 0.7932 | 39.3 | 0.64 | 1.0 [0.9-1.2] | <0.0001 |
|  | Lactate | 650 | 181 | 0.61 | 26.9 | 0.61 | 1.7 [1.4-2.0] | <0.0001 | 61.6 | 0.67 | 1.6 [1.3-2.0] | <0.0001 |
|  | SAPS II | 653 | 181 | 0.64 | 27.7 | 0.57 | 1.6 [1.3-1.9] | 0.0014 | 53.9 | 0.64 | 1.4 [1.2-1.7] | <0.0001 |
|  | APACHE II | 653 | 181 | 0.63 | 22.1 | 0.62 | 1.5 [1.3-1.8] | <0.0001 | 49.3 | 0.65 | 1.3 [1.1-1.6] | <0.0001 |
| SOFA ≥14 | MR-proADM | 155 | 64 | 0.67 | 14.9 | 0.65 | 2.0 [1.4-3.0] | 0.0001 | 25.6 | 0.69 | 2.2 [1.4-3.3] | 0.0043 |
|  | PCT | 155 | 64 | 0.49 | 0.2 | 0.52 | 1.1 [0.8-1.5] | 0.6944 | 11.5 | 0.62 | 1.2 [0.8-1.7] | 0.3169 |
|  | CRP | 136 | 53 | 0.57 | 2.0 | 0.55 | 0.9 [0.7-1.1] | 0.1569 | 14.9 | 0.64 | 2.6 [1.7-3.8] | 0.0004 |
|  | Lactate | 158 | 66 | 0.69 | 22.6 | 0.68 | 2.5 [1.7-3.6] | <0.0001 | 32.3 | 0.71 | 0.9 [0.7-1.1] | 0.1370 |
|  | SAPS II | 158 | 66 | 0.54 | 2.8 | 0.56 | 1.3 [0.9-1.8] | 0.0930 | 15.3 | 0.63 | 1.2 [0.8-1.7] | 0.2958 |
|  | APACHE II | 158 | 66 | 0.54 | 1.8 | 0.54 | 1.3 [0.9-1.7] | 0.1754 | 11.8 | 0.62 | 1.2 [0.9-1.7] | 0.2487 |

N: Number; AUROC: Area under the Receiver Operating Curve; LR X²: HR: Hazard Ratio; IQR: Interquartile range.

TABLE 6

Survival analysis for MR-proADM within different organ dysfunction severity groups when combined with individual biomarkers or clinical scores

|  |  | Patients (N) | Mortality (N) | Univariate | | | | Multivariate | | | |
|---|---|---|---|---|---|---|---|---|---|---|---|
|  |  |  |  | LR $X^2$ | C-index | HR IQR [95% CI] | p-value | LR $X^2$ | C-index | HR IQR [95% CI] | p-value |
| SOFA ≤7 | PCT | 232 | 32 | 30.0 | 0.75 | 5.3 [2.8-10.1] | <0.0001 | 41.8 | 0.78 | 5.0 [2.3-10.8] | <0.0001 |
|  | CRP | 204 | 29 | 20.1 | 0.71 | 3.1 [1.8-5.3] | <0.0001 | 30.5 | 0.75 | 2.7 [1.4-5.0] | 0.0013 |
|  | Lactate | 229 | 32 | 25.1 | 0.72 | 3.5 [2.0-5.9] | <0.0001 | 37.2 | 0.77 | 3.1 [1.7-5.7] | 0.0001 |
|  | SOFA | 232 | 32 | 27.3 | 0.73 | 3.9 [2.3-6.7] | <0.0001 | 40.4 | 0.78 | 3.5 [1.9-6.5] | <0.0001 |
|  | SAPS II | 232 | 32 | 28.9 | 0.74 | 3.2 [1.9-5.4] | <0.0001 | 38.4 | 0.78 | 3.1 [1.7-5.5] | 0.0001 |
|  | APACHE II | 232 | 32 | 34.2 | 0.77 | 2.9 [1.7-4.9] | <0.0001 | 41.4 | 0.79 | 3.0 [1.7-5.5] | <0.0001 |
| SOFA 8-13 | PCT | 620 | 172 | 90.4 | 0.72 | 3.8 [2.8-5.0] | <0.0001 | 98.0 | 0.72 | 3.2 [2.3-4.4] | <0.0001 |
|  | CRP | 544 | 153 | 63.1 | 0.69 | 2.6 [2.0-3.3] | <0.0001 | 78.6 | 0.71 | 2.4 [1.7-2.9] | <0.0001 |
|  | Lactate | 617 | 172 | 81.4 | 0.70 | 2.4 [1.9-3.1] | <0.0001 | 97.0 | 0.72 | 2.1 [1.6-2.7] | <0.0001 |
|  | SOFA | 620 | 172 | 76.2 | 0.70 | 2.6 [2.0-3.2] | <0.0001 | 90.7 | 0.72 | 2.3 [1.8-2.9] | <0.0001 |
|  | SAPS II | 620 | 172 | 87.2 | 0.71 | 2.4 [1.9-3.1] | <0.0001 | 97.2 | 0.72 | 2.3 [1.8-2.9] | <0.0001 |
|  | APACHE II | 620 | 172 | 79.0 | 0.70 | 2.5 [1.9-3.1] | <0.0001 | 90.9 | 0.72 | 2.3 [1.8-2.9] | <0.0001 |
| SOFA ≥14 | PCT | 155 | 64 | 16.3 | 0.66 | 2.2 [1.5-3.2] | 0.0001 | 27.1 | 0.69 | 2.4 [1.5-3.9] | 0.0001 |
|  | CRP | 134 | 52 | 13.4 | 0.65 | 1.9 [1.3-2.9] | 0.0007 | 26.9 | 0.70 | 2.1 [1.3-3.3] | 0.0007 |
|  | Lactate | 155 | 64 | 28.9 | 0.69 | 1.7 [1.1-2.5] | 0.0063 | 38.1 | 0.71 | 1.8 [1.1-2.8] | 0.0068 |
|  | SOFA | 155 | 64 | 15.3 | 0.65 | 2.0 [1.3-2.9] | 0.0004 | 26.7 | 0.69 | 2.1 [1.3-3.2] | 0.0004 |
|  | SAPS II | 155 | 64 | 17.0 | 0.65 | 2.1 [1.4-3.1] | 0.0001 | 26.2 | 0.69 | 2.2 [1.4-3.3] | 0.0001 |
|  | APACHE II | 155 | 64 | 15.1 | 0.64 | 2.0 [1.3-2.9] | 0.0002 | 25.7 | 0.69 | 2.1 [1.4-3.3] | 0.0002 |

TABLE 7

Corresponding 28 day SOFA and MR-proADM disease severity groups

| | | SOFA severity groups | | |
|---|---|---|---|---|
| | | Low severity (≤7 points) N = 232, 13.8% mortality | Intermediate severity (≤8 points ≤13) N = 620, 27.7% mortality | High severity (≥14 points) N = 155, 41.3% mortality |
| MR-proADM severity groups | Low severity (≤2.7 nmol/L) N = 265, 9.8% mortality | N = 111 (41.9%) 7.2% mortality | N = 139 (52.8%) 10.8% mortality | N = 15 (5.7%) 20.0% mortality |
| | Intermediate severity (<2.7 nmol/L ≤10.9) N = 581, 26.2% mortality | N = 114 (19.6%) 15.8% mortality | N = 394 (68.0%) 27.7% mortality | N = 73 (12.6%) 34.2% mortality |
| | High severity (>10.9 nmol/L) N = 161 55.9% mortality | N = 7 (4.3%) 85.7% mortality | N = 87 (53.4%) 55.2% mortality | N = 67 (41.6%) 53.7% mortality |

MR-proADM: mid-regional proadrenomedullin;
SOFA: Sequential Organ Failure Assessment

TABLE 8

Corresponding 28 day SAPS II and MR-proADM disease severity groups

| | | SAPS II severity groups | | |
|---|---|---|---|---|
| | | Low severity (≤53 points) N = 235, 11.5% mortality | Intermediate severity (≤54 points ≤79) N = 656, 29.3% mortality | High severity (≥80 points) N = 139, 40.3% mortality |
| MR-proADM severity groups | Low severity (≤2.7 nmol/L) N = 271, 10.3% mortality | N = 108 (39.9%) 7.4% mortality | N = 143 (52.8%) 11.2% mortality | N = 20 (7.4%) 20.0% mortality |
| | Intermediate severity (<2.7 nmol/L ≤10.9) N = 594, 26.4% mortality | N = 118 (19.9%) 13.6% morality | N = 398 (67.0%) 27.9% mortality | N = 78 (13.1%) 38.5% mortality |
| | High severity (>10.9 nmol/L) N = 165, 54.5% mortality | N = 9 (5.5%) 33.3% mortality | N = 115 (69.7%) 56.5% mortality | N = 41 (24.8%) 53.7% mortality |

MR-proADM: mid-regional proadrenomedullin;
SAPS II: Simplified Acute Physiological II

TABLE 9

Corresponding 28 day APACHE II and MR-proADM disease severity groups
APACHE II severity groups

|  |  | Low severity (≤19 points) N = 287, 11.5% mortality | Intermediate severity (≤20 points ≤32) N = 591, 30.3% mortality | High severity (≥33 points) N = 152, 41.4% mortality |
|---|---|---|---|---|
| MR-proADM severity groups | Low severity (≤2.7 nmol/L) N = 271, 10.3% mortality | N = 122 (45.0%) 7.4% mortality | N = 137 (50.6%) 10.9% mortality | N = 12 (4.4%) 33.3% mortality |
|  | Intermediate severity (<2.7 nmol/L ≤10.9) N = 594, 26.4% mortality | N = 154 (25.9%) 12.3% mortality | N = 356 (59.9%) 30.1% mortality | N = 84 (14.1%) 36.9% mortality |
|  | High severity (>10.9 nmol/L) N = 165, 54.5% mortality | N = 11 (6.7%) 45.5% mortality | N = 98 (59.4%) 58.2% mortality | N = 56 (33.9%) 50.0% mortality |

MR-proADM: mid-regional proadrenomedullin;
APACHE II: Acute Physiological and Chronic Health Evaluation II

TABLE 10

Corresponding 28 day lactate and MR-proADM disease severity groups
Lactate severity groups

|  |  | Low severity (≤1.4 mmol/L) N = 196, 15.8% mortality | Intermediate severity (<1.4 mmol/L ≤6.4) N = 668, 24.1% mortality | High severity (>6.4 mmol/L) N = 158, 52.5% mortality |
|---|---|---|---|---|
| MR-proADM severity groups | Low severity (≤2.7 nmol/L) N = 267, 10.5% mortality | N = 99 (37.1%) 8.1% mortality | N = 154 (57.7%) 9.1% mortality | N = 14 (5.2%) 42.9% mortality |
|  | Intermediate severity (<2.7 nmol/L ≤10.9) N = 591, 26.6% mortality | N = 90 (15.2%) 21.1% mortality | N = 421 (71.2%) 25.2% mortality | N = 80 (13.5%) 40.0% mortality |
|  | High severity (>10.9 nmol/L) N = 164, 54.9% mortality | N = 7 (4.3%) 57.1% mortality | N = 93 (56.7%) 44.1% mortality | N = 64 (39.0%) 70.3% mortality |

MR-proADM: mid-regional proadrenomedullin

TABLE 11

Biomarker and SOFA association with 28 day mortality at days 1, 4, 7 and 10

|  |  | Patients (N) | Mortality (N) | AUROC | LR $X^2$ | C-index | HR IQR [95% CI] | p-value | LR $X^2$ | C-index | HR IQR [95% CI] | p-value |
|---|---|---|---|---|---|---|---|---|---|---|---|---|
| Day 1 | MR-proADM | 993 | 242 | 0.76 | 152.5 | 0.73 | 3.3 [2.8-4.0] | <0.0001 | 173.2 | 0.74 | 3.2 [2.6-4.0] | <0.0001 |
|  | PCT | 993 | 242 | 0.59 | 23.1 | 0.59 | 1.6 [1.3-2.0] | <0.0001 | 74.6 | 0.65 | 1.6 [1.3-2.0] | <0.0001 |
|  | CRP | 919 | 226 | 0.54 | 6.2 | 0.54 | 0.9 [0.8-1.0] | 0.0128 | 61.2 | 0.65 | 0.9 [0.8-1.0] | <0.0001 |
|  | Lactate | 1041 | 265 | 0.73 | 206.4 | 0.72 | 2.4 [2.2-2.7] | <0.0001 | 253.9 | 0.75 | 2.5 [2.2-2.8] | <0.0001 |
|  | SOFA | 1011 | 260 | 0.74 | 143.8 | 0.72 | 2.5 [2.2-2.9] | <0.0001 | 192.8 | 0.75 | 2.6 [2.2-3.0] | <0.0001 |
| Day 4 | MR-proADM | 777 | 158 | 0.76 | 100.5 | 0.73 | 3.2 [2.5-4.0] | <0.0001 | 123.7 | 0.75 | 3.0 [2.3-3.8] | <0.0001 |
|  | PCT | 777 | 158 | 0.62 | 22.6 | 0.61 | 1.7 [1.4-2.1] | <0.0001 | 69.3 | 0.68 | 1.8 [1.4-2.2] | <0.0001 |
|  | CRP | 708 | 146 | 0.48 | 0.7 | 0.52 | 1.1 [0.9-1.3] | 0.3925 | 45.8 | 0.65 | 1.1 [0.9-1.4] | <0.0001 |
|  | Lactate | 803 | 166 | 0.69 | 60.6 | 0.68 | 1.8 [1.6-2.0] | <0.0001 | 100.9 | 0.71 | 1.7 [1.5-2.0] | <0.0001 |
|  | SOFA | 767 | 162 | 0.75 | 111.5 | 0.72 | 3.0 [2.4-3.6] | <0.0001 | 155.9 | 0.76 | 3.1 [2.5-3.8] | <0.0001 |
| Day 7 | MR-proADM | 630 | 127 | 0.78 | 93.7 | 0.76 | 3.4 [2.6-4.3] | <0.0001 | 117.8 | 0.76 | 3.3 [2.5-4.3] | <0.0001 |
|  | PCT | 631 | 128 | 0.72 | 62.3 | 0.70 | 2.6 [2.1-3.3] | <0.0001 | 101.6 | 0.74 | 2.7 [2.1-3.4] | <0.0001 |
|  | CRP | 583 | 121 | 0.56 | 3.5 | 0.55 | 1.3 [1.0-1.6] | 0.0606 | 47.1 | 0.67 | 1.3 [1.0-1.7] | <0.0001 |
|  | Lactate | 658 | 138 | 0.68 | 69.4 | 0.68 | 2.0 [1.7-2.3] | <0.0001 | 112.2 | 0.73 | 2.0 [1.7-2.4] | <0.0001 |
|  | SOFA | 617 | 128 | 0.75 | 107.7 | 0.73 | 2.7 [2.3-3.3] | <0.0001 | 140.2 | 0.77 | 2.8 [2.3-3.4] | <0.0001 |
| Day 10 | MR-proADM | 503 | 82 | 0.78 | 72.6 | 0.76 | 4.3 [3.0-6.1] | <0.0001 | 90.9 | 0.78 | 3.8 [2.6-5.5] | <0.0001 |
|  | PCT | 503 | 82 | 0.75 | 52.0 | 0.74 | 2.8 [2.2-3.7] | <0.0001 | 90.4 | 0.78 | 3.1 [2.3-4.2] | <0.0001 |
|  | CRP | 457 | 80 | 0.61 | 10.0 | 0.60 | 1.6 [1.2-2.2] | <0.0001 | 51.2 | 0.71 | 1.8 [1.3-2.6] | <0.0001 |
|  | Lactate | 516 | 88 | 0.61 | 19.8 | 0.61 | 1.6 [1.3-2.0] | <0.0001 | 547.7 | 0.70 | 1.6 [1.3-2.0] | <0.0001 |
|  | SOFA | 490 | 84 | 0.76 | 85.8 | 0.75 | 3.3 [2.6-4.3] | <0.0001 | 107.8 | 0.78 | 3.1 [2.4-4.1] | <0.0001 |

TABLE 12

Low and high risk severity groups and corresponding mortality rates throughout ICU treatment

| | | Low severity patient population | | | | | High severity patient population | | | | |
|---|---|---|---|---|---|---|---|---|---|---|---|
| | | Patients (N) | Mortality (N, %) | Optimal cutoff | Sensitivity | Specificity | Patients (N) | Mortality (N, %) | Optimal cutoff | Sensitivity | Specificity |
| Day 1 | MR-proADM | 304 | 24 (7.9%) | 2.80 | 0.90 | 0.37 | 162 | 87 (53.7%) | 9.5 | 0.36 | 0.90 |
| | PCT | 203 | 25 (12.3%) | 1.02 | 0.90 | 0.24 | 115 | 40 (34.8%) | 47.6 | 0.17 | 0.90 |
| | CRP | 101 | 32 (31.7%) | 99 | 0.90 | 0.14 | 88 | 18 (4.8%) | 373 | 0.08 | 0.90 |
| | Lactate | 310 | 33 (10.6%) | 1.22 | 0.88 | 0.36 | 185 | 109 (58.9%) | 3.5 | 0.43 | 0.89 |
| | SOFA | 435 | 49 (11.3%) | 8.0 | 0.88 | 0.40 | 165 | 87 (52.7%) | 14 | 0.33 | 0.90 |
| Day 4 | MR-proADM | 290 | 16 (5.5%) | 2.25 | 0.90 | 0.44 | 120 | 58 (48.3%) | 7.7 | 0.37 | 0.90 |
| | PCT | 147 | 16 (10.9%) | 0.33 | 0.90 | 0.21 | 87 | 25 (28.7%) | 14.08 | 0.16 | 0.90 |
| | CRP | 65 | 9 (13.8%) | 32.7 | 0.90 | 0.06 | 51 | 15 (29.4%) | 276.5 | 0.06 | 0.90 |
| | Lactate | 124 | 15 (12.1%) | 0.89 | 0.91 | 0.17 | 136 | 65 (47.8%) | 2.15 | 0.39 | 0.89 |
| | SOFA | 213 | 15 (7.0%) | 5.5 | 0.91 | 0.33 | 137 | 67 (48.9%) | 12.75 | 0.41 | 0.88 |
| Day 7 | MR-proADM | 252 | 14 (5.6%) | 2.25 | 0.89 | 0.47 | 104 | 54 (51.9%) | 6.95 | 0.43 | 0.90 |
| | PCT | 184 | 14 (7.6%) | 0.31 | 0.89 | 0.34 | 85 | 35 (41.2%) | 4.67 | 0.27 | 0.90 |
| | CRP | 62 | 12 (19.4%) | 27.4 | 0.90 | 0.11 | 69 | 23 (37.7%) | 207 | 0.19 | 0.90 |
| | Lactate | 104 | 15 (14.4%) | 0.84 | 0.89 | 0.17 | 102 | 51 (50.0%) | 2.10 | 0.37 | 0.90 |
| | SOFA | 207 | 16 (7.7%) | 5.5 | 0.88 | 0.39 | 91 | 48 (52.7%) | 12.5 | 0.38 | 0.91 |
| Day 10 | MR-proADM | 213 | 8 (3.8%) | 2.25 | 0.90 | 0.49 | 78 | 35 (44.9%) | 7.45 | 0.43 | 0.90 |
| | PCT | 177 | 9 (5.1%) | 0.30 | 0.89 | 0.40 | 74 | 32 (43.2%) | 2.845 | 0.39 | 0.90 |
| | CRP | 69 | 8 (11.6%) | 32.1 | 0.90 | 0.16 | 52 | 14 (26.9%) | 204 | 0.18 | 0.90 |
| | Lactate | 47 | 7 (14.9%) | 0.68 | 0.92 | 0.09 | 65 | 24 (36.9%) | 2.15 | 0.27 | 0.90 |
| | SOFA | 116 | 9 (7.8%) | 4.5 | 0.89 | 0.26 | 85 | 42 (49.4%) | 11.5 | 0.50 | 0.89 |

TABLE 13

Mortality and duration of ICU therapy based on MR-proADM concentrations and ICU specific therapies

| | Patient severity group | N | SOFA | Length of stay (days) | 28 day mortality (N, %) | 90 day mortality (N, %) |
|---|---|---|---|---|---|---|
| Day 4 | Total patient population | 777 | 8.4 (4.3) | 16 [10-27] | 158 (20.3%) | 256 (33.9%) |
| | Clinically stable | 145 | 4.5 (2.4) | 8 [6-11] | 10 (6.9%) | 22 (15.8%) |
| | Clinically stable and low MR-proADM | 79 | 3.6 (1.5) | 8 [7-10] | 0 (0.0%) | 1 (1.4%) |
| | Actual day 4 discharges* | 43 | 3.6 (2.1) | — | 1 (2.3%) | 4 (10.0%) |
| Day 7 | Total patient population | 630 | 8.0 (4.2) | 19 [13-31] | 127 (20.2%) | 214 (34.9%) |
| | Clinically stable | 124 | 3.9 (1.7) | 11.5 [9-16] | 9 (7.3%) | 17 (13.9%) |
| | Clinically stable and low MR-proADM | 78 | 3.4 (1.6) | 11 [9-14] | 1 (1.3%) | 4 (5.3%) |
| | Actual day 7 discharges* | 36 | 3.6 (2.6) | — | 2 (5.6%) | 5 (13.9%) |
| Day 10 | Total patient population | 503 | 7.6 (4.0) | 23.5 [17-34.25] | 82 (16.3%) | 159 (32.6%) |
| | Clinically stable | 85 | 3.5 (1.8) | 15 [13-22] | 9 (10.6%) | 14 (17.3%) |
| | Clinically stable and low MR-proADM | 57 | 3.2 (1.3) | 14 [12.25-19] | 1 (1.8%) | 2 (3.8%) |
| | Actual day 10 discharges* | 29 | 4.0 (2.6) | — | 5 (17.2%) | 7 (24.1%) |

*excludes same or next day mortalities

TABLE 14

Time dependent Cox regressions for single and cumulative additions of MR-proADM

| | Univariate model | | | | | Multivariate model | | | | |
|---|---|---|---|---|---|---|---|---|---|---|
| | LR $X^2$ | DF | Added LR $X^2$ | Added DF | p-value | LR $X^2$ | DF | Added LR $X^2$ | Added DF | p-value |
| Addition of single days to baseline values | | | | | | | | | | |
| MR-proADM baseline | 144.2 | 1 | Reference | | | 163.0 | 10 | Reference | | |
| +Day 1 | 169.8 | 2 | 25.6 | 1 | <0.001 | 190.6 | 11 | 27.6 | 1 | <0.001 |
| +Day 4 | 161.9 | 2 | 17.7 | 1 | <0.001 | 180.4 | 11 | 17.4 | 1 | <0.001 |

TABLE 14-continued

Time dependent Cox regressions for single and cumulative additions of MR-proADM

|  | Univariate model | | | | | Multivariate model | | | | |
| --- | --- | --- | --- | --- | --- | --- | --- | --- | --- | --- |
|  | LR $X^2$ | DF | Added LR $X^2$ | Added DF | p-value | LR $X^2$ | DF | Added LR $X^2$ | Added DF | p-value |
| +Day 7 | 175.7 | 2 | 31.5 | 1 | <0.001 | 195.1 | 11 | 32.1 | 1 | <0.001 |
| +Day 10 | 179.8 | 2 | 35.6 | 1 | <0.001 | 197.9 | 11 | 34.9 | 1 | <0.001 |
| Addition of consecutive days to baseline values | | | | | | | | | | |
| MR-proADM baseline | 144.2 | 1 | Reference | | | 163.0 | 10 | Reference | | |
| +Day 1 | 169.8 | 2 | 25.6 | 1 | <0.001 | 190.6 | 11 | 27.6 | 1 | <0.001 |
| +Day 1 + Day 4 | 174.9 | 3 | 5.1 | 1 | 0.0243 | 195.4 | 12 | 4.8 | 1 | 0.0280 |
| +Day 1 + Day 4 + Day 7 | 188.7 | 4 | 13.9 | 1 | <0.001 | 210.4 | 13 | 15.0 | 1 | <0.001 |
| +Day 1 + Day 4 + Day 7 + Day 10 | 195.2 | 5 | 6.5 | 1 | 0.0111 | 216.6 | 14 | 6.2 | 1 | 0.0134 |

MR-proADM: mid-regional proadrenomedullin;
DF: Degrees of Freedom

TABLE 15

28 and 90 day mortality rates following PCT and MR-proADM kinetics

| Biomarker Kinetics | | 28 day mortality | | | 90 day mortality | | |
| --- | --- | --- | --- | --- | --- | --- | --- |
| Baseline | Day 1 | N | % | HR IQR [95% CI] | N | % | HR IQR [95% CI] |
| PCT decrease ≥20% | | 458 | 18.3% | | 447 | 28.2% | |
| MR-proADM   Low | Low | 125 | 5.6% | 3.6 [1.6-8.1]* | 121 | 13.2% | 2.7 [1.6-4.8]* |
| severity level  Intermediate | Intermediate | 204 | 19.1% | 5.3 [3.0-9.3]** | 201 | 32.3% | 3.8 [2.3-6.3]** |
| High | High | 27 | 66.7% | 19.1 [8.0-45.9]*** | 27 | 70.4% | 10.4 [5.3-20.2]*** |
| Increasing | | | | | | | |
| Low | Intermediate | 2 | 50.0% | — | 2 | 50.0% | — |
| Intermediate | High | 10 | 40.0% | 2.5 [0.9-7.0]†† | 10 | 50.0% | 1.9 [0.8-4.8]†† |
| Decreasing | | | | | | | |
| High | Intermediate | 30 | 36.7% | 0.4 [0.2-0.9]‡ | 29 | 44.8% | 0.5 [0.2-0.9]‡ |
| High | Low | — | — | — | — | — | — |
| Intermediate | Low | 60 | 8.3% | 0.4 [0.2-1.0]‡‡ | 57 | 12.3% | 0.3 [0.2-0.7]‡‡ |
| PCT decrease <20% | | 522 | 29.7% | | 508 | 42.5% | |
| MR-proADM   Low | Low | 106 | 10.4% | 3.1 [1.7-5.9]* | 105 | 16.2% | 3.2 [1.9-5.3]* |
| severity level  Intermediate | Intermediate | 229 | 29.7% | 2.0 [1.3-2.9]** | 221 | 43.4% | 1.9 [1.3-2.6]** |
| High | High | 77 | 49.4% | 6.2 [3.2-12.2]*** | 75 | 64.0% | 5.9 [3.4-10.3]*** |
| Increasing | | | | | | | |
| Low | Intermediate | 29 | 17.2% | 1.8 [0.6-5.2]† | 27 | 44.4% | 3.2 [1.5-6.7]† |
| Intermediate | High | 45 | 53.3% | 2.3 [1.4-3.6]†† | 45 | 68.9% | 2.1 [1.4-3.2]†† |
| Decreasing | | | | | | | |
| High | Intermediate | 11 | 54.5% | — | 11 | 72.7% | — |
| High | Low | 1 | 0.0% | — | 1 | 100.0% | — |
| Intermediate | Low | 24 | 12.5% | 0.4 [0.1-1.2]‡‡ | 23 | 13.0% | 0.2 [0.1-0.8]‡‡ |

Hazard ratios for patients with: *continuously intermediate vs. low values;

**continuously high vs. intermediate values

***continuously high vs. low values;

†Increasing low to intermediate vs. continuously low values;

††Increasing intermediate to high vs. continuously intermediate values;

‡decreasing high to intermediate vs. continuously high values;

‡‡Decreasing intermediate to low vs. increasing intermediate to high values. Kaplan Meier plots illustrate either individual patient subgroups, or grouped increasing or decreasing subgroups.

TABLE 16

Mortality rates following changes in PCT concentrations and MR-proADM severity levels

| | | | 7 day mortality | | | ICU mortality | | | Hospital mortality | | |
|---|---|---|---|---|---|---|---|---|---|---|---|
| | Baseline | Day 1 | N | % | HR IQR [95% CI] | N | % | HR IQR [95% CI] | N | % | HR IQR [95% CI] |
| PCT decrease ≥20% | | | 461 | 6.1% | | 456 | 16.7% | | 439 | 24.1% | |
| MR-proADM severity level | Low | Low | 126 | 2.4% | 1.9 [0.5-6.9]* | 126 | 4.8% | 3.9 [1.6-9.6]* | 123 | 7.3% | 4.9 [2.3-10.3]* |
| | Intermediate | Intermediate | 205 | 4.4% | 8.2 [3.4-21.2]** | 202 | 16.3% | 8.7 [3.7-20.7]** | 194 | 27.8% | 6.2 [2.5-14.9]** |
| | High | High | 27 | 29.6% | 15.2 [4.0-57.3]*** | 27 | 63.0% | 34.0 [11.0-105.5]*** | 27 | 70.4% | 30.1 [10.3-87.6]*** |
| Increasing | | | | | | | | | | | |
| | Low | Intermediate | 3 | 0.0% | — | 2 | 0.0% | — | 2 | 0.0% | — |
| | Intermediate | High | 10 | 20.0% | 4.7 [1.0-21.6]†† | 10 | 30.0% | 2.2 [0.5-8.9]†† | 10 | 50.0% | 2.6 [0.7-9.3]†† |
| Decreasing | | | | | | | | | | | |
| | High | Intermediate | 30 | 16.7% | 0.5 [0.2-1.6]‡ | 29 | 37.9% | 0.4 [0.1-1.1]‡ | 28 | 46.4% | 0.4 [0.1-1.1]‡ |
| | Intermediate | Low | 60 | 1.7% | 0.4 [0.0-3.0]‡‡ | 59 | 10.2% | 0.6 [0.1-1.5]‡‡ | 55 | 10.9% | 0.3 [0.1-0.8]‡‡ |
| PCT decrease <20% | | | 526 | 13.7% | | 517 | 30.2% | | 493 | 36.9% | |
| MR-proADM severity level | Low | Low | 107 | 5.6% | 2.0 [0.8-4.9]* | 107 | 10.3% | 3.4 [1.7-6.8]* | 102 | 13.7% | 3.6 [1.9-6.8]* |
| | Intermediate | Intermediate | 230 | 10.9% | 2.6 [1.5-4.7]** | 225 | 28.0% | 3.0 [1.8-5.2]** | 216 | 36.6% | 2.4 [1.4-4.2]** |
| | High | High | 77 | 26.0% | 5.3 [2.1-13.2]*** | 74 | 54.1% | 10.3 [4.7-22.3]*** | 72 | 58.3% | 8.8 [4.2-18.3]*** |
| Increasing | | | | | | | | | | | |
| | Low | Intermediate | 30 | 13.3% | 2.5 [0.7-8.9]† | 29 | 31.0% | 3.9 [1.4-10.7]† | 27 | 37.0% | 3.7 [1.4-9.7]† |
| | Intermediate | High | 46 | 28.3% | 3.0 [1.5-5.8]†† | 45 | 57.8% | 3.3 [1.7-6.4]†† | 43 | 65.1% | 3.2 [1.6-6.4]†† |
| Decreasing | | | | | | | | | | | |
| | High | Intermediate | 11 | 36.6% | 0.5 [0.2-1.6]‡ | 11 | 54.5% | 1.0 [0.3-3.7]‡ | 10 | 80.0% | — |
| | High | Low | 1 | 0.0% | — | 1 | 0.0% | — | 1 | 0.0% | — |
| | Intermediate | Low | 24 | 0.0% | ? | 24 | 4.2% | 0.1 [0.0-0.8]‡‡ | 22 | 4.5% | 0.1 [0.0-0.6]‡‡ |

Hazard ratios for patients with: *continuously intermediate vs. low values;
**continuously high vs. intermediate values
***continuously high vs. low values;
†increasing low to intermediate vs. continuously low values;
††increasing intermediate to high vs. continuously intermediate values;
‡decreasing high to intermediate vs. continuously high values;
‡‡decreasing intermediate to low vs. continuously intermediate values

TABLE 17

28 and 90 day mortality rates following changes in PCT concentrations and MR-proADM severity levels

| | Biomarker Kinetics | | 28 day mortality | | | 90 day mortality | | |
|---|---|---|---|---|---|---|---|---|
| | Baseline | Day 4 | N | % | HR IQR [95% CI] | N | % | HR IQR [95% CI] |
| PCT decrease ≥50% | | | 557 | 17.1% | | 542 | 29.3% | |
| MR-proADM severity level | Low | Low | 111 | 1.8% | 11.2 [2.7-46.4]* | 107 | 7.5% | 5.3 [2.5-10.9]* |
| | Intermediate | Intermediate | 209 | 18.7% | 3.8 [2.3-6.5]** | 206 | 33.5% | 3.3 [2.1-5.1]** |
| | High | High | 39 | 53.8% | 43.1 [10.1-184.0]*** | 39 | 71.8% | 17.4 [7.9-38.2]*** |
| Increasing | | | | | | | | |
| | Low | Intermediate | 24 | 25.0% | 15.6 [3.1-77.2]† | 24 | 41.7% | 7.1 [2.8-17.9]† |
| | Intermediate | High | 23 | 43.5% | 2.6 [1.3-5.3]†† | 23 | 65.2% | 2.6 [1.5-4.5]†† |
| Decreasing | | | | | | | | |
| | High | Intermediate | 42 | 21.4% | 0.3 [0.1-0.7]‡ | 41 | 36.6% | 0.3 [0.2-0.6]‡ |
| | High | Low | 3 | 0.0% | — | 2 | 50.0% | — |
| | Intermediate | Low | 105 | 7.6% | 0.4 [0.2-0.8]‡‡ | 100 | 13.0% | 0.3 [0.2-0.6]‡‡ |
| PCT decrease <50% | | | 210 | 29.5% | | 203 | 45.5% | |

TABLE 17-continued 28 and 90 day mortality rates following changes in PCT concentrations and MR-proADM severity levels

| | Biomarker Kinetics | | 28 day mortality | | | 90 day mortality | | |
|---|---|---|---|---|---|---|---|---|
| | Baseline | Day 4 | N | % | HR IQR [95% CI] | N | % | HR IQR [95% CI] |
| MR-proADM severity level | Low | Low | 56 | 7.1% | 6.3 [2.2-18.1]* | 55 | 12.7% | 6.2 [2.8-13.9]* |
| | Intermediate | Intermediate | 70 | 38.6% | 1.5 [0.8-3.0]** | 68 | 57.4% | 1.3 [0.7-2.3]** |
| | High | High | 23 | 52.2% | 9.5 [3.1-29.5]*** | 22 | 63.6% | 7.9 [3.2-19.5]*** |
| | Increasing | | | | | | | |
| | Low | Intermediate | 17 | 17.6% | 2.8 [0.6-12.5]† | 15 | 53.3% | 5.5 [2.0-15.2]† |
| | Low | High | 4 | 0.0% | — | 4 | 25.0% | — |
| | Intermediate | High | 30 | 46.7% | 1.4 [0.7-2.6]†† | 30 | 66.7% | 1.3 [0.8-2.2]†† |
| | Decreasing | | | | | | | |
| | High | Intermediate | — | — | — | — | — | — |
| | High | Low | — | — | — | — | — | — |
| | Intermediate | Low | 10 | 20.0% | — | 9 | 33.4% | — |

Hazard ratios for patients with: *continuously intermediate vs. low values;
**continuously high vs. intermediate values
***continuously high vs. low values;
†Increasing low to intermediate vs. continuously low values;
††Increasing intermediate to high vs. continuously intermediate values;
‡decreasing high to intermediate vs. continuously high values;
‡‡Decreasing intermediate to low vs. continuously intermediate values

TABLE 18

ICU and hospital mortality rates following changes in PCT concentrations and MR-proADM severity levels

| | Baseline | Day 4 | ICU mortality | | | Hospital mortality | | |
|---|---|---|---|---|---|---|---|---|
| | | | N | % | HR IQR [95% CI] | N | % | HR IQR [95% CI] |
| PCT decrease ≥50% | | | 555 | 16.8% | | 532 | 24.1% | |
| MR-proADM severity level | Low | Low | 114 | 2.6% | 6.9 [2.1-23.1]* | 109 | 2.8% | 13.3 [4.1-43.8]* |
| | Intermediate | Intermediate | 208 | 15.9% | 8.1 [3.8-17.2]** | 197 | 27.4% | 5.1 [2.4-10.7]** |
| | High | High | 38 | 60.5% | 56.2 [15.0-210.2]*** | 38 | 65.8% | 67.9 [18.0-256.6]*** |
| | Low | Intermediate | 24 | 29.2% | 15.1 [3.6-64.1]† | 24 | 33.3% | 17.7 [4.2-73.6]† |
| | Intermediate | High | 23 | 43.5% | 4.1 [1.7-10.0]†† | 23 | 56.5% | 3.4 [1.4-8.3]†† |
| | High | Intermediate | 41 | 22.0% | 0.2 [0.1-0.5]‡ | 39 | 33.3% | 1.3 [0.6-2.7]‡ |
| | High | Low | 3 | 0.0% | — | 2 | 50.0% | — |
| | Intermediate | Low | 103 | 8.7% | 0.5 [0.2-1.0]‡‡ | 99 | 11.1% | 0.3 [0.2-0.7]‡‡ |
| PCT decrease <50% | | | 204 | 28.9% | | 194 | 30.4% | |
| MR-proADM severity level | Low | Low | 56 | 1.8% | 28.1 [3.7-216.3]* | 54 | 7.4% | 10.1 [3.3-31.2]* |
| | Intermediate | Intermediate | 68 | 33.8% | 1.8 [0.7-4.8]** | 65 | 44.6% | 1.9 [0.7-5.2]** |
| | High | High | 21 | 47.6% | 50.0 [5.8-431.5]*** | 20 | 60.0% | 18.8 [4.8-72.7]*** |
| | Low | Intermediate | 16 | 43.7% | 42.8 [4.7-390.2]† | 14 | 57.1% | 16.7 [3.8-72.4]† |
| | Low | High | 4 | 0.0% | — | 4 | 25.0% | — |
| | Intermediate | High | 29 | 58.6% | 2.8 [1.1-6.8]†† | 28 | 64.3% | 2.2 [0.9-5.6]†† |
| | High | Intermediate | — | — | — | — | — | — |
| | High | Low | — | — | — | — | — | — |
| | Intermediate | Low | 10 | 10.0% | — | 9 | 33.3% | — |

Hazard ratios for patients with: *continuously intermediate vs. low values;
**continuously high vs. intermediate values
***continuously high vs. low values;
†Increasing low to intermediate vs. continuously low values;
††Increasing intermediate to high vs. continuously intermediate values;
‡decreasing high to intermediate vs. continuously high values;
‡‡Decreasing intermediate to low vs. continuously intermediate values

TABLE 19

Influence of infectious origin on 28 day mortality prediction

| | | Patients (N) | Mortality (N) | AUROC | Univariate | | | | Multivariate | | | |
|---|---|---|---|---|---|---|---|---|---|---|---|---|
| | | | | | LR $X^2$ | C-index | HR IQR [95% CI] | p-value | LR $X^2$ | C-index | HR IQR [95% CI] | p-value |
| Pneumo-logical | MR-proADM | 313 | 83 | 0.72 | 37.9 | 0.69 | 2.7 [2.0-3.7] | <0.0001 | 45.1 | 0.71 | 2.5 [1.7-3.6] | <0.0001 |
| | PCT | 313 | 83 | 0.59 | 6.4 | 0.58 | 1.6 [1.1-2.2] | 0.0112 | 26.0 | 0.66 | 1.5 [1.1-2.2] | 0.0038 |
| | CRP | 267 | 65 | 0.46 | 0.8 | 0.53 | 0.9 [0.7-1.1] | 0.3754 | 14.7 | 0.63 | 0.9 [0.7-1.1] | 0.1422 |
| | Lactate | 322 | 86 | 0.61 | 12.6 | 0.61 | 1.6 [1.2-2.1] | 0.0004 | 30.1 | 0.67 | 1.5 [1.1-2.0] | 0.0008 |
| | SOFA | 315 | 83 | 0.63 | 12.4 | 0.62 | 1.7 [1.3-2.3] | 0.0004 | 29.6 | 0.68 | 1.6 [1.1-2.2] | 0.0010 |
| | SAPS II | 324 | 86 | 0.63 | 13.2 | 0.62 | 1.6 [1.3-2.1] | 0.0003 | 28.8 | 0.67 | 1.5 [1.1-1.9] | 0.0014 |
| | APACHE II | 324 | 86 | 0.63 | 19.5 | 0.64 | 1.9 [1.4-2.5] | <0.0001 | 33.4 | 0.68 | 1.7 [1.3-2.3] | 0.0002 |
| Intra-abdominal | MR-proADM | 238 | 58 | 0.78 | 47.4 | 0.75 | 4.5 [2.9-7.1] | <0.0001 | 55.7 | 0.76 | 4.8 [2.9-8.0] | <0.0001 |
| | PCT | 238 | 58 | 0.52 | 0.4 | 0.52 | 1.1 [0.8-1.7] | 0.5249 | 15.0 | 0.64 | 1.2 [0.8-1.9] | 0.1312 |
| | CRP | 233 | 59 | 0.48 | 0.1 | 0.53 | 1.0 [0.8-1.3] | 0.7807 | 12.0 | 0.62 | 1.1 [0.8-1.4] | 0.2864 |
| | Lactate | 249 | 62 | 0.67 | 18.0 | 0.66 | 2.2 [1.5-3.0] | <0.0001 | 28.2 | 0.70 | 2.1 [1.5-3.0] | 0.0017 |
| | SOFA | 248 | 62 | 0.66 | 8.9 | 0.63 | 1.5 [1.2-2.0] | 0.0029 | 18.3 | 0.64 | 1.5 [1.1-2.0] | 0.0494 |
| | SAPS II | 252 | 62 | 0.68 | 17.9 | 0.66 | 1.9 [1.4-2.6] | <0.0001 | 24.3 | 0.67 | 1.9 [1.3-2.6] | 0.0069 |
| | APACHE II | 252 | 62 | 0.68 | 14.6 | 0.65 | 1.8 [1.3-2.3] | 0.0001 | 20.6 | 0.66 | 1.6 [1.2-2.2] | 0.0241 |

MR-proADM AUROC values are significantly greater than all other parameters apart from APACHE II in pneumological origins of infection.

TABLE 20

Influence of microbial species on 28 day mortality prediction

| | | Patients (N) | Mortality (N) | AUROC | Univariate | | | | Multivariate | | | |
|---|---|---|---|---|---|---|---|---|---|---|---|---|
| | | | | | LR $X^2$ | C-index | HR IRQ [95% CI] | p-value | LR $X^2$ | C-index | HR IQR [95% CI] | p-value |
| Gram positive | MR-proADM | 141 | 33 | 0.82 | 37.2 | 0.81 | 5.0 [2.9-8.6] | <0.0001 | 50.0 | 0.84 | 5.0 [2.7-9.2] | <0.0001 |
| | PCT | 142 | 33 | 0.64 | 7.9 | 0.64 | 2.4 [1.3-4.4] | 0.0050 | 30.3 | 0.76 | 3.0 [1.5-5.7] | 0.0008 |
| | CRP | 131 | 31 | 0.54 | 0.2 | 0.51 | 0.9 [0.7-1.3] | 0.6561 | 19.8 | 0.71 | 1.0 [0.7-1.4] | 0.0309 |
| | Lactate | 143 | 33 | 0.75 | 28.9 | 0.74 | 4.6 [2.6-8.1] | <0.0001 | 44.9 | 0.83 | 5.0 [2.6-9.7] | <0.0001 |
| | SOFA | 143 | 32 | 0.66 | 8.8 | 0.65 | 1.9 [1.3-2.8] | 0.0031 | 31.8 | 0.76 | 2.7 [1.6-4.6] | 0.0004 |
| | SAPS II | 146 | 33 | 0.72 | 16.8 | 0.71 | 2.9 [1.7-4.7] | <0.0001 | 28.4 | 0.76 | 2.7 [1.5-4.9] | 0.0016 |
| | APACHE II | 146 | 33 | 0.73 | 17.3 | 0.71 | 2.4 [1.6-3.5] | <0.0001 | 33.1 | 0.77 | 2.8 [1.7-4.7] | 0.0003 |
| Gram negative | MR-proADM | 124 | 35 | 0.69 | 12.1 | 0.68 | 2.3 [1.4-3.8] | 0.0005 | 26.0 | 0.75 | 2.2 [1.2-3.8] | 0.0037 |
| | PCT | 124 | 35 | 0.54 | 0.6 | 0.54 | 1.2 [0.7-2.1] | 0.4580 | 17.8 | 0.67 | 1.2 [0.7-2.3] | 0.0580 |
| | CRP | 110 | 30 | 0.57 | 0.4 | 0.56 | 1.2 [0.7-1.8] | 0.5255 | 17.1 | 0.68 | 1.4 [0.9-2.2] | 0.0727 |
| | Lactate | 131 | 37 | 0.65 | 10.0 | 0.64 | 1.9 [1.3-2.8] | 0.0016 | 23.4 | 0.71 | 1.7 [1.1-2.7] | 0.0093 |
| | SOFA | 129 | 37 | 0.65 | 9.0 | 0.64 | 1.8 [1.2-2.7] | 0.0027 | 25.5 | 0.72 | 1.9 [1.2-2.9] | 0.0045 |
| | SAPS II | 132 | 37 | 0.67 | 9.9 | 0.65 | 1.9 [1.3-2.8] | 0.0017 | 25.1 | 0.71 | 1.9 [1.2-3.0] | 0.0051 |
| | APACHE II | 132 | 37 | 0.69 | 7.9 | 0.66 | 1.7 [1.2-2.4] | 0.0049 | 22.3 | 0.70 | 1.7 [1.1-2.6] | 0.0139 |
| Fungal | MR-proADM | 50 | 14 | 0.74 | 7.9 | 0.69 | 2.5 [1.3-4.9] | 0.0051 | 14.4 | 0.78 | 3.4 [1.4-10.7] | 0.1548 |
| | PCT | 50 | 14 | 0.46 | 0.3 | 0.52 | 1.3 [0.5-3.0] | 0.6104 | 8.5 | 0.72 | 1.1 [0.4-3.0] | 0.5792 |
| | CRP | 43 | 12 | 0.65 | 0.6 | 0.65 | 0.8 [0.5-1.3] | 0.4404 | 14.7 | 0.81 | 0.5 [0.2-1.2] | 0.1427 |
| | Lactate | 51 | 14 | 0.60 | 2.7 | 0.59 | 2.0 [0.9-4.7] | 0.1032 | 13.2 | 0.74 | 3.3 [1.0-11.0] | 0.2128 |
| | SOFA | 49 | 12 | 0.54 | 0.8 | 0.54 | 1.4 [0.7-2.8] | 0.3668 | 7.1 | 0.73 | 1.1 [0.5-2.8] | 0.7164 |
| | SAPS II | 51 | 14 | 0.60 | 2.2 | 0.60 | 1.5 [0.9-2.6] | 0.1412 | 10.0 | 0.75 | 1.4 [0.7-2.8] | 0.4427 |
| | APACHE II | 51 | 14 | 0.62 | 1.6 | 0.62 | 1.6 [0.8-3.3] | 0.2053 | 10.1 | 0.76 | 1.7 [0.7-4.4] | 0.4321 |

TABLE 21

Influence of mode of ICU entry on 28 day mortality prediction

| | | Patients (N) | Mortality (N) | AUROC | Univariate | | | | Multivariate | | | |
|---|---|---|---|---|---|---|---|---|---|---|---|---|
| | | | | | LR $X^2$ | C-index | HR IQR [95% CI] | p-value | LR $X^2$ | C-index | HR IQR [95% CI] | p-value |
| Operative | MR-proADM | 466 | 113 | 0.77 | 87.4 | 0.75 | 4.1 [3.0-5.6] | <0.0001 | 106.4 | 0.77 | 3.8 [2.8-5.3] | <0.0001 |
| | PCT | 466 | 113 | 0.60 | 11.8 | 0.59 | 1.6 [1.2-2.2] | 0.0006 | 53.1 | 0.70 | 1.7 [1.3-2.4] | <0.0001 |
| | CRP | 421 | 106 | 0.48 | 1.2 | 0.52 | 1.1 [0.9-1.4] | 0.2696 | 39.7 | 0.68 | 1.2 [0.9-1.4] | <0.0001 |
| | Lactate | 483 | 120 | 0.68 | 46.4 | 0.67 | 2.4 [1.9-3.1] | <0.0001 | 73.7 | 0.71 | 2.3 [1.8-3.0] | <0.0001 |
| | SOFA | 482 | 118 | 0.68 | 34.9 | 0.65 | 2.0 [1.6-2.4] | <0.0001 | 65.7 | 0.71 | 2.0 [1.6-2.5] | <0.0001 |
| | SAPS II | 489 | 120 | 0.71 | 50.5 | 0.68 | 2.2 [1.8-2.7] | <0.0001 | 65.9 | 0.70 | 2.0 [1.6-2.5] | <0.0001 |
| | APACHE II | 489 | 120 | 0.71 | 47.8 | 0.68 | 2.3 [1.8-2.8] | <0.0001 | 64.8 | 0.71 | 2.0 [1.6-2.5] | <0.0001 |

TABLE 21-continued

Influence of mode of ICU entry on 28 day mortality prediction

| | | Patients (N) | Mortality (N) | AUROC | Univariate | | | | Multivariate | | | |
|---|---|---|---|---|---|---|---|---|---|---|---|---|
| | | | | | LR X² | C-index | HR IQR [95% CI] | p-value | LR X² | C-index | HR IQR [95% CI] | p-value |
| Non-operative | MR-proADM | 448 | 132 | 0.70 | 48.6 | 0.68 | 2.6 [2.0-3.4] | <0.0001 | 56.5 | 0.69 | 2.4 [1.8-3.3] | <0.0001 |
| | PCT | 449 | 132 | 0.52 | 0.8 | 0.52 | 1.1 [0.9-1.5] | 0.3644 | 24.4 | 0.62 | 1.1 [0.8-1.4] | 0.0066 |
| | CRP | 424 | 121 | 0.50 | 0.2 | 0.49 | 1.0 [0.8-1.2] | 0.6280 | 23.6 | 0.62 | 1.0 [0.8-1.2] | 0.0088 |
| | Lactate | 462 | 137 | 0.62 | 24.5 | 0.62 | 1.9 [1.5-2.4] | <0.0001 | 43.7 | 0.67 | 1.8 [1.4-2.3] | <0.0001 |
| | SOFA | 450 | 132 | 0.62 | 15.9 | 0.61 | 1.7 [1.3-2.1] | 0.0001 | 39.5 | 0.66 | 1.7 [1.3-2.2] | <0.0001 |
| | SAPS II | 466 | 137 | 0.65 | 25.4 | 0.64 | 1.6 [1.3-1.9] | <0.0001 | 43.4 | 0.66 | 1.5 [1.3-2.8] | <0.0001 |
| | APACHE II | 466 | 137 | 0.64 | 23.9 | 0.63 | 1.7 [1.4-2.1] | <0.0001 | 40.2 | 0.66 | 1.6 [1.3-2.0] | <0.0001 |
| Elective | MR-proADM | 116 | 30 | 0.71 | 12.1 | 0.69 | 2.8 [1.6-5.2] | 0.0005 | 17.3 | 0.72 | 2.3 [1.2-4.5] | 0.0440 |
| | PCT | 116 | 30 | 0.59 | 3.3 | 0.59 | 1.6 [1.0-2.6] | 0.0675 | 15.1 | 0.70 | 1.7 [1.0-2.8] | 0.0873 |
| | CRP | 91 | 24 | 0.51 | 0.0 | 0.50 | 1.0 [0.7-1.4] | 0.8650 | 11.5 | 0.70 | 0.8 [0.5-1.3] | 0.3219 |
| | Lactate | 121 | 32 | 0.63 | 9.5 | 0.63 | 2.2 [1.4-3.6] | 0.0020 | 21.0 | 0.72 | 2.2 [1.3-3.6] | 0.0211 |
| | SOFA | 119 | 32 | 0.58 | 0.9 | 0.56 | 1.2 [0.9-1.6] | 0.3476 | 13.7 | 0.69 | 1.0 [0.7-1.3] | 0.1860 |
| | SAPS II | 121 | 32 | 0.60 | 1.4 | 0.59 | 1.3 [0.9-1.9] | 0.2333 | 13.1 | 0.68 | 0.9 [0.6-1.5] | 0.2177 |
| | APACHE II | 121 | 32 | 0.57 | 1.1 | 0.57 | 1.3 [0.8-1.9] | 0.2945 | 13.1 | 0.69 | 0.9 [0.6-1.5] | 0.2164 |

TABLE 22

Baseline biomarker and clinical score correlation with SOFA at baseline and day 1

| | Baseline SOFA | | | Day 1 SOFA | | |
|---|---|---|---|---|---|---|
| | Patients (N) | Correlation [95% CI] | p-value | Patients (N) | Correlation [95% CI] | p-value |
| MR-proADM | 1007 | 0.46 [0.41-0.51] | <0.0001 | | | |
| MR-proADM* | 969 | 0.47 [0.41-0.51] | <0.0001 | 969 | 0.57 [0.52-0.61] | <0.0001 |
| PCT | 1007 | 0.23 [0.17-0.29] | <0.0001 | 969 | 0.22 [0.16-0.28] | <0.0001 |
| CRP | 918 | 0.06 [0.00-0.13] | 0.0059 | 885 | 0.04 [0.00-0.12] | 0.2709 |
| Lactate | 1044 | 0.33 [0.27-0.38] | <0.0001 | 1005 | 0.40 [0.35-0.45] | <0.0001 |
| SAPS II | 1051 | 0.60 [0.56-0.64] | <0.0001 | 1011 | 0.50 [0.45-0.54] | <0.0001 |
| APACHE II | 1051 | 0.62 [0.58-0.65] | <0.0001 | 1011 | 0.53 [0.48-0.57] | <0.0001 |

*using the same patients on baseline as on day 1

TABLE 23

Baseline MR-proADM correlations with SOFA subscores on baseline and day 1

| | Baseline SOFA | | | Day 1 SOFA | | |
|---|---|---|---|---|---|---|
| SOFA subscore | Patients (N) | Correlation [95% CI] | p-value | Patients (N) | Correlation [95% CI] | p-value |
| Circulation | 1022 | 0.18 [0.12-0.23] | <0.0001 | 995 | 0.23 [0.17-0.29] | <0.0001 |
| Pulmonary | 1025 | 0.12 [0.06-0.18] | <0.0001 | 994 | 0.15 [0.09-0.21] | <0.0001 |
| Coagulation | 1028 | 0.30 [0.25-0.36] | <0.0001 | 1002 | 0.40 [0.35-0.45] | <0.0001 |
| Renal | 1030 | 0.50 [0.45-0.54] | <0.0001 | 1001 | 0.62 [0.58-0.66] | <0.0001 |
| Liver | 1014 | 0.20 [0.14-0.26] | <0.0001 | 993 | 0.36 [0.30-0.40] | <0.0001 |
| CNS | 1030 | 0.03 [−0.03-0.09] | 0.3856 | 1003 | 0.08 [0.02-0.14] | 0.0089 |

TABLE 24

Biomarker correlations with SOFA scores throughout ICU treatment

| | | MR-proADM | PCT | CRP | Lactate |
|---|---|---|---|---|---|
| Day 1 | Patients (N) | 960 | 960 | 894 | 1008 |
| | Correlation [95% CI] | 0.51 [0.46-0.55] | 0.24 [0.18-0.30] | −0.04 [−0.10-0.03] | 0.48 [0.43-0.53] |
| | p-value | <0.0001 | <0.0001 | <0.0001 | <0.0001 |

TABLE 24-continued

Biomarker correlations with SOFA scores throughout ICU treatment

|  |  | MR-proADM | PCT | CRP | Lactate |
|---|---|---|---|---|---|
| Day 4 | Patients (N) | 729 | 729 | 667 | 754 |
|  | Correlation [95% CI] | 0.58 | 0.13 | 0.14 | 0.36 |
|  |  | [0.53-0.63] | [0.06-0.20] | [0.06-0.21] | [0.29-0.42] |
|  | p-value | <0.0001 | 0.0003 | 0.0004 | <0.0001 |
| Day 7 | Patients (N) | 580 | 581 | 547 | 612 |
|  | Correlation [95% CI] | 0.58 | 0.05 | 0.15 | 0.43 |
|  |  | [0.53-0.64] | [−0.03-0.13] | [0.07-0.23] | [0.37-0.50] |
|  | p-value | <0.0001 | 0.2368 | 0.0004 | <0.0001 |
| Day 10 | Patients (N) | 473 | 473 | 429 | 483 |
|  | Correlation [95% CI] | 0.65 | 0.28 | 0.13 | 0.34 |
|  |  | [0.59-0.70] | [0.20-0.37] | [0.03-0.22] | [0.26-0.42] |
|  | p-value | <0.0001 | <0.0001 | 0.0076 | <0.0001 |

TABLE 25

Mortalities based on MR-proADM severities and increasing or decreasing PCT concentrations - Baseline to day 1

|  |  |  | 28 day mortality | | 90 day mortality | | 7 day mortality | | ICU mortality | | Hospital mortality | |
|---|---|---|---|---|---|---|---|---|---|---|---|---|
|  | Baseline | Day 1 | N | % | N | % | N | % | N | % | N | % |
|  | Decreasing PCT |  | 657 | 19.0% | 636 | 28.9% | 657 | 6.4% | 650 | 11.6% | 623 | 25.2 |
| MR-proADM | Low | Low | 161 | 5.0% | 157 | 14.0% | 163 | 2.5% | 162 | 5.6% | 157 | 8.3% |
| severity level | Intermediate | Intermediate | 314 | 19.1% | 308 | 31.8% | 316 | 4.7% | 310 | 17.1% | 299 | 27.8% |
|  | High | High | 51 | 58.8% | 50 | 64.0% | 51 | 23.5% | 51 | 54.9% | 49 | 63.3% |
|  | Increasing |  |  |  |  |  |  |  |  |  |  |  |
|  | Low | Intermediate | 10 | 20.0% | 10 | 30.0% | 11 | 0.0% | 11 | 18.2% | 10 | 20.0% |
|  | Intermediate | High | 17 | 35.3% | 17 | 41.2% | 17 | 17.6% | 17 | 29.4% | 17 | 41.2% |
|  | Decreasing |  |  |  |  |  |  |  |  |  |  |  |
|  | High | Intermediate | 35 | 40.0% | 34 | 47.1% | 35 | 20.0% | 34 | 41.2% | 32 | 50.0% |
|  | High | Low | — | — | — | — | — | — | — | — | — | — |
|  | Intermediate | Low | 63 | 7.9% | 60 | 10.0% | 63 | 1.6% | 63 | 7.9% | 58 | 8.6% |
|  | Increasing PCT |  | 329 | 35.0% | 319 | 46.6% | 331 | 17.5% | 324 | 35.8% | 31 | 42.3% |
| MR-proADM | Low | Low | 66 | 13.6% | 65 | 15.4% | 66 | 7.6% | 66 | 10.6% | 64 | 14.1% |
| severity level | Intermediate | Intermediate | 131 | 36.6% | 126 | 51.6% | 131 | 14.5% | 128 | 35.2% | 122 | 42.6% |
|  | High | High | 53 | 49.1% | 52 | 67.3% | 53 | 20.2% | 50 | 58.0% | 50 | 60.0% |
|  | Increasing |  |  |  |  |  |  |  |  |  |  |  |
|  | Low | Intermediate | 25 | 20.0% | 23 | 47.8% | 26 | 15.4% | 25 | 32.0% | 23 | 39.1% |
|  | Low | High | — | — | — | — | — | — | — | — | — | — |
|  | Intermediate | High | 38 | 57.9% | 38 | 76.3% | 39 | 30.8% | 39 | 61.5% | 36 | 72.2% |
|  | Decreasing |  |  |  |  |  |  |  |  |  |  |  |
|  | High | Intermediate | 6 | 50.0% | 6 | 66.7% | 6 | 33.3% | 6 | 50.0% | 6 | 83.3% |
|  | High | Low | 1 | 0.0% | 1 | 100.0% | 1 | 0.0% | 1 | 0.0% | 1 | 0.0% |
|  | Intermediate | Low | 9 | 22.2% | 8 | 25.0% | 9 | 0.0% | 9 | 0.0% | 8 | 0.0% |

TABLE 26

PCT kinetics from baseline to day 1-development of new infections over days 1, 2, 3, 4.

|  |  |  | New infections over Days 1, 2, 3, 4 | |
|---|---|---|---|---|
|  | Baseline | Day 1 | N | % |
|  | Decreasing PCT |  | 652 | 9.7% |
| MR-proADM severity | Low | Low | 161 | 6.8% |
| level | Intermediate | Intermediate | 315 | 11.7% |
|  | High | High | 51 | 11.8% |
|  | Increasing |  |  |  |
|  | Low | Intermediate | 10 | 0.0% |
|  | Intermediate | High | 17 | 5.9% |

TABLE 26-continued

PCT kinetics from baseline to day 1-development of new infections over days 1, 2, 3, 4.

| | | | New infections over Days 1, 2, 3, 4 | |
|---|---|---|---|---|
| | Baseline | Day 1 | N | % |
| | | Decreasing | | |
| | High | Intermediate | 34 | 8.8% |
| | High | Low | — | — |
| | Intermediate | Low | 63 | 7.9% |
| | Increasing PCT | | 329 | 18.5% |
| MR-proADM severity level | Low | Low | 66 | 9.1% |
| | Intermediate | Intermediate | 131 | 18.3% |
| | High | High | 53 | 22.6% |
| | | Increasing | | |
| | Low | Intermediate | 25 | 24.0% |
| | Low | High | — | — |
| | Intermediate | High | 38 | 18.4% |
| | | Decreasing | | |
| | High | Intermediate | 6 | 50.0% |
| | High | Low | 1 | 0.0% |
| | Intermediate | Low | 9 | 33.3% |

TABLE 27

PCT kinetics from baseline to day 4-development of new infections over days 4, 5, 6, 7.

| | | | New infections over Days 4, 5, 6, 7 | |
|---|---|---|---|---|
| | Baseline | Day 4 | N | % |
| | Decreasing PCT | | 681 | 14.5% |
| MR-proADM severity level | Low | Low | 144 | 8.3% |
| | Intermediate | Intermediate | 256 | 17.6% |
| | High | High | 57 | 28.1% |
| | | Increasing | | |
| | Low | Intermediate | 31 | 22.6% |
| | Intermediate | High | 36 | 13.9% |
| | | Decreasing | | |
| | High | Intermediate | 42 | 11.9% |
| | High | Low | 3 | 0.0% |
| | Intermediate | Low | 111 | 8.1% |

TABLE 28

PCT kinetics from baseline to day 1-requirement for focus cleaning over days 1, 2, 3, 4.

| | | | Focus cleaning events over days 1, 2, 3, 4 | |
|---|---|---|---|---|
| | Baseline | Day 1 | N | % |
| | Increasing PCT | | 329 | 21.0% |
| MR-proADM severity level | Low | Low | 57 | 10.5% |
| | Intermediate | Intermediate | 113 | 20.4% |
| | High | High | 58 | 19.0% |
| | | Increasing | | |
| | Low | Intermediate | 31 | 32.3% |
| | Low | High | 3 | 33.3% |
| | Intermediate | High | 59 | 28.8% |

TABLE 28-continued

PCT kinetics from baseline to day 1-requirement for focus cleaning over days 1, 2, 3, 4.

| | | Focus cleaning events over days 1, 2, 3, 4 | |
|---|---|---|---|
| Baseline | Day 1 | N | % |
| Decreasing | | | |
| High | Intermediate | 1 | 0.0% |
| High | Low | 1 | 100.0% |
| Intermediate | Low | 6 | 0.0% |

TABLE 29

PCT kinetics from baseline to day 4-requirement for focus cleaning over days 4, 5, 6, 7.

| | | | Focus cleaning events over days 4, 5, 6, 7 | |
|---|---|---|---|---|
| | Baseline | Day 4 | N | % |
| | Decreasing PCT | | 681 | 22.0% |
| MR-proADM severity level | Low | Low | 144 | 16.7% |
| | Intermediate | Intermediate | 256 | 24.2% |
| | High | High | 57 | 31.6% |
| | Increasing | | | |
| | Low | Intermediate | 31 | 32.3% |
| | Intermediate | High | 36 | 50.0% |
| | Decreasing | | | |
| | High | Intermediate | 42 | 16.7% |
| | High | Low | 3 | 0.0% |
| | Intermediate | Low | 111 | 9.9% |

35

TABLE 30

PCT kinetics from baseline to day 1-requirement of emergency surgery over days 1, 2, 3, 4.

| | | | Emergency surgery requirement over days 1, 2, 3, 4 | |
|---|---|---|---|---|
| | Baseline | Day 1 | N | % |
| | Increasing PCT | | 329 | 23.7% |
| MR-proADM severity level | Low | Low | 66 | 18.2% |
| | Intermediate | Intermediate | 131 | 26.0% |
| | High | High | 53 | 28.3% |
| | Increasing | | | |
| | Low | Intermediate | 25 | 16.0% |
| | Low | High | — | — |
| | Intermediate | High | 38 | 31.6% |
| | Decreasing | | | |
| | High | Intermediate | 6 | 0.0% |
| | High | Low | 1 | 100.0% |
| | Intermediate | Low | 9 | 0.0% |

TABLE 31

Increasing PCT from baseline to day 1-antibiotic changes on day 4

| | Increasing PCT | | 259 | 21.6% |
|---|---|---|---|---|
| MR-proADM severity level | Low | Low | 55 | 5.5% |
| | Intermediate | Intermediate | 106 | 27.4% |
| | High | High | 39 | 25.6% |
| | | Increasing | | |
| | Low | Intermediate | 20 | 25.0% |
| | Intermediate | High | 26 | 26.9% |
| | | Decreasing | | |
| | High | Intermediate | 5 | 20.0% |
| | High | Low | 1 | 100.0% |
| | Intermediate | Low | 7 | 0.0% |

TABLE 32

Increasing PCT from baseline to day 4-antibiotic changes on day 4

| | Increasing PCT | | 85 | 23.5% |
|---|---|---|---|---|
| MR-proADM severity level | Low | Low | 23 | 8.7% |
| | Intermediate | Intermediate | 22 | 36.4% |
| | High | High | 5 | 20.0% |
| | | Increasing | | |
| | Low | Intermediate | 10 | 20.0% |
| | Intermediate | High | 17 | 41.2% |
| | Low | High | 4 | 0.0% |
| | | Decreasing | | |
| | High | Intermediate | — | — |
| | High | Low | — | — |
| | Intermediate | Low | 4 | 0.0% |

TABLE 33

Biomarker levels based on platelet count

| Platelet level ($10^3/\mu l$) | Patients (N) | Mortality (N, %) | Median Platelet count (baseline; $10^3/\mu l$)) | Median proADM level (baseline) | Median PCT level (baseline) | Platelet transfusion | Median Platelet count (day 1; $10^3/\mu l$)) | Median proADM level (day 1) | Median PCT level (day 1) |
|---|---|---|---|---|---|---|---|---|---|
| <20 | 3 | 1 (33.3%) | 12 | 15.6 | 171.7 | 1 (33.3%) | 15 | 9.8 | 58.1 |
| 20 to <150 | 233 | 90 (38.6%) | 109 | 6.6 | 9.0 | 24 (10.3%) | 78 | 5.5 | 7.4 |
| 150 to 399 | 658 | 165 (25.1%) | 249 | 4.5 | 7.0 | 11 (1.7%) | 191 | 4.3 | 5.8 |
| >399 | 177 | 32 (18.1%) | 494 | 4.9 | 5.7 | 1 (0.6%) | 342 | 3.7 | 4.3 |

TABLE 34

Platelet count based on proADM levels

| MR-proADM (nmol/L) | Patients (N) | Mortality (N, %) | Median Platelet count (baseline; $10^3/\mu l$)) | Platelet transfusion | Median Platelet count (day 1; $10^3/\mu l$)) | % Platelet decrease from baseline | Median proADM level (day 1) | Day 1 Thrombocytopenia development |
|---|---|---|---|---|---|---|---|---|
| ≤2.75 | 271 | 28 (10.3%) | 251.5 | 3 (1.1%) | 206 | 18% | 1.7 | 73 (26.9%) |
| >2.75 and ≤10.9 | 594 | 157 (26.4%) | 246 | 14 (2.4%) | 177 | 28% | 5.0 | 249 (41.9%) |
| >10.9 | 165 | 90 (54.5%) | 178.5 | 19 (11.5%) | 103.5 | 42% | 11.8 | 102 (61.8%) |

TABLE 35

Development of Thrombocytopenia and proADM kinetics at baseline and day 1.

| MR-proADM (nmol/L) | Patients (N) | Mortality (N, %) | Median Platelet count (baseline; $10^3/\mu l$) | Platelet transfusion | Median Platelet count (day 1; $10^3/\mu l$) | % Platelet decrease from baseline | Median proADM level (day 1) | Day 1 Thrombocytopenia development |
|---|---|---|---|---|---|---|---|---|
| ≤2.75 | 232 | 21 (9.1%) | 274 | 1 (0.4%) | 227 | 17.2% | 1.75 | 34 (14.7%) |
| >2.75 and ≤10.9 | 464 | 112 (24.1%) | 281 | 5 (1.1%) | 215 | 23.5% | 4.9 | 119 (25.6%) |
| >10.9 | 104 | 53 (51.0%) | 259 | 5 (4.8%) | 162 | 37.5% | 11.6 | 41 (39.4%) |

REFERENCES

1. Martin G S, Mannino D M, Eaton S, Moss M. The epidemiology of sepsis in the United States from 1979 through 2000. N Engl J Med. Apr. 17 2003; 348(16): 1546-1554.
2. Kaukonen K M, Bailey M, Suzuki S, Pilcher D, Bellomo R. Mortality related to severe sepsis and septic shock among critically ill patients in Australia and New Zealand, 2000-2012. JAMA. Apr. 2 2014; 311(13):1308-1316.
3. Vincent J L, Sakr Y, Sprung C L, et al. Sepsis in European intensive care units: results of the SOAP study. Crit Care Med. February 2006; 34(2):344-353.
4. Singer M, Deutschman C S, Seymour C W, et al. The Third International Consensus Definitions for Sepsis and Septic Shock (Sepsis-3). JAMA. Feb. 23 2016; 315(8): 801-810.
5. Kopterides P, Siempos, I I, Tsangaris I, Tsantes A, Armaganidis A. Procalcitonin-guided algorithms of antibiotic therapy in the intensive care unit: a systematic review and meta-analysis of randomized controlled trials. Crit Care Med. November 2010; 38(11):2229-2241.
6. de Jong E, van Oers J A, Beishuizen A, et al. Efficacy and safety of procalcitonin guidance in reducing the duration of antibiotic treatment in critically ill patients: a randomised, controlled, open-label trial. Lancet Infect Dis. July 2016; 16(7):819-827.
7. Harbarth S, Holeckova K, Froidevaux C, et al. Diagnostic value of procalcitonin, interleukin-6, and interleukin-8 in critically ill patients admitted with suspected sepsis. Am J Respir Crit Care Med. Aug. 1 2001; 164(3):396-402.
8. Andriolo B N, Andriolo R B, Salomao R, Atallah A N. Effectiveness and safety of procalcitonin evaluation for reducing mortality in adults with sepsis, severe sepsis or septic shock. Cochrane Database Syst Rev. Jan. 18 2017; 1:CD010959.
9. Temmesfeld-Wollbruck B, Brell B, David I, et al. Adrenomedullin reduces vascular hyperpermeability and improves survival in rat septic shock. Intensive Care Med. April 2007; 33(4):703-710.
10. Muller-Redetzky H C, Will D, Hellwig K, et al. Mechanical ventilation drives pneumococcal pneumonia into lung injury and sepsis in mice: protection by adrenomedullin. Crit Care. 2014; 18(2):R73.
11. Vallet B. Endothelial cell dysfunction and abnormal tissue perfusion. Crit Care Med. May 2002; 30(5 Suppl): S229-234.
12. Gonzalez-Rey E, Chorny A, Varela N, Robledo G, Delgado M. Urocortin and adrenomedullin prevent lethal endotoxemia by down-regulating the inflammatory response. Am J Pathol. June 2006; 168(6):1921-1930.
13. Carrizo G J, Wu R, Cui X, Dwivedi A J, Simms H H, Wang P. Adrenomedullin and adrenomedullin-binding protein-1 downregulate inflammatory cytokines and attenuate tissue injury after gut ischemia-reperfusion. Surgery. February 2007; 141(2):245-253.
14. Brell B, Hippenstiel S, David I, et al. Adrenomedullin treatment abolishes ileal mucosal hypoperfusion induced by *Staphylococcus aureus* alpha-toxin—an intravital microscopic study on an isolated rat ileum. Crit Care Med. December 2005; 33(12):2810-2016.
15. Brell B, Temmesfeld-Wollbruck B, Altzschner I, et al. Adrenomedullin reduces *Staphylococcus aureus* alpha-toxin-induced rat ileum microcirculatory damage. Crit Care Med. April 2005; 33(4):819-826.
16. Vigue B, Leblanc P E, Moati F, et al. Mid-regional pro-adrenomedullin (M R-proADM), a marker of positive fluid balance in critically ill patients: results of the ENVOL study. Crit Care. Nov. 9 2016; 20(1):363.
17. Andaluz-Ojeda D, Cicuendez R, Calvo D, et al. Sustained value of proadrenomedullin as mortality predictor in severe sepsis. J Infect. July 2015; 71(1):136-139.
18. Hartmann O, Schuetz P, Albrich W C, Anker S D, Mueller B, Schmidt T. Time-dependent Cox regression: serial measurement of the cardiovascular biomarker proadrenomedullin improves survival prediction in patients with lower respiratory tract infection. Int J Cardiol. Nov. 29 2012; 161(3):166-173.
19. Albrich W C, Dusemund F, Ruegger K, et al. Enhancement of CURB65 score with proadrenomedullin (CURB65-A) for outcome prediction in lower respiratory tract infections: derivation of a clinical algorithm. BMC Infect Dis. 2011; 11:112.
20. Albrich W C, Ruegger K, Dusemund F, et al. Optimised patient transfer using an innovative multidisciplinary assessment in Kanton Aargau (OPTIMA I): an observational survey in lower respiratory tract infections. Swiss Med Wkly. 2011; 141:w13237.
21. Albrich W C, Ruegger K, Dusemund F, et al. Biomarker-enhanced triage in respiratory infections: a proof-of-concept feasibility trial. Eur Respir J. October 2013; 42(4):1064-1075.
22. Riera J, Senna A, Cubero M, Roman A, Rello J, Study Group Investigators T V. Primary Graft Dysfunction and Mortality Following Lung Transplantation: A Role for Proadrenomedullin Plasma Levels. Am J Transplant. Oct. 13 2015.
23. Schoe A, Schippers E F, Struck J, et al. Postoperative pro-adrenomedullin levels predict mortality in thoracic surgery patients: comparison with Acute Physiology and Chronic Health Evaluation IV Score*. Crit Care Med. February 2015; 43(2):373-381.
24. Tyagi A, Sethi A K, Girotra G, Mohta M. The microcirculation in sepsis. Indian J Anaesth. June 2009; 53(3): 281-293.
25. Hernandez G, Bruhn A, Ince C. Microcirculation in sepsis: new perspectives. Curr Vasc Pharmacol. Mar. 1 2013; 11(2):161-169.
26. Bloos F, Trips E, Nierhaus A, et al. Effect of Sodium Selenite Administration and Procalcitonin-Guided Therapy on Mortality in Patients With Severe Sepsis or Septic Shock: A Randomized Clinical Trial. JAMA Intern Med. Sep. 1, 2016; 176(9):1266-1276.
27. Bloos F, Ruddel H, Thomas-Ruddel D, et al. Effect of a multifaceted educational intervention for anti-infectious measures on sepsis mortality: a cluster randomized trial. Intensive Care Med. May 2 2017.
28. Enguix-Armada A, Escobar-Conesa R, La Torre A G, De La Torre-Prados M V. Usefulness of several biomarkers in the management of septic patients: C-reactive protein, procalcitonin, presepsin and mid-regional pro-adrenomedullin. Clin Chem Lab Med. Jun. 17 2015.
29. Christ-Crain M, Morgenthaler N G, Struck J, Harbarth S, Bergmann A, Muller B. Mid-regional pro-adrenomedullin as a prognostic marker in sepsis: an observational study. Crit Care. 2005; 9(6):R816-824.
30. Suberviola B, Castellanos-Ortega A, Ruiz Ruiz A, Lopez-Hoyos M, Santibanez M. Hospital mortality prognostication in sepsis using the new biomarkers suPAR and proADM in a single determination on ICU admission. Intensive Care Med. November 2013; 39(11):1945-1952.

31. Gillmann H J, Meinders A, Larmann J, et al. Adrenomedullin Is Associated With Surgical Trauma and Impaired Renal Function in Vascular Surgery Patients. J Intensive Care Med. Jan. 1 2017:885066616689554.

32. Garrouste-Orgeas M, Montuclard L, Timsit J F, Misset B, Christias M, Carlet J. Triaging patients to the ICU: a pilot study of factors influencing admission decisions and patient outcomes. Intensive Care Med. May 2003; 29(5): 774-781.

33. Garrouste-Orgeas M, Montuclard L, Timsit J F, et al. Predictors of intensive care unit refusal in French intensive care units: a multiple-center study. Crit Care Med. April 2005; 33(4):750-755.

34. Mery E, Kahn J M. Does space make waste? The influence of ICU bed capacity on admission decisions. Crit Care. May 8 2013; 17(3):315.

35. Orsini J, Blaak C, Yeh A, et al. Triage of Patients Consulted for ICU Admission During Times of ICU-Bed Shortage. J Clin Med Res. December 2014; 6(6):463-468.

36. Kip M M, Kusters R, M J I J, Steuten L M. A PCT algorithm for discontinuation of antibiotic therapy is a cost-effective way to reduce antibiotic exposure in adult intensive care patients with sepsis. J Med Econ. 2015; 18(11):944-953.

37. Wilke M H, Grube R F, Bodmann K F. The use of a standardized PCT-algorithm reduces costs in intensive care in septic patients—a DRG-based simulation model. Eur J Med Res. Dec. 2 2011; 16(12):543-548.

38. Baughman R P, Lower E E, Flessa H C, Tollerud D J. Thrombocytopenia in the intensive care unit. Chest. 1993; 104(4):1243-7.7.

39. Drews R E, Weinberger S E. Thrombocytopenic disorders in critically ill patients. Am J Respir Crit Care Med. 2000; 162(2 Pt 1):347-51.

40. Vanderschueren S, De Weerdt A, Malbrain M, Vankersschaever D, Frans E, Wilmer A, et al. Thrombocytopenia and prognosis in intensive care. Crit Care Med. 2000; 28(6):1871-6. 9.

41. Strauss R, Wehler M, Mehler K, Kreutzer D, Koebnick C, Hahn E G. Thrombocytopenia in patients in the medical intensive care unit: bleeding prevalence, transfusion requirements, and outcome. Crit Care Med. 2002; 30(8): 1765-71. 10.

42. Smith-Erichsen N. Serial determinations of platelets, leucocytes and coagulation parameters in surgical septicemia. Scand J Clin Lab Invest Suppl. 1985; 178:7-14. 11.

43. Akca S, Haji-Michael P, de Mendonca A, Suter P, Levi M, Vincent J L. Time course of platelet counts in critically ill patients. Crit Care Med. 2002; 30(4):753-6. 12.

44. Crowther M A, Cook D J, Meade M O, Grifth L E, Guyatt G H, Arnold D M, et al. Thrombocytopenia in medical-surgical critically ill patients: prevalence, incidence, and risk factors. J Crit Care. 2005; 20(4):348-53. 13.

45. Moreau D, Timsit J F, Vesin A, Garrouste-Orgeas M, de Lassence A, Zahar J R, et al. Platelet count decline: an early prognostic marker in critically ill patients with prolonged ICU stays. Chest. 2007; 131(6):1735-41. 14.

46. Hui P, Cook D J, Lim W, Fraser G A, Arnold D M. The frequency and clinical significance of thrombocytopenia complicating critical illness: a systematic review. Chest. 2011; 139(2):271-8.15.

47. Venkata C, Kashyap R, Farmer J C, Afessa B. Thrombocytopenia in adult patients with sepsis: incidence, risk factors, and its association with clinical outcome. J Intensive Care. 2013; 1(1):9.

48. Semple J W, Freedman J. Platelets and innate immunity. Cell Mol Life Sci. 2010; 67(4):499-511. 17.

49. Semple J W, Italiano J E Jr, Freedman J. Platelets and the immune continuum. Nat Rev Immunol. 2011; 11(4):264-74.18.

50. Vieira-de-Abreu A, Campbell R A, Weyrich A S, Zimmerman G A. Platelets: versatile efector cells in hemostasis, infammation, and the immune continuum. Semin Immunopathol. 2012; 34(1):5-30. 19.

51. Herter J M, Rossaint J, Zarbock A. Platelets in infammation and immunity. J Thromb Haemost. 2014; 12(11): 1764-75.20.

52. Morrell C N, Aggrey A A, Chapman L M, Modjeski K L. Emerging roles for platelets as immune and inflammatory cells. Blood. 2014; 123(18):2759-67. 21.

53. Xu X R, Zhang D, Oswald B E, Carrim N, Wang X, Hou Y, et al. Platelets are versatile cells: new discoveries in hemostasis, thrombosis, immune responses, tumor metastasis and beyond. Crit Rev Clin Lab Sci. 2016; 53(6): 409-30.

54. Yu-Min Shen et al. Evaluating Thrombocytopenia during heparin therapy. Jama. February 2018; Egede Johansen et al. The potential of antimicrobials to induce thrombocytopenia in critically ill patients: data from a randomized controlled trial. PLOS one. November 2013; Vol. 8.

55. Van der Poll et al. Pathogenisis of DIC in sepsis. Sepsis. 1999; 103-109; Koyama et al. Time course of immature platelet count and its relation to thrombocytopenia and mortality in patients with sepsis. PLOS one. January 2018.

56. Guru et al. Association of Thrombocytopenia and Mortality in Critically Ill Patients on Continuous Renal Replacement Therapy. Nephron. 2016; 133:175-182.

57. Larkin et al. Sepsis-associated thrombocytopenia. Thrombosis Research. 2016;

58. Ali N., Auerbach H. (2017), New-onset acute thrombocytopenia in hospitalized patients: pathophysiology and diagnostic approach, Journal of Community Hospital Internal Medicine Perspectives, 7:3, 157-167.

59. Dewitte et al. Blood platelets and sepsis pathophysiology: A new therapeutic prospect in critical ill patients?. Ann. Intensive Care. 2017; 7:115.

The invention claimed is:

1. A method comprising:
preparing a sample comprising bodily fluid from a patient, and an antibody which binds to proADM or fragment(s) thereof,
wherein the patient has platelet levels below 150,000 platelets per microliter of
blood and/or thrombocytopenia and/or disseminated intravascular coagulation (DIC), and
wherein the level of detectable proADM or fragment(s) in the sample is equal to or greater than 6.5 nmol/l±20%.

2. The method according to claim 1, wherein the bodily fluid from the patient is selected from the group consisting of a blood, a blood plasma, a blood serum and a urine sample.

3. The method according to claim 1, wherein the sample of said patient is a first sample isolated before, at or after a time point of a diagnosis and a treatment initiation, and wherein the method further comprises,
a. providing a second sample, wherein said second sample has been isolated after the first sample and after the time point of treatment initiation, and
b. wherein the level of proADM or fragment(s) thereof in the second sample is different than the level of proADM or fragment(s) thereof in the first sample.

4. The method according to claim 1, wherein the patient has been diagnosed with an infectious disease and/or one or more existing organ failure(s), or has been diagnosed as suffering from sepsis, severe sepsis or septic shock.

5. The method according to claim 1, wherein patient has been diagnosed with one or more existing organ failure(s) and/or is a posttraumatic or postsurgical patient.

6. The method according to claim 1, wherein the antibody to proADM or fragment(s) thereof binds mid-regional (MR)-proADM in the sample.

7. The method according to claim 1, wherein the sample further comprises an antibody to at least one additional marker, selected from the group consisting of PCT, lactate and C-reactive protein, sCD14-ST, prothrombinase, antithrombin, cationic protein 18 (CAP18), von Willebrand factor (vWF)-cleaving proteases, lipoproteins in combination with CRP, fibrinogen, fibrin, B2GP1, GPIIb-IIIa, nondenatured D-dimer of fibrin, platelet factor 4 and one or more histones.

8. The method according to claim 1, wherein the level of proADM or fragments thereof is equal to or greater than 7.7 nmol/l±20%.

9. The method according to claim 1, wherein the level of proADM or fragments thereof is equal to or greater than 9.5 nmol/l±20%.

10. The method according to claim 1, wherein the level of proADM or fragments thereof is equal to or greater than 10.9 nmol/l±20%.

11. A method, comprising:
preparing a sample comprising bodily fluid from a patient, and an antibody which binds to proADM or fragment(s) thereof,
wherein the patient has platelet levels below 150,000 platelets per microliter of blood and/or thrombocytopenia and/or disseminated intravascular coagulation (DIC), and
wherein the level of detectable procalcitonin (PCT) or fragment(s) thereof is equal to or greater than 0.5 ng/ml, and wherein the level of detectable proADM or fragment(s) thereof is equal to or greater than 6.5 nmol/l.

12. The method according to claim 11, wherein the sample further comprises at least one additional labeled marker which have been labeled with a luminescence molecule,
wherein the at least one additional labeled marker is selected from the group consisting of lactate and C-reactive protein, sCD14-ST, prothrombinase, antithrombin, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4 and one or more histones.

13. A sample comprising:
a bodily fluid from a patient, an antibody bound to procalcitonin (PCT) or fragment(s), and an antibody bound to proADM or fragment(s) thereof,
wherein the patient has platelet levels below 150,000 platelets per microliter of blood and/or thrombocytopenia and/or disseminated intravascular coagulation (DIC), and
wherein the level of detectable proADM or fragment(s) thereof is equal to or greater than 6.5 nmol/l±20%,
or
a bodily fluid from a patient, an antibody bound to procalcitonin (PCT) or fragment(s), and an antibody bound to proADM or fragment(s) thereof,
wherein the patient has platelet levels below 150,000 platelets per microliter of
blood and/or thrombocytopenia and/or disseminated intravascular coagulation (DIC),
wherein the level of detectable procalcitonin (PCT) or fragment(s) thereof is equal to or greater than 0.5 ng/ml, and wherein the level of proADM or fragment(s) thereof is equal to or greater than 6.5 nmol/l.

14. The sample according to claim 13, wherein the bodily fluid is selected from the group consisting of blood, a blood plasma, blood serum and urine.

15. The sample according to claim 13, wherein the level of proADM or fragments thereof is equal to or greater than 7.7 nmol/l±20%.

16. The sample according to claim 13, wherein the level of proADM or fragments thereof is equal to or greater than 10.9 nmol/l±20%.

17. The sample according to claim 13, wherein the level of proADM or fragments thereof is equal to or greater than 9.5 nmol/l±20%.

\* \* \* \* \*